(12) United States Patent
Mashimo et al.

(10) Patent No.: US 12,371,713 B2
(45) Date of Patent: Jul. 29, 2025

(54) METHOD FOR PRODUCING DNA-EDITED EUKARYOTIC CELL, AND KIT USED IN THE SAME

(71) Applicant: OSAKA UNIVERSITY, Suita (JP)

(72) Inventors: Tomoji Mashimo, Suita (JP); Junji Takeda, Suita (JP); Hiroyuki Morisaka, Suita (JP); Kazuto Yoshimi, Suita (JP)

(73) Assignee: OSAKA UNIVERSITY, Osaka (JP)

( * ) Notice: Subject to any disclaimer, the term of this patent is extended or adjusted under 35 U.S.C. 154(b) by 0 days.

(21) Appl. No.: 18/467,297

(22) Filed: Sep. 14, 2023

(65) Prior Publication Data
US 2024/0124898 A1 Apr. 18, 2024

Related U.S. Application Data

(63) Continuation of application No. 16/611,308, filed as application No. PCT/JP2018/022066 on Jun. 8, 2018, now Pat. No. 11,807,869.

(30) Foreign Application Priority Data

Jun. 8, 2017 (JP) ................ 2017-113747

(51) Int. Cl.
| | |
|---|---|
| C12N 5/14 | (2006.01) |
| A61K 48/00 | (2006.01) |
| C12N 5/16 | (2006.01) |
| C12N 9/22 | (2006.01) |
| C12N 15/85 | (2006.01) |
| C12N 15/90 | (2006.01) |

(52) U.S. Cl.
CPC ............ *C12N 15/907* (2013.01); *A61K 48/00* (2013.01); *C12N 5/14* (2013.01); *C12N 5/16* (2013.01); *C12N 9/22* (2013.01); *C12N 15/85* (2013.01); *C12N 15/8509* (2013.01); *C12N 2310/20* (2017.05); *C12N 2800/22* (2013.01); *C12N 2800/80* (2013.01)

(58) Field of Classification Search
None
See application file for complete search history.

(56) References Cited

U.S. PATENT DOCUMENTS

| | | | |
|---|---|---|---|
| 2014/0294773 A1 | 10/2014 | Brouns et al. | |
| 2017/0028083 A1 | 2/2017 | Beisel et al. | |
| 2018/0334688 A1* | 11/2018 | Gersbach | ............... C12N 15/52 |
| 2019/0323038 A1 | 10/2019 | Wiedenheft | |
| 2021/0363520 A1 | 11/2021 | Osakabe et al. | |

FOREIGN PATENT DOCUMENTS

| | | |
|---|---|---|
| CN | 107557373 A | 1/2018 |
| CN | 107557378 A | 1/2018 |
| JP | 2015-503535 A | 2/2015 |
| JP | 2017-521481 A | 5/2017 |
| WO | 2014/093595 A1 | 6/2014 |
| WO | 2016/205613 A1 | 12/2016 |
| WO | 2017/043573 A1 | 3/2017 |
| WO | 2017/066497 A2 | 4/2017 |
| WO | 2017/219033 A1 | 12/2017 |
| WO | 2020/184723 A1 | 9/2020 |

OTHER PUBLICATIONS

Scholz et al., CRISPR-Cas Systems in the Cyanobacterium *Synechocystis* sp. PCC6803 Exhibit Distinct Processing Pathways Involving at Least Two Cas6 and a Cmr2 Protein. PLOS One (2013), 8:2, e56470 (Year: 2013).*
Koonin et al., The CRISPR Spacer Space Is Dominated by Sequences from Species-Specific Mobilomes. mBio (2017), 8:5, e01397-17 (Year: 2017).*
Hou and Lin, Distinct Gene Number-Genome Size Relationships for Eukaryotes and Non-Eukaryotes: Gene Content Estimation for Dinoflagellate Genomes. PLOS One (2009), 4:9, e6978 (Year: 2009).*
Koonin et al., Diversity, classification and evolution of CRISPR-Cas systems. Current Opinion in Microbiology (2017), 37: 67-78 (Year: 2017).*
Makarova et al., An updated evolutionary classification of CRISPR-Cas systems. Nat Rev Microbiol. (2015), 13(11) 722-736 (Year: 2015).*
Kuno et al., Intricate Interactions between the Bloom-Forming Cyanobacterium Microcystis aeruginosa and Foreign Genetic Elements, Revealed by Diversified Clustered Regularly Interspaced Short Palindromic Repeat (CRISPR) Signatures. Applied and Environmental Microbiology (2012), 78: 5353-5360 (Year: 2012).*
Tan et al., Cas1 enables genome engineering in human cells with compact CRISPR-Cas3 systems. Mol Cell (2022), 82: 852-867 (Year: 2022).
Martin Jinek et al., "A Programmable Dual-RNA-Guided DNA Endonuclease in Adaptive Bacterial Immunity", Science, Aug. 17, 2012, pp. 816-821, vol. 337.
Sabin Mulepati et al., "In Vitro Reconstitution of an *Escherichia coli* RNA-guided Immune System Reveals Unidirectional, ATP-dependent Degradation of DNA Target", The Journal of Biological Chemistry, Aug. 2, 2013, pp. 22184-22192, vol. 288, No. 33.
Ahmed A. Gomaa et al., "Programmable Removal of Bacterial Strains by Use of Genome-Targeting CRISPR-Cas Systems", mBIO, Jan./Feb. 2014, pp. 1-9, vol. 5, No. 1.
Keiichiro Suzuki et al., "In vivo genome editing via CRISPR/Cas9 mediated homology—independent targeted integration", Nature, Dec. 1, 2016, 24 pgs., vol. 540.
H. Morisaka et al., "Genetic Disease, Gene Regulation and Gene Therapy", Journal of Investigative Dermatology, May 2017, 3 pgs., vol. 137, No. 5.

(Continued)

*Primary Examiner* — Abigail Vanhorn
*Assistant Examiner* — Catherine Konopka
(74) *Attorney, Agent, or Firm* — Sughrue Mion, PLLC

(57) ABSTRACT

A CRISPR-Cas3 system was successfully established in a eukaryotic cell.

5 Claims, 28 Drawing Sheets

Specification includes a Sequence Listing.

(56) References Cited

OTHER PUBLICATIONS

Hiroyuki Morisaka et al., "Genome editing in mammalian cells by Cascade and Cas3", The 42nd Annual Meeting of the Japanese Society for Investigative Dermatology, Nov. 2, 2017, P07-20 [04-12], 3pgs.

International Search Report for PCT/JP2018/022066 dated, Sep. 4, 2018 (PCT/ISA/210).

Communication dated Dec. 12, 2019 issued in International Application No. PCT/JP2018/022066.

Communication dated Mar. 3, 2021 issued by European Patent No. 18812837.5.

Hochstrasser, et al., "CasA mediates Cas3-catalyzed target degradation during CRISPR RNA-guided interference" Proceedings of the National Academy of Sciences, vol. III, No. 18, May 6, 2014, pp. 6618-6623.

Westra et al., "CRISPR Immunity Relies on the Consecutive Binding and Degradation of Negatively Supercoiled Invader DNA by Cascade and Cas3" Molecular Cell, vol. 46, No. 5, Jun. 1, 2012, pp. 595-605.

Gong, et al., "Molecular insights into DNA interference by CRISPR-associated nudease-helicase Cas3" Proceedings of the National Academy of Sciences, vol. 111, No. 46, Nov. 3, 2014, pp. 16359-16364.

Jore et al., "Structural basis for CRISPR RNA-guided DNA recognition by Cascade" Nature Structural & Molecular Biology, vol. 18, No. 5, May 1, 2011, pp. 529-536.

Huo et al., "Structures of CRISPR Cas3 offer mechanistic insights into Cascade-activated DNA unwinding and degradation", Nat. Struct. Mol. Biol. 21:771-777, 2014 (Year: 2014).

Hsu et al., Development and Applications of CRISPR-Cas9 for Genome Engineering. Cell (2014), 157: 1262 (Year: 2014).

Bindal et al., Type I-E CRISPR-Cas System as a Defense System in *Saccharomyces cerevisiae*. MSphere (2022); 7(3): 1-9 (Year: 2022).

Pyne et al., Harnessing heterologous and endogenous CRISPR-Cas machineries for efficient markerless genome editing in Clostridium Scientific Reports (2016), 6:25666 | DOI: 10.1038/srep25666 (Year: 2016).

Nelson et al., In vivo genome editing improves muscle function in a mouse model of Duchenne muscular dystrophy. Science (2016), 351: 403-407 and Supplemental material (Year: 2016).

Morisaka et al., Genome editing in mammalian cells by cascade and Cas3. Journal of Investigative Dermatology (2017), vol. 137; Abstract 490 (Year: 2017).

Makarova et al., Evolutionary classification of CRISPR-Cas systems: a burst of class 2 and derived variants. Nature Reviews Microbiology (2020), 18: 67-83; p. 71, H6 (Year: 2020).

Hochstrasser et al., DNA Targeting by a Minimal CRISPR RNA-Guided Cascade, Mol. Cell (2016), 63: 840-851; Fig 6A (Year: 2016).

Tan et al., Cas11 enables genome engineering in human cells with compact CRISPR-Cas3 systems. Mol Cell (2022), 82: 852-867 (Year: 2022).

Van der Oost et al., Unravelling the structural and mechanistic basis of CRISPR-Cas systems. Nature Reviews Microbiology (2014) 12: 479-492 (Year: 2014).

Chunyi Hu, et al., "Reconstitution and biochemical characterization of the RNA-guided helicase-nuclease protein Cas3 from type I-A CRISPR-Cas system", Methods in Enzymology, 2022, vol. 673, pp. 405-424 (20 pages total).

Moumita Ray, et al., "Quantitative tracking of protein trafficking to the nucleus using cytosolic protein-delivery by nanoparticle-stabilized nanocapsules", Bioconjug Chem., Jun. 17, 2015, vol. 26, No. 6, pp. 1004-1007 (6 pages total).

\* cited by examiner

FIG. 3A
CLONE 1 ccacttggaggggtgaggtgagaggattgcttgagcccgggatggtccaggctgcagtg
agccatgatcgtgcca<u>ctgcactccagcctgggcgacagagtgagaccctgtctcacaa
caacaacaacaacaaaaaggctgagctgcaccatgcttgacccagtttcttaaaatt
gttgtcaaagcttcattcactccatggtgctatagagcacaagattttatttggtgagatggtg
ctttcatgaattccccaacagagccaagctctccatctagtggacagggaagctagcag
caaaccttcccttcactacaaaacttcattgcttggccaaaagagagttaattcaatgtag
acatctatgtaggcaattaaaaacctattgatgtataaaacagtttgcattcatggagggca
actaaatacattctaggactttataaaagatcacttttatttatgcaca</u>gGGTGGAACA
AGATGGATTATCAAGTGTC**AAGTCCAATCTATGACATCAATTA
TTATACATCGG**AGCCCTGCCAAAAATCAATGTGAAGCAAATC
GCAGCCCGCCTCCTGCCTCCGCTCTACTCACTGGTGTTCATC
TTTGGTTTTGTGGGCAACATGCTGGTCATCCTCATCCTGATAA
ACTGCAAAGGCTGAAGAGCATGACTGACATCTACCTGCTCA
ACCTGGCCATCTCTGACCTGTTTTTCCTTCTTACTGTCCCCTT
CTGGGCTCACTATGCTGCCGCCAGTGGGACTTTGGAAATAC
AATGTGTCAACTCTTGACAGGGCTCTATTTTATAGGCTTCTTCT
CTGGAATCTTCTTCATCATCCTCCTGACAATCGATAGGTACCT
GGCTGTCGTCCATGCTGTGTTTGCTTTAAAAGCCAGGACGGT
CACCTTTGGGGTGGTGACAAGTGTGATCACTTGGGTGGTGG
CTGTGTTTGCGTCTCTCCCAGGAATCATCTTTA □ : 401bp deletion (FOR LAST CA, THERE IS CA IMMEDIATELY
BEFORE DELETION)
— : PAM + target sequence

FIG. 3B

CLONE 2 ccacttggagggggtgaggtgagaggattgcttgagcccgggatggtccaggctgcagtg
agccatgatcgtgccactgcactccagcctgggcgacagagtgagaccctgtctcaca
acaacaacaacaacaaaaaggctgagctgcaccatgcttgacccagtttcttaaa
attgttgtcaaagcttcattcactccatggtgctatagagcacaagattttatttggtgagatg
gtgctttcatgaattcccccaacagagccaagctctccatctagtggacagggaagctag
cagcaaaccttcccttcactacaaaacttcattgcttggccaaaaagagagttaattcaat
gtagacatctatgtaggcaattaaaaaccattgatgtataaaacagtttgcattcatggag
ggcaactaaatacattctaggactttataaaagatcacttttatttatgcacagGGTGG
AACAAGATGGATTATCAAGTGTC**AAGTCCAATCTATGACATC
AATTATTATACATCGG**AGCCCTGCCAAAAATCAATGTGAAG
CAAATCGCAGCCCGCCTCCTGCCTCCGCTCTACTCACTGGT
GTTCATCTTTGGTTTTGTGGGCAACATGCTGGTCATCCTCAT
CCTGATAAACTGCAAAAGGCTGAAGAGCATGACTGACATCTA
CCTGCTCAACCTGGCCATCTCTGACCTGTTTTTCCTTCTTAC
TGTCCCCTTCTGGGCTCACTATGCTGCCGCCAGTGGGACT
TTGGAAATACAATGTGTCAACTCTTGACAGGGCTCTATTTTAT
AGGCTTCTTCTCTGGAATCTTCTTCATCATCCTCCTGACAATC
GATAGGTACCTGGCTGTCGTCCATGCTGTGTTTGCTTTAAAA
GCCAGGACGGTCACCTTTGGGGTGGTGACAAGTGTGATCA
CTTGGGTGGTGGCTGTGTTTGCGTCTCTCCCAGGAATCATC
TTTA ☐ : 341bp deletion (FOR LAST CA, THERE IS CA IMMEDIATELY
BEFORE DELETION)
— : PAM + target sequence

FIG. 3C

CLONE 3 ccacttggaggggtgaggtgagaggattgcttgagcccgggatggtccaggctgcagt
gagccatgatcgtgccactgcactccagcctgggcgacagagtgagaccctgtctcac
aacaacaacaacaacaaaaaggctgagctgcaccatgcttgacccagtttcttaa
aattgttgtcaaagcttcattcactccatggtgctatagagcacaagatttttatttggtgagat
ggtgctttcatgaattcccccaacagagccaagctctccatctagtggacagggaagct
agcagcaaaccttcccttcactacaaaacttcattgcttggccaaaaagagagttaattc
aatgtagacatctatgtaggcaattaaaaaccattgatgtataaaacagtttgcattcatg
gagggcaactaaatacattctaggactttataaaagatcacttttttatttatgcacagGGT
GGAACAAGATGGATTATCAAGTGTC**AAGTCCAATCTATGACA
TCAATTATTATACATCGG**AGCCCTGCTAAAAAAATCAATGTGA
AGCAAATCGCAGCCCGCCTCCTGCCTCCGCTCTACTCACTG
GTGTTCATCTTTGGTTTTGTGGGCAACATGCTGGTCATCCTC
ATCCTGATAAACTGCAAAAGGCTGAAGAGCATGACTGACATC
TACCTGCTCAACCTGGCCATCTCTGACCTGTTTTTCCTTCTT
ACTGTCCCTTCTGGGCTCACTATGCTGCCGCCAGTGGGA
CTTTGGAAATACAATGTGTCAACTCTTGACAGGGCTCTATTTT
ATAGGCTTCTTCTCTGGAATCTTCTTCATCATCCTCCTGACAA
TCGATAGGTACCTGGCTGTCGTCCATGCTGTGTTTGCTTTAA
AAGCCAGGACGGTCACCTTTGGGGTGGTGACAAGTGTGAT
CACTTGGGTGGTGGCTGTGTTTGCGTCTCTCCAGGAATCA
TCTTTA ☐ : 268bp deletion (NO HOMOLOGY BEFORE AND AFTER DEL)
— : PAM + target sequence
= : C>TA WAVEFORM OF SEQ IS CLEAR

FIG. 3D

CLONE 4 ccacttggaggggtgaggtgagaggattgcttgagcccgggatggtccaggctgcagt
ga|gccatgatcgtgccactgcactccagcctgggcgacagagtgagaccctgtctcac
aacaacaacaacaacaaaaaggctgagctgcaccatgcttgacccagtttctta
aaattgttgtcaaagcttcattcactccatggtgctatagagcacaagattttatttggtgag
atggtgctttcatgaattcccccaacagagccaagctctccatctagtggacagggaag
ctagcagcaaaccttcccttcactacaaaacttcattgcttggccaaaaagagagttaat
tcaatgtagacatctatgtaggcaattaaaaaccattgatgtataaaa|cagtttgcattca
tggagggcaactaaatacattctaggactttataaaagatcacttttatttatgcacagG
TGGAACAAGATGGATTATCAAGTGT<u>**CAAGTCCAATCTATG
ACATCAATTATTATACATCGG**</u>AGCCCTGCCAAAAAATCAATG
TGAAGCAAATCGCAGCCCGCCTCCTGCCTCCGCTCTACTCA
CTGGTGTTCATCTTTGGTTTTGTGGGCAACATGCTGGTCAT
CCTCATCCTGATAAACTGCAAAAGGCTGAAGAGCATGACTG
ACATCTACCTGCTCAACCTGGCCATCTCTGACCTGTTTTCC
TTCTTACTGTCCCCTTCTGGGCTCACTATGCTGCCGCCCAG
TGGGACTTTGGAAATACAATGTGTCAACTCTTGACAGGGCT
CTATTTTATAGGCTTCTTCTCTGGAATCTTCTTCATCATCCTC
CTGACAATCGATAGGTACCTGGCTGTCGTCCATGCTGTGTT
TGCTTTAAAAGCCAGGACGGTCACCTTTGGGGTGGTGACA
AGTGTGATCACTTGGGTGGTGGCTGTGTTTGCGTCTCTCCC
AGGAATCATCTTTA ☐ : 344bp deletion ((NO HOMOLOGY BEFORE AND AFTER DEL)
DELETED SEQUENCE HAS BEEN REPLACED WITH CATCTACAT
— : PAM + target sequence

FIG. 5B

CCAGGCTTTGGGGAGGCCTGGAGTCATGGCCCCACAGGGCTTGAAGCC
CGGGGCCGCCATTGACAGAGGGACAAGCAATGGGCTGGCTGAGGCCTG
GGACCACTTGGCCTTCTCCTCGGAGAGCCTGCCTGCCTGGGCGGGCCC
GCCCGCCACCGCAGCCTCCCAGCTGCTCTCCGTGTCTCCAATCTCCCTT
TTGTTTTGATGCATTTCTGTTTTAATTTATTTTCCAGGCACCACTGTAGTTTA
GTGATCCCAGTGTCCCCCTTCCCTATGGGAATAATAAAGTCTCTCTCTT
AATGACACGGGCATCCAGCTCCAGCCCCAGAGCCTGGGGTGGTAGATTC
CGGCTCTGAGGGCCAGTGGGGGCTGGTAGAGCAAACGCGTTCAGGGCC
TGGGAGCCTGGGGTGGGGTACTGGTGGAGGGGGTCAAGGGTAATTCATT
AACTCCTCTCTTTTGTTGGGGGACCCTGGTCTCTACCTCCAGCTCCACAG
CAGGAGAAACAGGCTAGACATAGGGAAGGGCCATCCTGTATCTTGAGG

GAGGACAGGCCCAGGTCTTTCTTAACGTATTGAGAGGTGGGAATCAGGC
CCAGGTAGTTCAATGGGAGAGGGAGAGTGCTTCCCTCTGCCTAGAGACT
CTGGTGGCTTCTCCAGTTGAGGAGAAACCAGAGGAAAGGGGAGGATTGG
GGTCTGGGGAGGGAACACCATTCACAAAGGCTGACGGTTCCAGTCCGA
AGT

FIG. 6A
CLONE 1

GGGCTTCTCCTGACTGTTCCTTGTGTGACCTGTTCCCACATCTGGATG
GGCTGCAGGAGCCAGTGCTGTGGGGACAGAAGGTCTGGAGCTGCCC
GTGAAGGGCAGAATGCTGCCCTCAGACCGCTTCCTCCCTGTCCTTG
TCTGTCCAAGGAGAATGAGGTCTCACTGGTGGATTTCGGACTACCCTG
AGGAGCTGGCACCTGAGGGACAAGGCCCCCACCTGCCCAGCTCCA
GCCTCTGATGAGGGGTGGGAGAGAGCTACATGAGGTTGCTAAGAAAG
CCTCCCTGAAGGAGACCACACAGTGTGTGAGGTTGGAGTCTCTAGC
AGCGGGTTCTGTGCCCCAGGGATAGTCTGGCTGTCCAGGCACTGCT
CTTGATATAAACACCACCTCCTAGTTATGAAACCATGCCCATTCTGCCTC
TCTGTATGGAAAGAGCATGGGGCTGGCCCGTGGGGTGGTGTCCACT
TTAGGCCCTGTGGGAGATCATGGGAACCCACGCAGTGGGTCATAGGC
TCTCTCATTTACTACTCACATCCACTCTGTGAAGAAGCGATTATGATCTC
TCCTCTAGAAACTCGTAGAGTCCCATGTCTGCCGGCTTCCAGAGCCTG
CACTCCTCCACCTTGGCTTGGCTTTGCTGGGGCTAGAGGAGCTAGGA
TGCACAGCAGCTCTGTGACCCTTTGTTTGAGAGGAACAGGAAAACCA
CCCTTCTCTCTGGCCCACTGTGTCCTCTTCCTGCCCTGCCATCCCTT
CTGTGAATGTTAGACCCATGGGAGCAGCTGGTCAGAGGGGACCCCGG
CCTGGGGCCCCTAACCCTATGTAGCCTCAGTCTTCCCATCAGGCTCTC
AGCTCAGCCTGAGTGTTGAGGCCCAGTGGCTGCTCTGGGGCCTC
CTGAGTTTCTCATCTGTGCCCCTCCCTCCCTGGCCCAGGTGAAGGTGT
GGTTCCAGAACCGGAGGACAAAGTACAAACGGCAGAAGCTGGAGGA
GGAAGGGCCTGAGTCCGAGCAGAAGAAGAAGGGCTCCCATCACATCA
ACCGGTGGCGCATTGCCACGAAGCAGGCCAATGGGGAGGACATCGAT
GTCACCTCCAATGACTAGGGTGGGCAACCACAAACCCACGAGGGCAG
AGTGCTGCTTGCTGCTGGCCAGGCCCTGCGTGGGCCCAAGCTGGA
CTCTGGCCACTCCCTGGCCAGGCTTTGGGGAGGCCTGGAGTCATGG
CCCCACAGGGCTTGAAGCCCGGGGCCGCCATTGACAGAGGGACAAG
CAATGGGCTGGCTGAGGCCTGGGACCACTTGGCCTTCTCCTCGGAGA
GCCTGCCTGCCTGGGCGGGCCCGCCCGCCACCGCAGCCTCCCAGCT
GCTCTCCGTGTCTCCAATCTCCCTTTTGTTTTGATGCATTTCTGTTTTAA
TTTATTTTCCAGGCACCACTGTAGTTTAGTGATCCCCAGTGTCCCCCTT
CCCTATGGGAATAATAAAGTCTCTCTTAATGACACGGGCATCCAGC
TCCAGCCCCAGAGCCTGGGGTGGTAGATTCCGGCTCTGAGGGCCAGT
GGGGGCTGGTAGAGCAAACGCGTTCAGGGCCTGGGAGCCTGGGGTG
GGGTACTGGTGGAGGGGGTCAAGGGTAATTCATTAACTCCTCTCTTTT
GTTGGGGGACCCTGGTCTCTACCTCCAGCTCCACAGCAGGAGAAACA
GGCTAGACATAGGGAAGGGCCATCCTG

☐ : 513bp, 363bp del  micro homology: CTC, T
— : PAM + target sequence

FIG. 6B
CLONE 2

```
GGGCTTCTCCTGACTGTTCCTTGTGTGACCTGTTCCCACATCTGGATG
GGCTGCAGGAGCCAGTGCTGTGGGGACAGAAGGTCTGGAGCTGCCC
GTGAAGGGCAGAATGCTGCCCTCAGACCCGCTTCCTCCCTGTCCTTG
TCTGTCCAAGGAGAATGAGGTCTCACTGGTGGATTTCGGACTACCCTG
AGGAGCTGGCACCTGAGGGACAAGGCCCCCACCTGCCCAGCTCCA
GCCTCTGATGAGGGGTGGGAGAGAGCTACATGAGGTTGCTAAGAAAG
CCTCCCTGAAGGAGACCACACAGTGTGTGAGGTTGGAGTCTCTAGC
AGCGGGTTCTGTGCCCCAGGGATAGTCTGGCTGTCCAGGCACTGCT
CTTGATATAAACACCACCTCCTAGTTATGAAACCATGCCCATTCTGCCTC
TCTGTATGGAAAGAGCATGGGGCTGGCCCGTGGGGTGGTGTCCACT
TTAGGCCCTGTGGGAGATCATGGGAACCCACGCAGTGGGTCATAGGC
TCTCTCATTTACTACTCACATCCACTCTGTGAAGAAGCGATTATGATCTC
TCCTCTAGAAACTCGTAGAGTCCCATGTCTGCCGGCTTCCAGAGCCTG
CACTCCTCCACCTTGGCTTGGCTTTGCTGGGGCTAGAGGAGCTAGGA
TGCACAGCAGCTCTGTGACCCTTTGTTTGAGAGGAACAGGAAAACCA
CCCTTCTCTCTGGCCCACTGTGTCCTCTTCCTGCCCTGCCATCCCCTT
CTGTGAATGTTAGACCCATGGGAGCAGCTGGTCAGAGGGGACCCCGG
CCTGGGGCCCCTAACCCTATGTAGCCTCAGTCTTCCCATCAGGCTCTC
AGCTCAGCCTGAGTGTTGAGGCCCAGTGGCTGCTCTGGGGCCTC
CTGAGTTTCTCATCTGTGCCCCTCCCTCCCTGGCCCAGGTGAAGGTGT
GGTTCCAGAACCGGAGGACAAAGTACAAACGGCAGAAGCTGGAGGA
GGAAGGGCCTGAGTCCGAGCAGAAGAAGAAGGGCTCCCATCACATCA
ACCGGTGGCGCATTGCCACGAAGCAGGCCAATGGGGAGGACATCGAT
GTCACCTCCAATGACTAGGGTGGGCAACCACAAACCCACGAGGGCAG
AGTGCTGCTTGCTGCTGGCCAGGCCCTGCGTGGGCCCAAGCTGGA
CTCTGGCCACTCCCTGGCCAGGCTTTGGGGAGGCCTGGAGTCATGG
CCCCACAGGGCTTGAAGCCCGGGGCCGCCATTGACAGAGGGACAAG
CAATGGGCTGGCTGAGGCCTGGGACCACTTGGCCTTCTCCTCGGAGA
GCCTGCCTGCCTGGGCGGGCCCGCCCGCCACCGCAGCCTCCCAGCT
GCTCTCCGTGTCTCCAATCTCCCTTTTGTTTTGATGCATTTCTGTTTTAA
TTTATTTTCCAGGCACCACTGTAGTTTAGTGATCCCCAGTGTCCCCCTT
CCCTATGGGAATAATAAAGTCTCTCTCTTAATGACACGGGCATCCAGC
TCCAGCCCCAGAGCCTGGGGTGGTAGATTCCGGCTCTGAGGGCCAGT
GGGGGCTGGTAGAGCAAACGCGTTCAGGGCCTGGGAGCCTGGGGTG
GGGTACTGGTGGAGGGGGTCAAGGGTAATTCATTAACTCCTCTCTTTT
GTTGGGGGACCCTGGTCTCTACCTCCAGCTCCACAGCAGGAGAAACA
GGCTAGACATAGGGAAGGGCCATCCTG
```

☐ : 694bp del micro homology: -
— : PAM + target sequence

Fig. 10A

PRE-crRNA (LRSR) : TGGATGTGTTGTTTGTGTGATACTATAAAGTTGGT
AGATTGTGACTGGCTTAAAAAATCATTAATTAATAATAGGTTATGTTTAG
A|GTGTTCCCCGCGCCAGCGGGGATAAACCG|CAGGCCAATGGGGAGG
ACATCGATGTCACCTC|GTGTTCCCCGCGCCAGCGGGGATAAACCG (SEQ ID NO: 71)

PRE-crRNA (RSR) : GTGTTCCCCGCGCCAGCGGGGATAAACCG|CAGGC
CAATGGGGAGGACATCGATGTCACCTC|GTGTTCCCCGCGCCAGCGGG
GATAAACCG (SEQ ID NO: 72)

MATURE crRNA : ATAAACCG|CAGGCCAATGGGGAGGACATCGATGTCACCT
C|GTGTTCCCCGCGCCAGCGGGG (SEQ ID NO: 73)

FIG. 16

| Emx1 | | 1.7 Kbp |
|---|---|---|
| WT | TGC/ TCACATCAACCGGTGGCGCATTGCCACG AAGCAG/ CTT | SEQ ID NO:75 |
| #3 | TGC/ CTGCC ----(-1447bp)---- CTACC/ CTT | SEQ ID NO:76 |
| #5 | TGC/ GCCCA ----(-1370bp)---- CCTGG/ CTT | SEQ ID NO:77 |
| #6 | TGC/ GAGCT ----(-797bp)---- GAGGA/ CG AAGCAG/ CTT | SEQ ID NO:78 |
| #19 | TGC/ ACCCT ----(-994bp)---- CAGCT/ CTT | SEQ ID NO:79 |
| #27 | TGC/ GCCCA ----(-1370bp)---- CCTGG/ CTT | SEQ ID NO:80 |
| #33 | TGC/ TGAGG ----(-690bp)---- TCTCA/ CG AAGCAG/ CTT | SEQ ID NO:81 |
| #38 | TGC/ GGACT ----(-690bp)---- AGGCC/ CG AAGCAG/ CTT | SEQ ID NO:82 |
| #41 | TGC/ GGACT ----(-834bp)---- AAGAA/ CG AAGCAG/ CTT |  |
| #93 | TGC/ TGATG ----(-820bp)---- CAGGCCAATGGG/ CTT | SEQ ID NO:83 |

SEQUENCE LISTING

```
Sequence total quantity: 83
SEQ ID NO: 1            moltype = DNA  length = 2685
FEATURE                 Location/Qualifiers
misc_feature            1..2685
                        note = Synthetic sequence, modified Cas3 with NLS
source                  1..2685
                        mol_type = other DNA
                        organism = synthetic construct
SEQUENCE: 1
atgcccaaga agaagcggaa ggtggaacct tttaaatata tatgccatta ctggggaaaa   60
tcctcaaaaa gcttgacgaa aggaaatgat attcatctgt taatttatca ttgccttgat  120
gttgctgctg ttgcagattg ctggtgggat caatcagtcg tactgcaaaa tacttttttgc 180
cgaaatgaaa tgctatcaaa acagagggtg aaggcctggc tgttattttt cattgctctt  240
catgatattg gaaagtttga tatacgattc caatataaat cagcagaaag ttggctgaaa  300
ttaaatcctg caacgccatc acttaatggt ccatcaacac aaatgtgccg taaatttaat  360
catggtgcag ccggtctgta ttggtttaac caggattcac tttcagagca atctctcggg  420
gatttttca gtttttttga tgccgctcct catccttatg agtcctggtt tccatgggta  480
gaggccgtta caggacatca tggttttata ttacattccc aggatcaaga taagtcgcgt  540
tgggaaatgc cagcttctct ggcatcttat gctgcgcaag ataaacaggc tcgtgaggag  600
tggatatctg tactggaagc attatttta acgccagcgg ggttatctat aaacgatata  660
ccacctgatt gttcatcact gttagcaggt ttttgctcgc ttgctgactg gttaggctcc  720
tggactacaa cgaataccgtt tctgtttaat gaggatgcgc cttccgacat aaatgctctg  780
agaacgtatt tccaggaccg acagcaggat gcgagccggg tattggagtt gagtggactt  840
gtatcaaata agcgatgtta tgaaggtgtt catgcactac tggacaatgg ctatcaaccc  900
agacaattac aggtgttagt tgatgctctt ccagtagctc ccgggctgac ggtaatagag  960
gcacctacag gctccggtaa aacggaaaca gcgctgacct atgcttggaa acttattgat 1020
caacaaattg cggatagtgt tattttttgcc ctcccaacac aagctaccgc gaatgctatg 1080
cttacgagaa tggaagcgag cgcgagccac ttattttcat ccccaaatct tattcttgct 1140
catggcaatt cacggtttaa ccacctctttt caatcaataa aatcacgcgc gattactgaa 1200
caggggcaag aagaagcgtg ggttcagtgt tgtcagtggt tgtcacaaag caataagaaa 1260
gtgtttcttg ggcaaatcgg cgtttgcacg attgatcagg tgttgatatc ggtattgcca 1320
gttaaacacc gctttatccg tggtttggga attggtcgaa gtgtttttaat tgttgatgaa 1380
gttcatgctt acgacaccta tatgaacggc ttgctggagg cagtgctcaa ggctcaggct 1440
gatgtgggag ggagtgttat tcttctttcc gcaaccctac caatgaaaca aaaacagaaa 1500
cttctggata cttatggtct gcatacagat ccagtggaaa ataactccgc atatccactc 1560
attaactggc gaggtgtgaa tggtgcgcaa cgtttttgatc tgctagctca tccagaacaa 1620
ctcccgcccc gcttttcgat tcagccagaa cctatttgtt tagctgacat gttacctgac 1680
cttacgatgt tagagcgaat gatcgcagcg gcaaacgcgg gtgcacaggt ctgtcttatt 1740
tgcaatttgg ttgacgttgc acaagtatgc taccaacggc taaaggagct aaataacacg 1800
caagtagata tagatttgtt tcatgcgcgc tttacgctga acgatcgtcg tgaaaaagag 1860
aatcgagtta ttagcaattt cggcaaaaat gggaagcgaa atgttggacg gatacttgtc 1920
gcaacccagg tcgtggaaca atcactcgac gttgattttg attggttaat tactcagcat 1980
tgtcctgcag atttgctttt ccaacgattg ggccgtttac atcgccatca tcgcaaatat 2040
cgtcccgctg gttttgagat tcctgttgcc accattttgc tgcctgatgg cgagggttac 2100
ggacgacatg agcatatta tagcaacgtt agagtcatgt ggcggacgca gcaacatatt 2160
gaggagctta atggagccat cttattttc cctgatgctt accggcaatg gctggatagc 2220
atttacgatg atgcggaaat ggatgagcca gaatgggtcg gcaatggcat ggataaattt 2280
gaaagcgccg agtgtgaaaa aaggttcaag gctcgcaagg tcctgcagtg ggctgaagaa 2340
tatagcttgc aggataacga tgaaaccatt cttgcggtaa cgagggatgg ggaaatgagc 2400
ctgccattat tgccttatgt acaaacgtct tcaggtaaac aactgctcga tggccaggtc 2460
tacgaggacc taagtcatga acagcagtat gaggcgcttg cacttaatcg cgtcaatgta 2520
```

```
cccttcacct ggaaacgtag tttttctgaa gtagtagatg aagatgggtt acttTggctg   2580
gaagggaaac agaatctgga tggatgggtc tggcagggta acagtattgt tattacctat   2640
acaggggatg aagggatgac cagagtcatc cctgcaaatc ccaaa                  2685

SEQ ID NO: 2              moltype = DNA   length = 1527
FEATURE                   Location/Qualifiers
misc_feature              1..1527
                          note = Synthetic sequence, modified Cse1 with NLS
source                    1..1527
                          mol_type = other DNA
                          organism = synthetic construct
SEQUENCE: 2
atgcccaaga agaagcggaa ggtgaacctg ctgattgaca actggatccc tgtgcgccca   60
cggaacggag gaaaagtcca gattattaat ctgcagagcc tgtactgctc ccgggatcag   120
tggagactga gcctgcccag agacgatatg gagctggccg ccctggccct gctggtgtgc   180
atcggcagag tcatcgcccc tgccaaggac gatgtggagt tcaggcaccg catcatgaac   240
cctctgaccg aggatgagtt tcagcagctg atcgccccat ggatcgacat gttctatctg   300
aatcgacccg agcacccctt catgcagaca aagggcgtga aggccaacga cgtgacccac   360
atggagaagc tgctggcagg cgtgtccgga gcaacaaatt gcgccttcgt gaaccagcca   420
ggacaggaga aggccctgtg cggaggctgt accgccatcg ccctgtttaa tcaggcaaac   480
caggcacctg gattcggagg aggctttaag tctggactga ggggaggaac cccagtgacc   540
acattcgtga gaggcatcga tctgaggagc acagtgctgc tgaatgtgct gaccctgcca   600
cggctgcaga agcagtttcc caatgagagc cacacagaga accagccac ctggatcaag   660
cctatcaagt ctaacgagag catccctgcc agctccatcg gcttcgtgag aggcctgttt   720
tggcagccca cccacatcga gctgtgcgac ccatcggca tcggcaagtg ttcttgctgt   780
ggccaggaaa gcaatctgag gtacaccgga ttcctgaagg agaagttcac ctttacagtg   840
aacggcctgt ggccccaccc tcactctcca tgtctggtga cagtgaagaa gggcgaggtg   900
gaggagaagt tcctggcctt taccacatcc gcccctcttg gaccagat cagcagagtg   960
gtggtggaca agatcatcca gaacgagaat ggcaacagag tggccgccgt ggtgaatcag   1020
ttcaggaaca tcgccccaca gtctccctg gagctgatca tgggcggcta caggaacaat   1080
caggccagca tcctggagcg gagacacgat gtgctgatgt taatcagg ctggcagcag   1140
tatggcaatg tgatcaacga gatcgtgaca gtgggcctgg gctacaagac cgccctgaga   1200
aaggccctgt atacattcgc cgagggcttt aagaacaagg acttcaaggg agcaggcgtg   1260
agcgtgcacg agaccgccga gaggcactt taccgccagt ccgagctgct gatccccgat   1320
gtgctggcca atgtgaactt ctcccaggcc gacgaagtga tcgccgatct gagggacaag   1380
ctgaccagc tgtgcgagat gctgtttaac cagtctgtgg ccccatacgc caccaccccc   1440
aagctgatca gcacactggc cctggcaagg gccaccctgt ataagcacct gagggagctg   1500
aagccacagg gaggacctt taatgga                                       1527

SEQ ID NO: 3              moltype = DNA   length = 501
FEATURE                   Location/Qualifiers
misc_feature              1..501
                          note = Synthetic sequence, modified Cse2 with NLS
source                    1..501
                          mol_type = other DNA
                          organism = synthetic construct
SEQUENCE: 3
atgcccaaga agaagcggaa ggtggccgat gagatcgacg caatggcact gtacagggca   60
tggcagcagc tggacaacgg atcttgcgca cagatcaggc gcgtgagcga gcctgatgag   120
ctgagggaca tcccagcctt ctatcggctg gtgcagcccc ttggctggga gaatcctaga   180
caccaggacc ccctgctgag gatggtgttt tgtctgagcc ccggcaagaa cgtgatccgg   240
caccaggaca agaagagcga gcagaccaca ggaatctccc tgggacgcgc cctggccaat   300
tccggccgga tcaacgagcg gagaatcttc cagctgatca gggccgatcg cacagccgac   360
atggtgcagc tgaggcgcct gctgacccac gcagagcctg tgctggattg ccactgatg   420
gcccgcatgc tgacatggtg gggcaagcgg gagagacagc agctgctgga ggacttcgtg   480
ctgaccacaa ataagaacgc c                                            501

SEQ ID NO: 4              moltype = DNA   length = 693
FEATURE                   Location/Qualifiers
misc_feature              1..693
                          note = Synthetic sequence, modified Cas5 with NLS
source                    1..693
                          mol_type = other DNA
                          organism = synthetic construct
SEQUENCE: 4
atgcccaaga agaagcggaa ggtgcgctcc tacctgatcc tgagactggc aggaccaatg   60
caggcatggg gacagcctac attcgaggga ccaggccaa caggccgctt tcctacccgg   120
tctggactgc tgggactgct gggagcctgc ctgggcatcc agaggacga tacctctagc   180
ctgcaggccc tgagcgagtc cgtgcagttc ccgtgcagtc gtgatgagct gatcctagc   240
gataggcgcg tgtccgtgac aggcctgcgg gattaccaca ccgtgctggg cgccagagag   300
gactataggg gcctgaagtc ccacgagacc atccagacat ggcgcgagta cctgtgcgac   360
gcctcttta cagtggccct gtggctgacc ccacacgcaa caatggtcat cagcgagctg   420
gagaaggccg tgctgaagcc acggtacacc cctatctgg gccggagaag ctgccctctg   480
acacacccac tgttcctggg cacctgtcag gcctccgatc ccagaaggc cctgctgaac   540
tacgagcctg tgggcggcga catctattct gaggagagcg tgacaggcca ccacctgaag   600
ttcaccgcca gggatgagcc aatgatcaca ctgccaaggc agtttgcatc cagggagtgg   660
tatgtgatca agggaggaat ggacgtgagc cag                              693

SEQ ID NO: 5              moltype = DNA   length = 618
```

```
FEATURE              Location/Qualifiers
misc_feature         1..618
                     note = Synthetic sequence, modified Cas6 with NLS
source               1..618
                     mol_type = other DNA
                     organism = synthetic construct
SEQUENCE: 5
atgcccaaga agaagcggaa ggtgtacctg agcaaagtga tcatcgcaag ggcatggtcc    60
agggacctgt atcagctgca ccagggcctg tggcacctgt tccctaatag accagatgcc   120
gccagggact tcctgtttca cgtggagaag aggaacacac ccgagggctg tcacgtgctg   180
ctgcagtccg cccagatgcc cgtgagcacc gcagtggcca cagtgatcaa gaccaagcag   240
gtggagttcc agctgcaagt gggcgtgcca ctgtacttta ggctgcgcgc caatcccatc   300
aagaccatcc tggataacca gaagcgcctg gactctaagg caatatcaa gcggtgcaga    360
gtgcctctga tcaaggaggc cgagcagatc gcctggctgc agagaaagct gggcaacgtc   420
gccagggtgg aggatgtgca ccctatcagc gagcggccac agtatttcag cggcgacggc   480
aagtccggca agatccagac cgtgtgcttt gagggcgtgc tgaccatcaa cgatgcccca   540
gccctgatcg acctggtgca gcaggaatc ggacctgcta agtcaatggg atgtgggctg    600
ctgtcactgg cacctctg                                                  618

SEQ ID NO: 6         moltype = DNA  length = 1110
FEATURE              Location/Qualifiers
misc_feature         1..1110
                     note = Synthetic sequence, modified Cas7 with NLS
source               1..1110
                     mol_type = other DNA
                     organism = synthetic construct
SEQUENCE: 6
atgcccaaga agaagcggaa ggtgtccaat ttcatcaaca tccacgtgct gatctcccac    60
tctccaagct gcctgaatag agacgatatg aacatgcaga aggacgccat ctttggcggc   120
aagcggagag tgaggatctc tagccagtcc ctgaagcggg ccatgagaaa gtctgctac    180
tatgccaga atatcggcga gtcctctctg aggaccatcc acctggcaca gctgagggac   240
gtgctgagac agaagctggg cgagcggttt gatcagaaga tcatcgacaa gacactggcc   300
ctgctgagcg gcaagtccgt ggatgaggcc gagaagatca gcgccgacgc agtgacccca   360
tgggtggtgg gagagatcgc atggttctgt gagcaggtgc caaggccga ggcgataat     420
gacgata agaagctgct gaaggtgctg aaggaggata tcgccgccat cagagtgaac     480
ctgcagcagg gagtggacat cgccctgagc ggcaggatgg ccacatccgg catgatgacc   540
gagctgggca aggtggacgg agcaatgtcc atcgcacacg ccatcaccac acaccaggtg   600
gactctgata tcgactggtt cacagccgtg gacgatctgc aggagcaggg aagcgcccac   660
ctgggaaccc aggagttcag ctccggcgtg ttacagat atgccaatat caacctggca   720
cagctgcagg agaacctggg aggagcatcc agggagcagg ccctggagat cgccacacac   780
gtggtgcaca tgctggcaac cgaggtgcca ggagcaaagc agcgcaccta cgccgccttc   840
aatcctgccg atatggtcat ggtgaacttt tccgacatgc cactgtctat ggccaatgcc   900
ttcgagaagg ccgtgaaggc caaggatggc ttcctgcagc cttccatcca ggccttttaa   960
cagtactggg accgcgtggc caatggatat ggcctgaacg gagctgccgc ccagttttcc  1020
ctgtctgatg tggaccctat cacagcccag gtgaagcaga tgccaaccct ggagcagctg  1080
aagagctggg tgcggaacaa tggagaggca                                    1110

SEQ ID NO: 7         moltype = DNA  length = 2775
FEATURE              Location/Qualifiers
misc_feature         1..2775
                     note = Synthetic sequence, modified Cas3 with BPNLS
source               1..2775
                     mol_type = other DNA
                     organism = synthetic construct
SEQUENCE: 7
aagcggactg ctgatggcag tgaatttgag tccccaaaga agaagagaaa ggtggaagaa    60
ccttttaaat atatatgcca ttactgggga aaatcctcaa aaagcttgac gaaaggaaat   120
gatattcatc tgttaattta tcattgcctt gatgttgctg ctgttgcaga ttgctggtgg   180
gatcaatcag tcgtactgca aaatactttt tgccgaaatg aaatgctatc aaaacagagg   240
gtgaaggcct ggctgttatt tttcattgct cttcatgata ttggaaagtt tgatatacga   300
ttccaatata aatcagcaga aagttggctg aaattaaatc ctgcaacgcc atcacttaat   360
ggtccatcaa cacaaatgtg ccgtaaattt aatcatggtg cagccggtct gtattggttt   420
aaccaggatt cactttcaga gcaatctctc ggggattttt tcagtttttt tgatgccgct   480
cctcatcctt atgagtcctg gtttccatgg gtagaggccg ttacaggaca tcatggtttt   540
atattacatt cccaggatca agataagtcg cgttgggaaa tgccagcttc tctggcatct   600
tatgctgcgc aagataaaca ggctcgtgag gagtggatat ctgtactgga agcattattt   660
ttaacgccag cggggttatc tataaacgat ataccacctg attgttcatc actgttagca   720
ggttttttgc tcgcttgctga ctggttaggc tcctggacta caacgaatac ctttctgttt   780
aatgaggatg cgccttccga cataaatgct ctgaaacgtg cataacagag ccgacagcag   840
gatgcgagcc gggtattgga gttgagtgga cttgtatcaa ataagcgatg ttatgaaggt   900
gttcatgcac tactggacaa tggctatcaa cccagacaat tacaggtgtt agttgatgct   960
cttccagtag ctcccgggct gacgtaata gaggcaccta caggctccgg taaaacgaa   1020
acagcgctgg cctatgcttg gaaacttatt gatcaacaaa ttgcggatag tgttattttt  1080
gccctcccaa cacaagctac cgcgaatgct atgcttacga gatgaagc gagcgcgagc  1140
cacttatttt catccccaaa tcttattctt gctcatggca attcacggtt taaccactct  1200
tttcaatcaa taaatcacg cgcgattact gaacagggc aagaagaagc gtgggttcag    1260
tgttgtcagt ggttgtcaca aagcaataag aaagtgttc ttgggcaaat cggcttttgc   1320
acgattgatc aggtgttgat atcggtattg ccagttaaac accgctttat ccgtggtttg  1380
ggaattggtc gaagtgtttt aattgttgat gaagttcatg cttacgacac ctatatgaac  1440
```

```
ggcttgctgg aggcagtgct caaggctcag gctgatgtgg agggagtgt tattcttctt    1500
tccgcaaccc taccaatgaa acaaaaacag aaacttctgg atacttatgg tctgcataca   1560
gatccagtgg aaaataactc cgcatatcca ctcattaact ggcgaggtgt gaatggtgcg   1620
caacgttttg atctgctagc tcatccagaa caactcccgc cccgcttttc gattcagcca   1680
gaacctattt gtttagctga catgttacct gaccttacta tgttagagcg aatgatcgca   1740
gcggcaaacg cgggtgcaca ggtctgtctt atttgcaatt tggttgacgt tgcacaagta   1800
tgctaccaac ggctaaagga gctaaataac acgcaagtag atatagattt gtttcatgcg   1860
cgctttacgc tgaacgatcg tcgtgaaaaa gagaatcgag ttattagcaa tttcggcaaa   1920
aatgggaagc gaaatgttgg acggatactt gtcgcaaccc aggtcgtgga acaatcactc   1980
gacgttgatt ttgattggtt aattactcag cattgtcctg cagatttgct tttccaacga   2040
ttgggccgtt tacatcgcca tcatcgcaaa tatcgtcccg ctggttttga gattcctgtt   2100
gccaccattt tgctgcctga tggcgagggt tacggacgac atgagcatat ttatagcaac   2160
gttagagtca tgtggcggac gcagcaacat attgaggagc ttaatggagc atccttattt   2220
ttccctgatg cttaccggca atggctggat agcatttacg atgatgcgga aatggatgag   2280
ccagaatggg tcggcaatgg catgataaa tttgaaagcg ccgagtgtga aaaaaggttc    2340
aaggctcgca aggtcctgca gtgggctgaa gaatatagct tgcaggataa cgatgaaacc   2400
attcttgcgt aacgaggga tggggaaatg agcctgccat tattgcctta tgtacaaacg    2460
tcttcaggta aacaactgct cgatggccag gtctacgagg acctaagtca tgaacagcag   2520
tatgaggcgc ttgcacttaa tcgcgtcaat gtaccttca cctggaaacg tagtttttct    2580
gaagtagtag atgaacgatgg gttactttgg ctggaaggga aacagaatct ggatggatga   2640
gtctggcagg gtaacagtat tgttattacc tatacagggg atgaagggat gaccagagtc   2700
atccctgcaa atcccaaaaa gcggactgct gatggcagtg aatttgagtc cccaaagaag   2760
aagagaaagg tggaa                                                    2775

SEQ ID NO: 8            moltype = DNA  length = 1617
FEATURE                 Location/Qualifiers
misc_feature            1..1617
                        note = Synthetic sequence, modified Cse1 with BPNLS
source                  1..1617
                        mol_type = other DNA
                        organism = synthetic construct
SEQUENCE: 8
aagcggactg ctgatggcag tgaatttgag tccccaaaga agaagagaaa ggtggaaaac    60
ctgctgattg acaactggat ccctgtgcgc ccacggaacg gaggaaaagt ccagattatt    120
aatctgcaga gcctgtactg ctcccgggat cagtggagac tgagcctgcc cagagacgat    180
atggagctgg ccgccctggc cctgctggtg tgcatcggcc agatcatcgc ccctgccaag    240
gacgatgtgg agttcaggca ccgcatcatg aaccctctga ccgaggatga gtttcagcag   300
ctgatcgccc atggatcga catgttctat ctgaatcacg ccgagcaccc cttcatgcag    360
acaaagggcg tgaaggccaa cgacgtgacc cccatggaga agctgctggc aggcgtgtcc   420
ggagcaacaa attgcgcctt cgtgaaccag ccaggacagg agaggccct gtgcggaggc    480
tgtaccgcca tcgccctgtt taatcaggca accaggcac ctggattcgg aggaggctt    540
aagtctggac tgagggagg aaccccagtg accacattcg tgagaggcat cgatctgagg   600
agcacagtgc tgctgaatgt gctgaccctg ccacggctgc agaagcagtt tccaatgag   660
agccacacag agaaccagcc cacctggatc aagcctatca gtctaacga gagcatccct    720
gccagctcca tcggcttcgt gagaggcctg tttttggcagc cagcccacat cgagctgtgc   780
gaccccatcg gcatcggcaa gtgttcttgc tgtggcagg aaagcaatct gaggtacacc   840
ggcttcctga aggagaagtt cacctttaca gtgaacgcc tgtggcccca ccctcactct   900
ccatgtctgg tgacagtgaa gaagggcgag gtggaggaga gttcctggc ctttaccaca   960
tccgcccct cttggaccca gatcagcaga gtggtggtgg acaagatcat ccagaacgag   1020
aatggcaaca gagtggccgc cgtggtgaat cagttcagga catcgcccc acagtctccc   1080
ctggactga tcatgggcgg ctacaggaac aatcaggcca gcatcctgga gcggagacac   1140
gatgtgctga tgtttaatca gggctggcag cagtatggca atgtgatcaa cgagatcgtg   1200
acagtgggcc tgggctacaa gaccgccctg agaaaggccc tgtatacatt cgccgagggc   1260
tttaagaaca aggacttcaa gggagcaggc gtgagcgtgc acgagaccgc cgagaggcac   1320
ttttaccgcc agtccgagct gctgatcccc gatgtgctga ccaatgtgaa cttctcccag   1380
gccgacgaag tgatcgccga tctgagggac aagctgcacc agctgtgcga gatgctgttt   1440
aaccagtctg tggcccata cgccaccac cccaagctga tcagcacact ggccctggca    1500
agggccaccc tgtataagca cctgagggag ctgaagccac agggaggacc ttctaatgga   1560
aagcggactg ctgatggcag tgaatttgag tccccaaaga agaagagaaa ggtggaa       1617

SEQ ID NO: 9            moltype = DNA  length = 591
FEATURE                 Location/Qualifiers
misc_feature            1..591
                        note = Synthetic sequence, modified Cse2 with BPNLS
source                  1..591
                        mol_type = other DNA
                        organism = synthetic construct
SEQUENCE: 9
aagcggactg ctgatggcag tgaatttgag tccccaaaga agaagagaaa ggtggaagcc    60
gatgagatcg acgcaatggc actgtacagg gcatggcagc agctggacaa cggatcttgc   120
gcacagatca ggcgcgtgag cgagcctgat gagctgaggg acatcccagc cttctatcgg   180
ctggtgcagc cctttggctg ggagaatcct agacaccagc aggccctgct gaggatggtg   240
ttttgtctga gcgccggcaa gaacgtgatc cggcaccagg acaagaagag cgagcagacc   300
acaggaatct cctgggacg cgccctggcc aattccagca ggatcaacga gcggagaatc   360
ttccagctga tcagggccga tcgcacagcc gacatggtgc agctgaggcg cctgctgacc   420
cacgcagagc ctgtgctgga ttggccactg atggcccgca tgctgacatg gtggggcaag   480
cgggagagac agcagctgct ggaggacttc gtgctgacca caaataagaa cgccaagcgg   540
actgctgatg gcagtgaatt tgagtcccca agaagaaga gaaaggtgga a               591
```

| SEQ ID NO: 10 | moltype = DNA   length = 783 |
|---|---|
| FEATURE | Location/Qualifiers |
| misc_feature | 1..783 |
| | note = Synthetic sequence, modified Cas5 with BPNLS |
| source | 1..783 |
| | mol_type = other DNA |
| | organism = synthetic construct |

SEQUENCE: 10

```
aagcggactg ctgatggcag tgaatttgag tccccaaaga agaagagaaa ggtggaacgc   60
tcctacctga tcctgagact ggcaggacca atgcaggcat ggggacagcc tacattcgag  120
ggaaccaggc caacaggccg ctttcctacc cggtctggac tgctgggact gctgggagcc  180
tgcctgggca tccagaggga cgatacctct agcctgcagg ccctgagcga gtccgtgcag  240
ttcgccgtgc gctgtgatga gctgatcctg acgataggc gcgtgtccgt gacaggcctg  300
cgggattacc acaccgtgct gggcgccaga gaggactata gtcccacgag  360
accatccaga catggcgcga gtacctgtgc gacgcctctt ttacagtggc cctgtggctg  420
accccacacg caacaatggt catcagcgag ctggagaagg ccgtgctgaa gccacggtac  480
acccctatc tgggccggag aagctgccct ctgacacacc cactgttcct gggcacctgt  540
caggcctccg atccccagaa ggccctgctg aactacgagc ctgtgggcgg cgacatctat  600
tctgaggaga gcgtgacagg ccaccacctg aagttcaccg ccaggatga gccaatgatc  660
acactgccaa ggcagtttgc atccaggag tggtatgtga tcaagggagg aatgacgtg   720
agccagaagc ggactgctga tggcagtgaa tttgagtccc caagaagaa gagaaaggtg  780
gaa                                                                783
```

| SEQ ID NO: 11 | moltype = DNA   length = 708 |
|---|---|
| FEATURE | Location/Qualifiers |
| misc_feature | 1..708 |
| | note = Synthetic sequence, modified Cas6 with BPNLS |
| source | 1..708 |
| | mol_type = other DNA |
| | organism = synthetic construct |

SEQUENCE: 11

```
aagcggactg ctgatggcag tgaatttgag tccccaaaga agaagagaaa ggtggaatac   60
ctgagcaaag tgatcatcgc aagggcatgg tccaggacc tgtatcagct gcaccagggc  120
ctgtggcacc tgttccctaa tagaccagat gccgccaggg acttcctgtt tcacgtggag  180
aagaggaaca caccgaggg ctgtcacgtg ctgctgcagt cgcccagat gccccgtgagc  240
accgcagtgg ccacagtgat caagaccaag caggtggagt tccagctgca agtgggcgtg  300
ccactgtact ttaggctgcg cgccaatccc atcaagacca tcctggataa ccagaagcgc  360
ctggactcta agggcaatat caagcggtgc agagtgcctc tgatcaagga ggccgagcag  420
atcgcctggc tgcagagaaa gctgggcaac gccgccaggg tgggatgt gcaccctatc  480
agcgagcggc cacagtattt cagcggcgac ggcaagtccg gcaagatcca gaccgtgtgc  540
tttgagggcg tgctgaccat caacgatgcc ccagccctga tcgaccggt gcagcaggga  600
atcggacctg ctaagtcaat gggatgtggg ctgctgtcac tggcacctct gaagcggact  660
gctgatggca gtgaatttga gtccccaaag aagaagagaa aggtggaa            708
```

| SEQ ID NO: 12 | moltype = DNA   length = 1200 |
|---|---|
| FEATURE | Location/Qualifiers |
| misc_feature | 1..1200 |
| | note = Synthetic sequence, modified Cas7 with BPNLS |
| source | 1..1200 |
| | mol_type = other DNA |
| | organism = synthetic construct |

SEQUENCE: 12

```
aagcggactg ctgatggcag tgaatttgag tccccaaaga agaagagaaa ggtggaatcc   60
aatttcatca acatccacgt gctgatctcc cactctccaa gctgcctgaa tagagacgat  120
atgaacatgc agaaggacgc catctttggc ggcaagcgga gagtggat ctctagccag  180
tccctgaagc gggccatgag aaagtctggc tactatgccc agaatatcgg cgagtcctct  240
ctgaggacca tccacctggc acagctgagg gacgtgctga cagaagct gggcgagcgg  300
tttgatcaga gatcatcga caagacactg gccctgctga gcggcaagtc cgtggatgag  360
gccgagaaga tcagcgccga cgcagtgacc ccatgggtgg tgggagagat cgcatggttc  420
tgtgcagcag tggccaaggc cgaggccgat aatctgacg ataagaagct gctgaaggtg  480
ctgaaggagg atatcgccgc catcagagtg aacctgcagc agggagtgga catcgccctg  540
agcggcagga tggccacatc cggcatgatg accgagctgg gcaaggtgga cggagcaatg  600
tccatcgcac acgccatcac cacacaccag gtggactctg atatcgactg gttcacagcc  660
gtggacgatc tgcaggagca gggaagcgcc cacctggaca cccaggtt cagctccgac  720
gtgtttaca gatatgccaa tatcaacctg gcacagctgc aggagaacct gggaggagca  780
tccagggagc aggccctgga gatcgccaca acgtggtgc acatgctggc aaccgaggtg  840
ccaggagcaa agcagcgcac ctacgccgcc ttcaatcctg ccgatatggt catggtgaac  900
ttttccgaca tgccactgtc tatggccaat gccttcgaga aggccgtgaa ggccaaggat  960
ggcttcctgc agccttccat ccaggccttt aaccagtact gggaccgcgt gccaatgga  1020
tatggcctga acgagctgc cgcccagttt tccctgtctg atgtggaccc tatcacagcc 1080
caggtgaagc agatgccaac cctgagcag ctgaagagct gggtgcgaa caatggagag 1140
gcaaagcgga ctgctgatgg cagtgaattt gagtccccaa agaagaagag aaaggtggaa 1200
```

| SEQ ID NO: 13 | moltype = DNA   length = 2664 |
|---|---|
| FEATURE | Location/Qualifiers |
| source | 1..2664 |
| | mol_type = unassigned DNA |
| | organism = Escherichia coli |

SEQUENCE: 13

```
atggagccat tcaaatacat ctgccactac tgggggaaat catctaaaag cctgacaaag    60
gggaacgata tccacctgct gatctaccac tgcctggacg tggcagcagt ggcagattgt   120
tggtgggacc agagcgtggt gctgcagaat accttctgcc ggaacgagat gctgtccaag   180
cagagagtga aggcctggct gctgttcttt atcgccctgc acgatatcgg caagttcgac   240
atcaggtttc agtataagtc tgccgagagc tggctgaagc tgaatccagc cacaccctcc   300
ctgaacggcc cttctaccca gatgtgcagg aagttcaatc acggagcagc aggactgtac   360
tggtttaacc aggacagcct gtccgagcag tctctgggcg atttctttag cttcttttgac  420
gccgccctc acccatatga gagctggttc catgggtgg aggcagtgac aggacaccac    480
ggctttatcc tgcactccca ggaccaggat aagtctagat gggagatgcc agcatccctg   540
gcatcttacg cagcacagga taagcaggca agggaggagt ggatctctgt gctggaggcc   600
ctgttcctga ccccagcagg cctgagcatc aatgatatcc cacctgactg cagctccctg   660
ctggcaggct tttgtagcct ggcagactgg ctgggatcct ggaccacaac caatacattc   720
ctgtttaacg aggatgcccc ttctgacatc aacgccctgc gcacctactt ccaggatcgg   780
cagcaggacg ccagcagagt gctggagctg tctggcctgg tgagcaataa gcggtgctac   840
gagggagtgc acgcactgct ggataacggc tatcagccta gacagctgca ggtgctggtg   900
gacgcactgc ctgtggcacc aggactgaca gtgatcgagg caccaaccgg ctctggcaag   960
acagagaccg ccctggccta tgcctggaag ctgatcgatc agcagatcgc cgacagcgtg  1020
atcttcgcac tgccaacaca ggcaaccgca aatgccatgc tgaccaggat ggaggcctct  1080
gccagccacc tgttttctag ccctaacctg atcctggccc acggcaacag ccggttcaat  1140
cacctgtttc agagcatcaa gtccagagcc atcacagagc agggacagga ggaggcatgg  1200
gtgcagtgct gtcagtggct gtcccagtct aacaagaagg tgttcctggg ccagatcggc  1260
gtgtgcacca tcgatcaggt gctgatctcc gtgctgccag tgaagcacag gtttatcagg  1320
ggactgggaa tcggccgctc tgtgctgatc gtggatgagg tgcacgccta cgacacatat  1380
atgaacggcc tgctggaggc cgtgctgaag gcacaggcca cgtgggagg aagcgtgatc  1440
ctgctgtccc cacccctgcc catgaagcag aagcagaagc tgctggatac atacggcctc  1500
cacaccgacc tgtgtggaga acaatagcgcc tatccactga tcaattggag ggagtgaac  1560
ggagcacagc ggttcgacct gctggcacac ccagagcagc tgccaccacg gttttccatc  1620
cagcccgagc ctatctgcct ggcgatatg ctgcccgacc tgaccatgct ggagagaatg  1680
atcgctgccg ccaatgcagg agcacaggtg tgcctgatct gtaacctggt ggatgtggcc  1740
caggtgtgct accagcggct gaaggagctg aacaatacac aggtggacat cgatctgttc  1800
cacgccaggt ttaccctgaa tgaccggaga gagaaggaga accgcgtgat ctccaacttc  1860
ggcaagaatg gcaagagaaa cgtgggcagg atcctggtgg ccacacaggt ggtggagcag  1920
tctctggacg tggatttcga ctggctgatc acccagcact gccctgccga tctgctgttt  1980
cagcggctgg gcagactgca cagacaccac aggaagtaca ggccagcagg atttgagatc  2040
ccagtggcca caatcctgct gccagacgga gagggatacg gccggcacga gcacatctat  2100
agcaatgtgc gcgtgatgtg gcggacccag cagcacatcg aggagctgaa cggcgcctcc  2160
ctgttcttc cgatgccta cagacagtgg ctggactcta tctatgacga tgccgagatg  2220
gatgagcctg agtgggtggg caatggcatg gacaagttcg agtccgccga gtgtgagaag  2280
cggttcaagg ccaggaaggt gctgcagtgg gccgaggagt aggataacgac  2340
gagacaatcc tggccgtgac cagggatggc gagatgtccc tgcccctgct gccttatgtg  2400
cagacatcct ctggcaagca gctgctggat ggccaggtgt acgaggacct gagccacgag  2460
cagcagtatg aggccctggc cctgaacagg gtgaatgtgc ccttcacctg gaagcgcagc  2520
ttttccgaag tggtggatga ggacggcctc ctgtggctgg agggcaagca gaatctggac  2580
ggctgggtgt ggcagggcaa ctccatcgtg attacctaca ccggagacga agggatgaca  2640
agagtgattc ctgctaaccc aaaag                                        2664

SEQ ID NO: 14          moltype = DNA   length = 1506
FEATURE                Location/Qualifiers
source                 1..1506
                       mol_type = unassigned DNA
                       organism = Escherichia coli
SEQUENCE: 14
atgaatttgc ttattgataa ctggatccct gtacgcccgc gaaacgggg gaaagtccaa     60
atcataaatc tgcaatcgct atactgcagt agagatcagt ggcgattaag tttgccccgt   120
gacgatatgg aactggccgc tttagcactg ctggtttgca ttgggcaaat tatcgccccg   180
gcaaaagatg acgttgaatt tcgacatcgc ataatgaatc cgctcactga agatgagttt   240
caacaactca tcgcgccgtg gatagatatg ttctacctta atcacgcaga acatcccttt   300
atgcagacca aaggtgtcaa agcaaatgat gtgactccaa tggaaaaact gttggctggg   360
gtaagcggcg cgacgaattg tgcatttgtc aatcaaccgg ggcagggtga agcattatgt   420
ggtggatgca ctgcgattgc gttattcaac caggcgaatc aggcaccagg ttttggtggt   480
ggttttaaaa gcggtttacg tggaggaaca cctgtaacaa cgttcgtacg tgggatcgat   540
cttcgttcaa cggtgttact caatgtcctc acattacctc gtcttcaaaa acaatttcct   600
aatgaatcac atacggaaaa ccaacctacc tggattaaac ctatcaagtc caatgagtct   660
ataccctgct cgtcaattgg gtttgtccgt ggtcattcca gcaaccagc gcatattgaa   720
ttatgcgatc ccattgggat tggtaaatgt tcttgctgtg gacaggaaag caatttgcgt   780
tataccggtt ttcttaagga aaaatttacc tttacagtta atgggctatg ccccatccg   840
cattcccctt gtctggtaac agtcaagaaa ggggaggttg aggaaaaatt tcttgctttc   900
accacctccg caccatcatg gacacaaatc agccagagtt tggtagataa gattattcaa   960
aatgaaaatg gaaatcgcgt ggcggcggtt gtgaatcaat tcagaaatat tgcgccgcaa  1020
agtcctcttg aattgattat gggggatat cgtaataatc aagcatctat tcttgaacgt  1080
cgtcatgatg tgttgatgtt taatcagggg tggcaacaat acggcaatgt gataaacgaa  1140
atagtgacta ttggtttggg atataaaaca gccttacgca aggcgttata tcctttgca  1200
gaaggggttta aaaataaaga cttcaaaggg gccggagtct ctgttcatga gactgcagaa  1260
aggcatttct atcgacagag tgaattatta ttcccgatta tgttaatttt  1320
tcccaggctg atgaggtaat agctgattta cgagacaaac ttcatcaatt gtgtgaaatg  1380
ctattaatc aatctgtagc tcccatgcaa catcatccta aattaataag cacattagcg  1440
cttgcccgcg ccacgctata caaacattta cgggagttaa aaccgcaagg agggccatca  1500
aatggc                                                             1506
```

| SEQ ID NO: 15 | moltype = DNA length = 480 |
|---|---|
| FEATURE | Location/Qualifiers |
| source | 1..480 |
| | mol_type = unassigned DNA |
| | organism = Escherichia coli |

SEQUENCE: 15

```
atggctgatg aaattgatgc aatggcttta tatcgagcct ggcaacaact ggataatgga    60
tcatgtgcgc aaattagacg tgtttcagaa cctgatgaat tacgcgatat ccctgcgttt   120
tataggctgg tgcaacccttt tggttgggaa aacccacgtc accagcaggc tcttttgcgc  180
atggtgtttt gcctgagcgc aggaaagaat gtcatccgac atcaggacaa aaaatcggag  240
caaacaacag gtatctcgtt gggaagagct ttagccaata gtggaagaat taacgagcgc  300
cgtatctttc aattaattcg ggctgacaga acagccgata tggtccagtt acgtcgatta  360
cttactcacg ccgaacccgt acttgactgg ccattaatgg ccaggatgtt gacctggtgg  420
ggaaagcgcg aacgccagca acttctggaa gattttgtat tgaccacaaa caaaaatgcg  480
```

| SEQ ID NO: 16 | moltype = DNA length = 672 |
|---|---|
| FEATURE | Location/Qualifiers |
| source | 1..672 |
| | mol_type = unassigned DNA |
| | organism = Escherichia coli |

SEQUENCE: 16

```
atgagatctt atttgatctt gcggcttgct gggccaatgc aagcctgggg gcagccgacc    60
tttgaaggaa cgcgacctac cggaagattt ccgacccgaa gcgggttatt agggctactc   120
ggggcttgtc ttgggatcca acgtgatgat acttcttcat tacaggcgtt atcagagagt   180
gtgcaatttg cagtgcgctg cgatgaactc attcttgacg atcgtcgtgt gtctgtaacg   240
gggttgcgtg attaccatac agtccttgga gcgcgagaag attacgtgg tttgaaaagt   300
catgaaacga ttcaaacatg cgcgaatat ttatgtgatg cctcctttac cgtcgctctc   360
tggttaacac cccatgcaac gatggttatc tcagaacttg aaaaagcagt attaaagcct   420
cggtatacac cttacctggg gcggagaagt tgcccactaa cacacccgct ttttttgggg  480
acatgtcagg catcggatcc tcagaaggcg ctattaaatt gagcccgt tggcggcagt    540
atatatagtg aggaatcagt tacagggcat catttaaat ttacggcgcg cgacgaaccg  600
atgatcacct tgcctcgaca atttgcttcc cgagaatggt atgtgattaa aggaggtatg  660
gatgtatctc ag                                                     672
```

| SEQ ID NO: 17 | moltype = DNA length = 597 |
|---|---|
| FEATURE | Location/Qualifiers |
| source | 1..597 |
| | mol_type = unassigned DNA |
| | organism = Escherichia coli |

SEQUENCE: 17

```
atgtatctca gtaaagtcat cattgccagg gcctggagca gggatctta ccaacttcac     60
cagggattat ggcattttatt tccaaacaga ccggatgctg ctcgtgattt tcttttcat   120
gttgagaagc gaaacacacc agaaggctgt catgttttat tgcagtcagc gcaaatgcct   180
gtttcaactg ccgttgcgac agtcattaaa actaaacagg ttgaatttca acttcaggtt   240
ggtgttccac tctattttcg gcttcgggca atccgatca aaactattct cgacaatcaa    300
aagcgcctga cagtaaagg gaatattaaa cgctgtcggg ttccgttaat aaaagaagca   360
gaacaaatcg cgtggttgca acgtaaaattg ggcaatgcgg cgcgcgttga agatgtgcat  420
cccatatcgg aacggccaca gtattttttct ggtgatggta aaagtggaaa gatccaaacg  480
gtttgctttg aaggtgtgct caccatcaac gacgcgccag cgttaataga tcttgtacag  540
caaggtattg ggccagctaa atcgatggga tgtggcttgc tatctttggc tccactg     597
```

| SEQ ID NO: 18 | moltype = DNA length = 1086 |
|---|---|
| FEATURE | Location/Qualifiers |
| source | 1..1086 |
| | mol_type = unassigned DNA |
| | organism = Escherichia coli |

SEQUENCE: 18

```
tctaacttta tcaatattca tgttctgatc tctcacagcc cttcatgtct gaaccgcgac    60
gatatgaaca tgcagaaaga cgctatttc ggcggcaaaa gacgagtaag aatttcaagt   120
caaagcctta aacgtgcgat gcgtaaaagt ggttattacg cacaaaatat tggtgaatcc   180
agtctcagaa ccattcatct tgcacaatta cgtgatgttc ttcggcaaaa acttggtgaa  240
cgttttgacc aaaaaatcat cgataagaca ttagcgctgc tctccggtaa atcagttgat  300
gaagccgaaa agatttctgc cgatgcggtt actccctggg ttgtgggaga aatagcctgg  360
ttctgtgagc aggttgcaaa agcagaggct gataatctga atgataaaaa gctgctcaaa  420
gttcttaagg aagatattgc cgccatacgt gtgaatttac agcaggggtgt tgatattgcg  480
cttagtggaa gaatggcaac cagcggcatg atgactgagt tgggaaaagt tgatggtgca  540
atgtccattg cgcatgcgat cactactcat caggttgatt ctgatattga ctggttcacc  600
gctgtagatg atttacagga acaaggttct gcacatctgg gaactcagga atttcatcg   660
gtgttttttt atcgttatgc caacattaac ctcgctcaac ttcaggaaaa tttaggtggt  720
gcctccaggg agcaggctct ggaaattgca acccatgttg ttcatatgct ggcaacagag  780
gtccctggag caaaacagcg tacttatgcc gcttttaacc ctgcggatat ggtaatggtt  840
aatttctccg atatgccact ttctatggca aatgcttttg aaaaagcggt taagcgaaa   900
gatggctttt tgcaaccgtc tatacaggcg tttaatcaat attgggatcg cgttgccaat  960
ggatatggtc tgaaggagc tgtgcgcaa ttcagcttat ctgatgtaga cccaattact  1020
gctcaagtta aacaaatgcc tactttagaa cagttaaaat cctgggttcg taataatggc 1080
gaggcg                                                            1086
```

| SEQ ID NO: 19 | moltype = DNA length = 39 |
|---|---|
| FEATURE | Location/Qualifiers |

```
misc_feature            1..39
                        note = Synthetic sequence, target (CCR5)
source                  1..39
                        mol_type = other DNA
                        organism = synthetic construct
SEQUENCE: 19
tcaagtccaa tctatgacat caattattat acatcggag                             39

SEQ ID NO: 20           moltype = DNA  length = 50
FEATURE                 Location/Qualifiers
misc_feature            1..50
                        note = Synthetic sequence, reporter vector insert1 (CCR5)
source                  1..50
                        mol_type = other DNA
                        organism = synthetic construct
SEQUENCE: 20
gtcggattca agtccaatct atgacatcaa ttattataca tcggagaggt                 50

SEQ ID NO: 21           moltype = DNA  length = 50
FEATURE                 Location/Qualifiers
misc_feature            1..50
                        note = Synthetic sequence, reporter vector insert2 (CCR5)
source                  1..50
                        mol_type = other DNA
                        organism = synthetic construct
SEQUENCE: 21
cggtacctct ccgatgtata ataattgatg tcatagattg gacttgaatc                 50

SEQ ID NO: 22           moltype = DNA  length = 35
FEATURE                 Location/Qualifiers
misc_feature            1..35
                        note = Synthetic sequence, target (E. coli)
source                  1..35
                        mol_type = other DNA
                        organism = synthetic construct
SEQUENCE: 22
aagagcacaa atatcatcgc tcaaaccact tacgg                                 35

SEQ ID NO: 23           moltype = DNA  length = 46
FEATURE                 Location/Qualifiers
misc_feature            1..46
                        note = Synthetic sequence, reporter vector insert1 (E. coli)
source                  1..46
                        mol_type = other DNA
                        organism = synthetic construct
SEQUENCE: 23
gtcggataag agcacaaata tcatcgctca aaccacttac ggaggt                     46

SEQ ID NO: 24           moltype = DNA  length = 46
FEATURE                 Location/Qualifiers
misc_feature            1..46
                        note = Synthetic sequence, reporter vector insert2 (E. coli)
source                  1..46
                        mol_type = other DNA
                        organism = synthetic construct
SEQUENCE: 24
cggtacctcc gtaagtggtt tgagcgatga tatttgtgct cttatc                     46

SEQ ID NO: 25           moltype = DNA  length = 36
FEATURE                 Location/Qualifiers
misc_feature            1..36
                        note = Synthetic sequence, crRNA insert1 (CCR5)
source                  1..36
                        mol_type = other DNA
                        organism = synthetic construct
SEQUENCE: 25
accgtccaat ctatgacatc aattattata catcgg                                36

SEQ ID NO: 26           moltype = DNA  length = 36
FEATURE                 Location/Qualifiers
misc_feature            1..36
                        note = Synthetic sequence, crRNA insert 2(CCR5)
source                  1..36
                        mol_type = other DNA
                        organism = synthetic construct
SEQUENCE: 26
acacccgatg tataataatt gatgtcatag attgga                                36

SEQ ID NO: 27           moltype = DNA  length = 36
```

```
FEATURE                     Location/Qualifiers
misc_feature                1..36
                            note = Synthetic sequence, crRNA insert1 (E.coli)
source                      1..36
                            mol_type = other DNA
                            organism = synthetic construct
SEQUENCE: 27
accgagcaca aatatcatcg ctcaaaccac ttacgg                             36

SEQ ID NO: 28               moltype = DNA   length = 36
FEATURE                     Location/Qualifiers
misc_feature                1..36
                            note = Synthetic sequence, crRNA insert 2(E.coli)
source                      1..36
                            mol_type = other DNA
                            organism = synthetic construct
SEQUENCE: 28
acacccgtaa gtggtttgag cgatgatatt tgtgct                             36

SEQ ID NO: 29               moltype = DNA   length = 36
FEATURE                     Location/Qualifiers
misc_feature                1..36
                            note = Synthetic sequence, crRNA insert 1(EMX1)
source                      1..36
                            mol_type = other DNA
                            organism = synthetic construct
SEQUENCE: 29
accgcaggcc aatggggagg acatcgatgt cacctc                             36

SEQ ID NO: 30               moltype = DNA   length = 36
FEATURE                     Location/Qualifiers
misc_feature                1..36
                            note = Synthetic sequence, crRNA insert 2(EMX1)
source                      1..36
                            mol_type = other DNA
                            organism = synthetic construct
SEQUENCE: 30
acacgaggtg acatcgatgt cctccccatt ggcctg                             36

SEQ ID NO: 31               moltype = DNA   length = 5701
FEATURE                     Location/Qualifiers
misc_feature                1..5701
                            note = Synthetic sequence, reporter vector (CCR5)
source                      1..5701
                            mol_type = other DNA
                            organism = synthetic construct
SEQUENCE: 31
ggcctaactg gccggtacct agtgattaat agtaatcaat tacggggtca ttagttcata   60
gcccatatat ggagttccgc gttacataac ttacggtaaa tggcccgcct ggctgaccgc  120
ccaacgaccc ccgcccattg acgtcaataa tgacgtatgt tcccatagta acgccaatag  180
ggactttcca ttgacgtcaa tgggtggagt atttacggta aactgcccac ttggcagtac  240
atcaagtgta tcatatgcca agtacgcccc ctattgacgt caatgacggt aaatggcccg  300
cctggcatta tgcccagtac atgaccttat gggactttcc tacttggcag tacatctacg  360
tattagtcat cgctattacc atggtgatgc ggttttggca gtacatcaat gggcgtggat  420
agcggtttga ctcacgggga tttccaagtc tccacccatt gacgtcaat gggagtttgt  480
tttggcacca aaatcaacgg gactttccaa aatgtcgtaa caactccgcc ccattgacga  540
aaatgggcgg taggcgtgta cggtgggagg tctatataag cagagctggt ttagtgaacc  600
gtcagatccg ctagcgctac cggactcaga tctcgagctc aagcttggca atccggtact  660
gttggtaaag ccaccatgga agatgccaaa aacattaaga agggcccagc gccattctac  720
ccactcgaag acgggaccgc cggcgagcag ctgcacaaag ccatgaagcg ctacgccctg  780
gtgcccggca ccatcgcctt taccgacgca catatcgagg tggacattac ctacgccgag  840
tacttcgaga tgagcgttcg gctggcagaa gctatgaagc gctatgggct gaatacaaac  900
catcggatcg tggtgtgcag cgagaatagc ttgcagttct tcatgcccgt gttgggtgcc  960
ctgttcatcg gtgtggctgt ggccccagct aacgacatct acaacgagcg cgagctgctg 1020
aacagcatgg gcatcagcca gcccaccgtc gtattcgtga gcaagaaagg gctgcaaaag 1080
atcctcaacg tgcaaaagaa gctaccgatc atacaaaaga tcatcatcat ggatagcaag 1140
accgactacc agggcttcca agcatgtac accttcgtga cttcccattt gccacccggc 1200
ttcaacgagt acgacttcgt gcccgagagc ttcgaccggg acaaaaccat cgccctgatc 1260
atgaacagta gtggcagtac cggattgccc aagggcgtag ccctaccgca cgcgaccctg 1320
tgtgtccgat tcagtcatgc ccgcgacccc atcttcggca accagatcat ccccgacacc 1380
gctatcctca gcgtggtgcc atttcaccac ggcttcggca tgttcaccac gctgggctac 1440
ttgatctgcg gctttcgggt cgtgctcatg taccgcttcg aggaggagct attcttgcgc 1500
agcttgcaag actataagat tcaatctgcc ctgctggtgc ccacactatt tagcttcttc 1560
gctaagacta ctctcatcga caagtacgac ctaagcaact tgcacgagat cgccagcggc 1620
ggggcgccgc tcagcaagga ggtaggtgag gccgtggcca aacgcttcca cctaccaggc 1680
atccgcagg gctacggcct gacagaaaca accagcgcca ttctgatcac ccccgaaggg 1740
gacgacaagc tgcgcgcagt aggcaaggtg tgcccttct tcgaggctaa ggtggtggac 1800
ttggactagg gtctctgtcg gattcaagtc caatctgatg catcaattat tatacatcgg 1860
agaggtaccg tgagacctag gagcgcgagc tgctgaacag catgggcatc agccagccca 1920
```

-continued

```
cgtcgtatt cgtgagcaag aaagggctgc aaaagatcct caacgtgcaa aagaagctac 1980
cgatcataca aaagatcatc atcatggata gcaagaccga ctaccagggc ttccaaagca 2040
tgtacacctt cgtgacttcc catttgccac ccggcttcaa cgagtacgac ttcgtgcccg 2100
agagcttcga ccgggacaaa accatcgccc tgatcatgaa cagtagtggc agtaccggat 2160
tgccaagggg cgtagcccta ccgcaccgca ccgcttgtgt ccgattcagt catgcccgcg 2220
accccatctt cggcaaccag atcatccccg acaccgctat cctcagcgtg gtgccatttc 2280
accacggctt cggcatgttc accacgctgg gctacttgat ctgcggcttt cgggtcgtgc 2340
tcatgtaccg cttcgaggag gagctattct tgcgcagctt gcaagactat aagattcaat 2400
ctgccctgct ggtgcccaca ctatttagct tcttcgctaa gagcactctc atcgacaagt 2460
acgacctaag caacttgcac gagatcgcca gcggcggggc gccgctcagc aaggaggtag 2520
gtgaggccgt ggccaaacgc ttccacctac caggcatccg ccaggctac ggcctgacag 2580
aaacaaccag cgccattctg atcacccccg aaggggacga caagcctggc gcagtaggca 2640
aggtggtgcc cttcttcgag gctaaggtgg tggacttgga caccggtaag acactgggtg 2700
tgaaccagcg cggcgagctg tgcgtccgtg gccccatgat catgagcggc tacgttaaca 2760
accccgaggc tacaaacgct ctcatcgaca aggacggctg gctgcacagc ggcgacatcg 2820
cctactggga cgaggacgag cacttcttca tcgtggaccg gctgaagagc ctgatcaaat 2880
acaagggcta ccaggtagcc ccagccgaac tggagagcat cctgctgcaa caccccaaca 2940
tcttcgacgc cggggtcgcc ggcctgcccg acgacgatgc cggcgagctg cccgccgcag 3000
tcgtcgtgct ggaacacggt aaaaccatga ccgagaagga gatcgtggac tatgtggcca 3060
gccaggttac aaccgccaag aagctgcgcg gtggtgttgt gttcgtggac gaggtgccta 3120
aaggactgac cggcaagttg gacgcccgca agatccgcga gattctcatt aaggccaaga 3180
agggcggcaa gatcgccgtg aattcttaac tgcagtctag agtcggggc ccgccgcagt 3240
tcgagcagac atgataagat acattgatga gtttggacaa accacaacta gaatgcagtg 3300
aaaaaaatgc tttatttgtg aaatttgtga tgctattgct ttatttgtaa ccattataag 3360
ctgcaataaa caagttaaca acaacaattg cattcatttt atgtttcagg ttcaggggga 3420
ggtgtgggag gttttttaaa gcaagtaaaa cctctacaaa tgtggtaaaa tcgataagga 3480
tccgtcgacc gatgcccttg agagccttca acccagtcag ctccttccgg tgggcgcggg 3540
gcatgactat cgtcgccgca cttatgactg tcttctttat catgcaactc gtaggacagg 3600
tgccggcagc gctcttccgc ttcctcgctc actgactcgc tgcgctcggt cgttcggctg 3660
cggcgagcgg tatcagctca ctcaaaggcg gtaatacggt tatccacaga atcaggggat 3720
aacgcaggaa agaacatgtg agcaaaaggc cagcaaaagg ccaggaaccg taaaaaggcc 3780
gcgttgctgg cgtttttcca taggctccgc cccctgacg agcatcacaa aatcgacgc 3840
tcaagtcaga ggtggcgaaa cccgacagga ctataaagat accaggcgtt ccccctgga 3900
agctccctcg tgcgctctcc tgttccgacc ctgccgctta ccggatacct gtccgccttt 3960
ctcccttcgg gaagcgtggc gctttctcat agctcacgct gtaggtatct cagttcggtg 4020
taggtcgttc gctccaagct gggctgtgtg cacgaacccc ccgttcagcc cgaccgctgc 4080
gccttatccg gtaactatcg tcttgagtcc aacccggtaa gacacgactt atcgccactg 4140
gcagcagcca ctggtaacag gattagcaga gcgaggtatg taggcggtgc tacagagttc 4200
ttgaagtggt ggcctaacta cggctacact agaagaacag tatttggtat ctgcgctctg 4260
ctgaagccag ttaccttcgg aaaaagagtt ggtagctctt gatccggcaa acaaaccacc 4320
gctggtagcg gtggttttt tgtttgcaag cagcagatta cgcgcagaaa aaaggatct 4380
caagaagatc ctttgatctt ttctacgggg tctgacgctc agtggaacga aaactcacgt 4440
taagggattt tggtcatgag attatcaaaa aggatcttca cctagatcct tttaaattaa 4500
aaatgaagtt ttaaatcaat ctaaagtata tatgagtaaa cttggtctga cagcggccgc 4560
aaatgctaaa ccactgcagt ggttaccagt gcttgatcag tgaggcaccg atctcagcga 4620
tctgcctatt tcgttcgtcc atagtggcct gactccccgt cgtgtagatc actacgattc 4680
gtgagggctt accatcaggc cccagcgcag caatgatgca gcgagagccg cgttcaccgg 4740
cccccgattt gtcagcaatg aaccagccag cagggagggc cgagcgaaga agtggtcctg 4800
ctactttgtc cgcctccatc cagtctatga gctgctgtcg tgatgctaga gtaagaagtt 4860
cgccagtgag tagtttccga agagttgtgg ccattgctac tggcatcgtg gtatcacgct 4920
cgtcgtttga tatggcttcg ttcaactctg gttcccaggc gtcaagccgg gtcacatgat 4980
cacccatatt atgaagaaat gcagtcagct cctagggcc tccgatcgtt gtcagaagta 5040
agttggccgc ggtgttgtcg ctcatggtaa tggcagcact acacaattct cttaccgtca 5100
tgccatccgt aagatgcttt tccgtgaccg gcgagtactc aaccagtcg ttttgtgagt 5160
agtgtatacg gcgaccaagc tgctcttgcc cggcgtctat acgggacaac accgcgccac 5220
atagcagtac tttgaaagtg ctcatcatcg gaatcgttc ttcggggcgg aaagactcaa 5280
ggatcttgcc gctattgaga tccagttcga tatagcccac tcttgcaccc agttgatctt 5340
cagcatcttt tactttcacc agcgtttcgg ggtgtgcaaa acaggcaag caaaatgccg 5400
caaagaaggg aatgagtgcg acacgaaaat gttggatgct catactcgtc ttttttcaat 5460
attattgaag catttatcag ggttactagt acgtctctca aggataagta agtaatatta 5520
aggtacggga ggtattggac aggccgcaat aaaatatctt tattttcatt acatctgtgt 5580
gttggttttt tgtgtgaatc gatagtacta acatacgctc tccatcaaaa caaaacgaaa 5640
caaaacaaac tagcaaaata ggctgtcccc agtgcaagtg caggtgccag aacatttctc 5700
t                                                                5701

SEQ ID NO: 32       moltype = DNA   length = 5697
FEATURE             Location/Qualifiers
misc_feature        1..5697
                    note = Synthetic sequence, reporter vector (E. coli)
source              1..5697
                    mol_type = other DNA
                    organism = synthetic construct
SEQUENCE: 32
ggcctaactg gccggtacct agtgattaat agtaatcaat tacgggtca ttagttcata  60
gcccatatat ggagttccgc gttacataac ttacggtaaa tggcccgcct ggctgaccgc 120
ccaacgaccc ccgcccattg acgtcaataa tgacgtatgt tcccatagta acgccaatag 180
ggactttcca ttgacgtcaa tgggtggagt atttacggta aactgcccac ttggcagtac 240
atcaagtgta tcatatgcca agtacgcccc ctattgacgt caatgacggt aaatggcccg 300
cctggcatta tgcccagtac atgaccttat gggactttcc tacttggcag tacatctacg 360
```

```
tattagtcat cgctattacc atggtgatgc ggttttggca gtacatcaat gggcgtggat    420
agcggtttga ctcacgggga tttccaagtc tccaccccat tgacgtcaat gggagtttgt    480
tttggcacca aaatcaacgg gactttccaa aatgtcgtaa caactccgcc ccattgacgc    540
aaatgggcgg taggcgtgta cggtgggagg tctatataag cagagctggt ttagtgaacc    600
gtcagatccg ctagcgctac cggactcaga tctcgagctc aagcttggca atccggtact    660
gttggtaaag ccaccatgga agatgccaaa aacattaaga agggcccagc gccattctac    720
ccactcgaag acgggaccgc cggcgagcag ctgcacaaag ccatgaagcg ctacgccctg    780
gtgcccggca ccatcgcctt taccgacgca catatcgagg tggacattac ctacgccgag    840
tacttcgaga tgagcgttcg gctggcagaa gctatgaagc gctatgggct gaatacaaac    900
catccggatcg tggtgtgcag cgagaatagc ttgcagttct tcatgcccgt gttgggtgcc    960
ctgttcatcg gtgtggctgt ggccccagct aacgacatct acaacgagcg cgagctgctg   1020
aacagcatgg gcatcagcca gcccaccgtc gtattcgtga gcaagaaagg gctgcaaaag   1080
atcctcaacg tgcaaaagaa gctaccgatc atacaaaaga tcatcatcat ggatagcaag   1140
accgactacc agggcttcca aagcatgtac accttcgtga cttcccattt gccaccggc    1200
ttcaacgagt acgacttcgt gcccgagagc ttcgaccggg acaaaaccat cgccctgatc   1260
atgaacagta gtggcagtac cggattgccc aagggcgtag ccctaccgca ccgcaccgct   1320
tgtgtccgat tcagtcatgc ccgcgacccc atcttcggca accagatcat ccccgacacc   1380
gctatcctca gcgtggtgcc atttcaccac ggcttcggca tgttcaccac gctgggctac   1440
ttgatctgcg gctttcgggt cgtgctcatg taccgcttcg aggaggagct attcttcgcg   1500
agcttgcaag actataagat tcaatctgcc ctgctggtgc ccacactatt tagcttcttc   1560
gctaagagca ctctcatcga caagtacgac ctaagcaact tgcacgagat cgccagcggc   1620
ggggcgccgc tcagcaagga ggtaggtgag gccgtgccca aacgcttcca cctaccaggc   1680
atccgccagg gctacggcct gacagaaaca accagcgcca ttctgatcac ccccgaaggg   1740
gacgacaagc tggcgcagt aggcaaggtg gtgcccttct cgaggctaa ggtggtggac    1800
ttggactagg gtctctgtcg gataagagca caaatatcat cgctcaaacc acttacggag   1860
gtaccgtgag acctaggagc gcgagctgct gaacagcatg ggcatcagcc agcccaccgt   1920
cgtattcgtg agcaagaaag ggctgcaaaa gatcctcaac gtgcaaaaga agctaccgat   1980
catacaaaag atcatcatca tggatagcaa gaccgactac cagggcttcc aaagcatgta   2040
caccttcgtg acttcccatt tgccaccggg cttcaacgag tacgacttcg tgcccgagag   2100
cttcgacggg gacaaaacca tcgccctgat catgaacagt agtggcagta ccggattgcc   2160
caagggcgta gccctaccgc accgcaccgc ttgtgtccga ttcagtcatg ccgcgacccc   2220
atcttcggc aaccagatca tccccgacac cgctatcctc agcgtggtgc catttcacca   2280
cggcttcggc atgttcacca cgctgggcta cttgatctgc ggctttcggg tcgtgctcat   2340
gtaccgcttc gaggaggagc tattcttcgc gagcttgcaa gactataaga ttcaatctgc   2400
cctgctggtg cccacactat ttagcttctt cgctaagagc actctcatcg acaagtacga   2460
cctaagcaac ttgcacgaga tcgccagcgg cggggcgccg ctcagcaagg aggtaggtga   2520
ggccgtggcc aaacgcttcc acctaccagg catccgccag ggctacggcc tgacagaaac   2580
aaccagcgcc attctgatca ccccgaaggg ggacgacaag cctggcgcag taggcaaggt   2640
ggtgcccttc tcgaggcta aggtggtgga cttggacacc ggtaagacac tgggtgtgaa   2700
ccagccgcgg gagctgtgcg tccgtggccc catgatcatg agcggctacg ttaacaaccc   2760
cgaggctaca aacgctctca tcgacaagga cggctggctg cacagcggcg acatcgccta   2820
ctgggacgag acgagcact tcttcatcgt ggaccggctg aagagcctga tcaaatacaa   2880
gggctaccag gtagcccag ccgaactgga gagcatcctg ctgcaacacc caacatctt   2940
cgacgccggg gtcgccggcc tgcccgacga cgatgccggc gagctgcccg ccgcagtcgt   3000
cgtgctggaa cacggtaaaa ccatgaccga aagggagatc gtggactatg tggccagcca   3060
ggttacaacc gccaagaagc tgcgcggtgg tgttgtgttc gtggacgagg tgcctaaagg   3120
actgaccggc aagttggacg cccgcaagat ccgcgagatt ctcattaagg ccaagaaggg   3180
cggcaagatc gccgtgaatt cttaactgca gtctagagtc ggggcggccg gccgcttcga   3240
gcagacatga taagatacat tgatgagttt ggacaaacca caactagaat gcagtgaaaa   3300
aaatgcttta tttgtgaaat ttgtgatgct attgctttat ttgtaaccat tataagctgc   3360
aataaacaag ttaacaacaa caattgcatt catttttatgt ttcaggttca ggggaggtg   3420
tgggaggttt tttaaagcaa gtaaaactc tacaaatgtg gtaaaatcga taaggatccg   3480
tcgaccgatg cccttgagag ccttcaaccc agtcagctcc ttccggtggg cgcggggcat   3540
gactatcgtc gccgcactta tgactgtctt ctttatcatg caactcgtag acaggtgcc   3600
ggcagcgctc ttccgcttcc tcgctcactg actcgctgcg ctcggtcgtt cggctgcggc   3660
gagcggtatc agctcactca aaggcggtaa tacggttatc cacagaatca ggggataacg   3720
caggaaagaa catgtgagca aaaggccagc aaaaggccag gaaccgtaaa aaggccgcgt   3780
tgctggcgtt tttccatagg ctccgccccc ctgacgagca tcacaaaaat cgacgctcaa   3840
gtcagaggtg gcgaaacccg acaggactat aaagatacca ggcgtttccc cctggaagct   3900
ccctcgtgcg ctctcctgtt ccgaccctgc cgcttaccgg atacctgtcc gcctttctcc   3960
cttcgggaag cgtggcgctt tctcatagct cacgctgtag gtatctcagt tcggtgtagg   4020
tcgttcgctc caagctgggc tgtgtgcacg aaccccccgt tcagcccgac cgctgcgcct   4080
tatccggtaa ctatcgtctt gagtccaacc cggtaagaca cgacttatcg ccactggcag   4140
cagccactgg taacaggatt agcagagcga ggtatgtagg cggtgctaca gagttcttga   4200
agtggtggcc taactacggc tacactagaa gaacagtatt tggtatctgc gctctgctga   4260
agccagttac cttcggaaaa agagttggta gctcttgatc cggcaaacaa accaccgctg   4320
gtagcggtgg tttttttgtt tgcaagcagc agattacgcg cagaaaaaaa ggatctcaag   4380
aagatccttt gatcttttct acggggtctg acgctcagtg gaacgaaaac tcacgttaag   4440
ggattttggt catgagatta tcaaaaagga tcttcaccta gatccttta aattaaaaat   4500
gaagttttaa atcaatctaa agtatatatg agtaaacttg gtctgacagc ggccgcaaat   4560
gctaaaccac tgcagtggtt accagtgctt gatcagtgag gcaccgatct cagcgatctg   4620
cctatttcgt tcgtccatag tggcctgact ccccgtcgtg tagatcacta cgattcgtga   4680
gggcttacca tcaggcccca gcgcagcaat gatgccgcga gagccgcgtt caccggcccc   4740
cgatttgtca gcaatgaacc agccagcagg gaggcgcga cgaagaagtg gtcctgctac   4800
tttgtccgcc tccatccagt ctatgagctg ctgtcgtgat gctagagtaa gaagttcgcc   4860
agtgagtagt ttccgaagag ttgtggccat tgctactggc atcgtggtat cacgctcgtc   4920
gttcggtatg gcttcgttca actctggttc cagcgggtca agccgggtca catgatcacc   4980
catattgata agaaatgcag tcagctcctt agggcctccg atcgttgtca gaagtaagtt   5040
ggccgcggtg ttgtcgctca tggtaatggc agcactacac aattctctta ccgtcatgcc   5100
```

```
atccgtaaga tgcttttccg tgaccggcga gtactcaacc aagtcgtttt gtgagtagtg   5160
tatacggcga ccaagctgct cttgcccggc gtctatacgg gacaacaccg cgccacatag   5220
cagtactttg aaagtgctca tcatcgggaa tcgttcttcg gggcggaaag actcaaggat   5280
cttgccgcta ttgagatcca gttcgatata gcccactctt gcacccagtt gatcttcagc   5340
atcttttact ttcaccagcg tttcggggtg tgcaaaaaca ggcaagcaaa atgccgcaaa   5400
gaagggaatg agtgcgacac gaaaatgttg gatgctcata ctcgtccttt ttcaatatta   5460
ttgaagcatt tatcagggtt actagtacgt ctctcaagga taagtaagta atattaaggt   5520
acgggaggta ttggacaggc cgcaataaaa tatctttatt ttcattacat ctgtgtgttg   5580
gttttttgtg tgaatcgata gtactaacat acgctctcca tcaaaacaaa acgaaacaaa   5640
acaaactagc aaaataggct gtccccagtg caagtgcagg tgccagaaca tttctct      5697

SEQ ID NO: 33           moltype = DNA   length = 3391
FEATURE                 Location/Qualifiers
misc_feature            1..3391
                        note = Synthetic sequence, crRNA vector (CCR5)
source                  1..3391
                        mol_type = other DNA
                        organism = synthetic construct
SEQUENCE: 33
gtggcacttt tcgggaaat gtgcgcggaa cccctatttg tttattttc taaatacatt    60
caaatatgta tccgctcatg agacaataac cctgataaat gcttcaataa tattgaaaaa   120
ggaagagtat gagtattcaa catttccgtg tcgcccttat tcccttttt gcggcatttt   180
gccttcctgt ttttgctcac ccagaaacgc tggtgaaagt aaaagatgct gaagatcagt   240
tgggtgcacg agtgggttac atcgaactgg atctcaacag cggtaagatc cttgagagtt   300
ttcgccccga agaacgtttt ccaatgatga gcacttttaa agttctgcta tgtggcgcgg   360
tattatcccg tattgacgcc gggcaagagc aactcggtcg ccgcatacac tattctcaga   420
atgacttggt tgagtactca ccagtcacag aaaagcatct tacgcgatgg catgacagtaa  480
gagaattatg cagtgctgcc ataaccatga gtgataacac tgcggccaac ttacttctga   540
caacgatcgg aggaccgaag gagctaaccg cttttttgca caacatgggg gatcatgtaa   600
ctcgccttga tcgttgggaa ccggagctga atgaagccat accaaacgac gagcgtgaca   660
ccacgatgcc tgtagcaatg gcaacaacgt tgcgcaaact attaactggc gaactactta   720
ctctagcttc ccggcaacaa ttaatagact ggatggaggc ggataaagtt gcaggaccac   780
ttctgcgctc ggcccttccg gctggctggt ttattgctga taaatctgga gccggtgagc   840
gtgggtctcg cggtatcatt gcagcactgg ggccagatgg taagccctcc cgtatcgtag   900
ttatctacac gacggggagt caggcaacta tggatgaacg aaatagacag atcgctgaga   960
taggtgcctc actgattaag cattggtaac tgtcagacca agtttactca tatatacttt   1020
agattgattt aaaacttcat ttttaattta aaaggatcta ggtgaagatc cttttttgata  1080
atctcatgac caaaatccct taacgtgagt tttcgttcca ctgagcgtca gacccgtag    1140
aaaagatcaa aggatcttct tgagatcctt ttttctgcg cgtaatctgc tgcttgcaaa    1200
caaaaaaacc accgctacca gcggtggttt gtttgccgga tcaagagcta ccaactcttt   1260
ttccgaaggt aactggcttc agcagagcgc agataccaaa tactgtcctt ctagtgtagc   1320
cgtagttagg ccaccacttc aagaactctg tagcaccgcc tacataccct gctctgctaa   1380
tcctgttacc agtggctgct gccagtggcg ataagtcgtg tcttaccggg ttggactcaa   1440
gacgatagtt accggataag cgcagcggt cgggctgaac ggggggttcg tgcacacagc    1500
ccagcttgga gcgaacgacc tacaccgaac tgagatacct acagcgtgag ctatgagaaa   1560
gcgccacgct tcccgaaggg agaaaggcgg acaggtatcc ggtaagcggc agggtcggaa   1620
caggagacg cacgagggag cttccagggg gaaacgcctg gtatctttat agtcctgtcg    1680
ggtttcgcca cctctgactt gagcgtcgat ttttgtgatg ctcgtcaggg gggcggagcc   1740
tatgaaaaa cgccagcaac gcggcctttt tacggttcct ggccttttgc tggccttttg    1800
ctcacatgtt ctttcctgcg ttatcccctg attctgtgga taaccgtatt accgcctttg   1860
agtgagctga taccgctcgc cgcagccgaa cgaccgagcg cagcgagtca gtgagcgagg   1920
aagcggaaga gcgcccaata cgcaaaccgc ctctccccgc gcgttggccg attcattaat   1980
gcagctggca cgacaggttt cccgactgga aagcgggcag tgagcgcaac gcaattaatg   2040
tgagttagct cactcattag gcaccccagg ctttacactt tatgcttccg gctcgtatgt   2100
tgtgtggaat tgtgagcgga taacaatttc acacaggaaa cagctatgac catgattacg   2160
ccaagcgcgc aattaaccct cactaaaggg aacaaaagct gggtaccggg ccccccctcg   2220
aggtcgacgg tatcgataag cttgatatcg aattgacgtg aattcttccc atgattcctt   2280
catatttgca tatacgatac aaggctgtta gagagataat tggaattaat ttgactgtaa   2340
acacaaagat attagtacaa aatacgtgac gtagaaagta ataatttctt gggtagtttg   2400
cagttttaaa attatgtttt aaaatgact atcatatgct taccgtaact tgaaagtatt   2460
tcgatttctt ggctttatat atcttgtgga aaggacgtgg atgtgttgtt tgtgtgatac   2520
tataaagttg gtagattgtg actggcttaa aaaatcatta attaataata ggttatgttt   2580
agagtgttcc ccgcgccagc ggggataaac cgtccaatct atgacatcaa ttattataca   2640
tcgggtgttc cccgcgccag cggggataaa ccgttttttg aattcctgca gcccgggggat  2700
tccactagtt ctagagcggc cgccaccgcg gtggagctcc aattcgccct atagtgagtc   2760
gtattacgcg cgctcactgg ccgtcgtttt acaacgtcgt gactgggaaa accctggcgt   2820
tacccaactt aatcgccttg cagcacatcc ccctttcgcc agctggcgta atagcgaaga   2880
ggcccgcacc gatcgccctt cccaacagtt gcgcagcctg aatggcgaat gggacgcgcc   2940
ctgtagcggc gcattaagcg cggcgggtgt ggtggttacg cgcagcgtga ccgctacact   3000
tgccagcgcc ctagcgcccg ctcctttcgc tttcttccct tcctttctcg ccacgttcgc   3060
cggctttccc cgtcaagctc taaatcgggg gctcccttta gggttccgat ttagtgcttt   3120
acggcacctc gaccccaaaa aacttgatta gggtgatggt tcacgtagtg gccatcgcc    3180
ctgatagacg gtttttcgcc ctttgacgtt ggagtccacg ttctttaata gtggactctt   3240
gttccaaact ggaacaacac tcaaccctat ctcggtctat tcttttgatt tataagggat   3300
tttgccgatt tcggcctatt ggttaaaaaa tgagctgatt taacaaaaat ttaacgcgaa   3360
ttttaacaaa atattaacgc ttacaattta g                                  3391

SEQ ID NO: 34           moltype = DNA   length = 3391
FEATURE                 Location/Qualifiers
```

```
                      -continued
misc_feature       1..3391
                   note = Synthetic sequence, crRNA vector (E. coli)
source             1..3391
                   mol_type = other DNA
                   organism = synthetic construct
SEQUENCE: 34
gtggcactttt  tcggggaaat  gtgcgcggaa  cccctatttg  tttattttc   taaatacatt   60
caaatatgta   tccgctcatg  agacaataac  cctgataaat  gcttcaataa  tattgaaaaa  120
ggaagagtat   gagtattcaa  catttccgtg  tcgcccttat  tcccttttt   gcggcatttt  180
gccttcctgt   ttttgctcac  ccagaaacgc  tggtgaaagt  aaaagatgct  gaagatcagt  240
tgggtgcacg   agtgggttac  atcgaactgg  atctcaacag  cggtaagatc  cttgagagtt  300
ttcgccccga   agaacgtttt  ccaatgatga  gcacttttaa  agttctgcta  tgtggcgcgg  360
tattatcccg   tattgacgcc  gggcaagagc  aactcggtcg  ccgcatacac  tattctcaga  420
atgacttggt   tgagtactca  ccagtcacag  aaaagcatct  tacggatggc  atgacagtaa  480
gagaattatg   cagtgctgcc  ataaccatga  gtgataacac  tgcggccaac  ttacttctga  540
caacgatcgg   aggaccgaag  gagctaaccg  cttttttgca  caacatgggg  gatcatgtaa  600
ctcgccttga   tcgttgggaa  ccggagctga  atgaagccat  accaaacgac  gagcgtgaca  660
ccacgatgcc   tgtagcaatg  gcaacaacgt  tgcgcaaact  attaactggc  gaactactta  720
ctctagcttc   ccgcaacaa   ttaatagact  ggatggaggc  ggataaagtt  gcaggaccac  780
ttctgcgctc   ggcccttccg  gctggctggt  ttattgctga  taaatctgga  gccggtgagc  840
gtgggtctcg   cggtatcatt  gcagcactgg  ggccagatgg  taagccctcc  cgtatcgtag  900
ttatctcacac  gacgggggagt  caggcaacta  tggatgaacg  aaatagacag  atcgctgaga  960
taggtgcctc   actgattaag  cattggtaac  tgtcagacca  agtttactca  tatatacttt  1020
agattgattt   aaaacttcat  ttttaattta  aaaggatcta  ggtgaagatc  cttttttgata  1080
atctcatgac   caaaatccct  taacgtgagt  tttcgttcca  ctgagcgtca  gaccccgtag  1140
aaaagatcaa   aggatcttct  tgagatcctt  ttttctgcg   cgtaatctgc  tgcttgcaaa  1200
caaaaaaacc   accgctacca  gcggtggttt  gtttgccgga  tcaagagcta  ccaactcttt  1260
ttccgaaggt   aactggcttc  agcagagcgc  agataccaaa  tactgtcctt  ctagtgtagc  1320
cgtagttagg   ccaccacttc  aagaactctg  tagcaccgcc  tacatacctc  gctctgctaa  1380
tcctgttacc   agtggctgct  gccagtggcg  ataagtcgtg  tcttaccggg  ttggactcaa  1440
gacgatagtt   accggataag  gcgcagcggt  cgggctgaac  ggggggttcg  tgcacacagc  1500
ccagcttgga   gcgaacgacc  tacaccgaac  tgagatacct  acagcgtgag  ctatgagaaa  1560
gcgccacgct   tcccgaaggg  agaaaggcgg  acaggtatcc  ggtaagcggc  agggtcggaa  1620
caggagacg    cacgagggag  cttccagggg  gaaacgcctg  gtatctttat  agtcctgtcg  1680
ggtttcgcca   cctctgactt  gagcgtcgat  ttttgtgatg  ctcgtcaggg  gggcggagcc  1740
tatgaaaaaa   cgccagcaac  gcggcctttt  tacggttcct  ggccttttgc  tggccttttg  1800
ctcacatgtt   ctttcctgcg  ttatcccctg  attctgtgga  taaccgtatt  accgcctttg  1860
agtgagctga   taccgctcgc  cgcagccgaa  cgaccgagcg  cagcgagtca  gtgagcgagg  1920
aagcggaaga   gcgcccaata  cgcaaaccgc  ctctccccgc  gcgttggccg  attcattaat  1980
gcagctggca   cgacaggttt  cccgactgga  aagcgggcag  tgagcgcaac  gcaattaatg  2040
tgagttagct   cactcattag  gcaccccagg  ctttacactt  tatgcttccg  gctcgtatgt  2100
tgtgtggaat   tgtgagcgga  taacaatttc  acacaggaaa  cagctatgac  catgattacg  2160
ccaagcgcgc   aattaaccct  cactaaaggg  aacaaaagct  gggtaccggg  ccccccctcg  2220
aggtcgacgg   tatcgataag  cttgatatcg  aattgacgtg  aattcttccc  atgattcctt  2280
catatttgca   tatacgatac  aaggctgtta  gagagataat  tggaattaat  ttgactgtaa  2340
acacaaagat   attagtacaa  aatacgtgac  gtagaaagta  ataatttctt  gggtagtttg  2400
cagtttaaa    atatgtttt   aaaatgact   atcatatgct  taccgtaact  tgaaagtatt  2460
tcgatttctt   ggctttatat  atcttgtgga  aaggacgtgg  atgtgttgtt  tgtgtgatac  2520
tataaagttg   gtagattgtg  actggcttaa  aaaatcatta  attaataata  ggttatgttt  2580
agagtgttcc   ccgcgccagc  ggggataaac  cgagcacaaa  tatcatgct   caaaccactt  2640
acgggtgctc   cccgcgccag  cggggataaa  ccgttttttg  aattcctgca  gcccggggga  2700
tccactagtt   ctagagcggc  cgccaccgcg  gtggagctcc  aattcgccct  atagtgagtc  2760
gtattacgcg   cgctcactgg  ccgtcgtttt  acaacgtcgt  gactgggaaa  accctggcgt  2820
tacccaactt   aatcgccttg  cagcacatcc  ccctttcgcc  agctggcgta  atagcgaaga  2880
ggcccgcacc   gatcgccctt  cccaacagtt  gcgcagcctg  aatggcgaat  gggacgcgcc  2940
ctgtagcggc   gcattaagcg  cggcgggtgt  ggtggttacg  cgcagcgtga  ccgctacact  3000
tgccagcgcc   ctagcgcccg  ctcctttcgc  tttcttccct  tcctttctcg  ccacgttcgc  3060
cggctttccc   cgtcaagctc  taaatcgggg  gctcccttta  gggttccgat  ttagtgcttt  3120
acggcacctc   gaccccaaaa  aacttgatta  gggtgatggt  tcacgtagtg  ggccatcgcc  3180
ctgatagacg   gtttttcgcc  ctttgacgtt  ggagtccacg  ttctttaata  gtggactctt  3240
gttccaaact   ggaacaacac  tcaacccta   ctcggtctat  tcttttgatt  tataagggat  3300
tttgccgatt   tcggcctatt  ggttaaaaaa  tgagctgatt  taacaaaaat  ttaacgcgaa  3360
ttttaacaaa   atattaacgc  ttacaattta  g                                   3391

SEQ ID NO: 35       moltype = DNA  length = 3391
FEATURE            Location/Qualifiers
misc_feature       1..3391
                   note = Synthetic sequence, crRNA vector (EMX1)
source             1..3391
                   mol_type = other DNA
                   organism = synthetic construct
SEQUENCE: 35
gtggcactttt  tcggggaaat  gtgcgcggaa  cccctatttg  tttattttc   taaatacatt   60
caaatatgta   tccgctcatg  agacaataac  cctgataaat  gcttcaataa  tattgaaaaa  120
ggaagagtat   gagtattcaa  catttccgtg  tcgcccttat  tcccttttt   gcggcatttt  180
gccttcctgt   ttttgctcac  ccagaaacgc  tggtgaaagt  aaaagatgct  gaagatcagt  240
tgggtgcacg   agtgggttac  atcgaactgg  atctcaacag  cggtaagatc  cttgagagtt  300
ttcgccccga   agaacgtttt  ccaatgatga  gcacttttaa  agttctgcta  tgtggcgcgg  360
tattatcccg   tattgacgcc  gggcaagagc  aactcggtcg  ccgcatacac  tattctcaga  420
```

```
atgacttggt tgagtactca ccagtcacag aaaagcatct tacgcatggc atgacagtaa   480
gagaattatg cagtgctgcc ataaccatga gtgataacac tgcggccaac ttacttctga   540
caacgatcgg aggaccgaag gagctaaccg ctttttttgca caacatgggg gatcatgtaa  600
ctcgccttga tcgttgggaa ccggagctga atgaagccat accaaacgac gagcgtgaca   660
ccacgatgcc tgtagcaatg gcaacaacgt tgcgcaaact attaactgac tgcactacta   720
ctctagcttc ccgcaacaa ttaatagact ggatggaggc ggataaagtt gcaggaccac    780
ttctgcgctc ggcccttccg gctggctggt ttattgctga taaatctgga gccggtgagc   840
gtgggtctcg cggtatcatt gcagcactgg ggccagatgg taagccctcc cgtatcgtag   900
ttatctacac gacggggagt caggcaacta tggatgaacg aaatagacag atcgctgaga   960
taggtgcctc actgattaag cattggtaac tgtcagacca agtttactca tatatacttt  1020
agattgattt aaaacttcat ttttaattta aaaggatcta ggtgaagatc cttttttgata 1080
atctcatgac caaaatccct taacgtgagt tttcgttcca ctgagcgtca gaccccgtag  1140
aaaagatcaa aggatcttct tgagatcctt ttttctgcg cgtaatctgc tgcttgcaaa   1200
caaaaaaacc accgctacca gcggtggttt gtttgccgga tcaagagcta ccaactcttt  1260
ttccgaaggt aactggcttc agcagagcgc agataccaaa tactgtcctt ctagtgtagc  1320
cgtagttagg ccaccacttc aagaactctg tagcaccgcc tacatacctc gctctgctaa  1380
tcctgttacc agtggctgct gccagtggcg ataagtcgtg tcttaccggg ttggactcaa  1440
gacgatagtt accggataag gcgcagcggt cgggctgaac ggggggttcg tgcacacagc  1500
ccagcttgga gcgaacgacc tacaccgaac tgagatacct acagcgtgag ctatgagaaa  1560
gcgccacgct tcccgaaggg agaaaggcgg acaggtatcc ggtaagcggc agggtcggaa  1620
caggagagcg cacgagggag cttccagggg gaaacgcctg gtatctttat agtcctgtcg  1680
ggtttcgcca cctctgactt gagcgtcgat ttttgtgatg ctcgtcaggg gggcggagcc  1740
tatgaaaaa cgccagcaac gcggccttttt tacggttccg gcctttttgc tggccttttg   1800
ctcacatgtt ctttcctgcg ttatcccctg attctgtgga taaccgtatt accgcctttg  1860
agtgagctga taccgctcgc cgcagccgaa cgaccgagcg cagcgagtca gtgagcgagg  1920
aagcggaaga gcgcccaata cgcaaaccgc ctctccccgc gcgttggccg attcattaat  1980
gcagctggca cgacaggttt cccgactgga aagcgggcag tgagcgcaac gcaattaatg  2040
tgagttagct cactcattag gcaccccagg ctttacactt tatgcttccg gctcgtatgt  2100
tgtgtggaat tgtgagcgga taacaatttc acacaggaaa cagctatgac catgattacg  2160
ccaagcgca aattaaccct cactaaaggg aacaaaagct gggtaccggg ccccccctcg   2220
aggtcgacgg tatcgataag cttgatatcg aattgacgtg aattcttccc atgattcctt  2280
catatttgca tatacgatac aaggctgtta gagagataat tggaattaat ttgactgtaa  2340
acacaaagat attagtacaa aatacgtgac gtagaaagta ataatttctt gggtagtttg  2400
cagttttaaa attatgtttt aaaatggact atcatatgct taccgtaact tgaaagtatt  2460
tcgatttctt ggctttatat atcttgtgga aaggacgtgg atgtgttgtt tgtgtgatac  2520
tataaagttg gtagattgtg actggcttaa aaaatcatta attaataata ggttatgttt  2580
agagtgttcc ccgcgccagc ggggataaac cgcaggccaa tggggaggac atcgatgtca  2640
cctcgtgttc ccgcgccag cggggataaa ccgtttttg aattcctgca gcccggggga   2700
tccactagtt ctagagcggc cgccaccgcg gtggagctcc aattcgccct atagtgagtc  2760
gtattacgcg cgctcactgg ccgtcgtttt acaacgtcgt gactgggaaa acctggcgt   2820
tacccaactt aatcgccttg cagcacatcc ccctttcgcc agctggcgta atagcgaaga  2880
ggcccgcacc gatcgccctt cccaacagtt gcgcagcctg aatggcgaat gggacgcgcc  2940
ctgtagcggc gcattaagcg cggcgggtgt ggtggttacg cgcagcgtga ccgctacact  3000
tgccagcgcc ctagcgcccg ctcctttcgc tttcttccct tcctttctcg ccacgttcgc  3060
cggctttccc cgtcaagctc taaatcgggg gctcccttta gggttccgat ttagtgcttt  3120
acggcacctc gaccccaaaa aacttgatta gggtgatggt tcacgtagtg gccatcgcc   3180
ctgatagacg gttttcgcc ctttgacgtt ggagtccacg ttctttaata gtggactctt  3240
gttccaaact ggaacaacac tcaacctat ctcggtctat tcttttgatt tataaaggat    3300
tttgccgatt tcggcctatt ggttaaaaaa tgagctgatt taacaaaaat ttaacgcgaa  3360
ttttaacaaa atattaacgc ttacaattta g                                 3391

SEQ ID NO: 36         moltype = DNA   length = 61
FEATURE               Location/Qualifiers
misc_feature          1..61
                      note = Synthetic sequence, primer1 (Cse1)
source                1..61
                      mol_type = other DNA
                      organism = synthetic construct
SEQUENCE: 36
gcaaagaatt cagatctcca ccatgcctaa gaagaagaga aaagtgaacc tgctgattga   60
c                                                                  61

SEQ ID NO: 37         moltype = DNA   length = 49
FEATURE               Location/Qualifiers
misc_feature          1..49
                      note = Synthetic sequence, primer2 (Cse1)
source                1..49
                      mol_type = other DNA
                      organism = synthetic construct
SEQUENCE: 37
tcatcgatgc atctcgagtt atccattaga aggtcctccc tgtggcttc               49

SEQ ID NO: 38         moltype = DNA   length = 61
FEATURE               Location/Qualifiers
misc_feature          1..61
                      note = Synthetic sequence, primer1 (Cse2)
source                1..61
                      mol_type = other DNA
                      organism = synthetic construct
```

```
SEQUENCE: 38
gcaaagaatt cagatctcca ccatgcccaa gaagaagcgg aaggtggccg atgagatcga    60
c                                                                   61

SEQ ID NO: 39           moltype = DNA   length = 49
FEATURE                 Location/Qualifiers
misc_feature            1..49
                        note = Synthetic sequence, primer2 (Cse2)
source                  1..49
                        mol_type = other DNA
                        organism = synthetic construct
SEQUENCE: 39
tcatcgatgc atctcgagtt aggcgttctt atttgtggtc agcacgaag               49

SEQ ID NO: 40           moltype = DNA   length = 61
FEATURE                 Location/Qualifiers
misc_feature            1..61
                        note = Synthetic sequence, primer1 (Cas5)
source                  1..61
                        mol_type = other DNA
                        organism = synthetic construct
SEQUENCE: 40
gcaaagaatt cagatctcca ccatgcccaa gaagaagcgg aaggtgtcca atttcatcaa    60
c                                                                   61

SEQ ID NO: 41           moltype = DNA   length = 49
FEATURE                 Location/Qualifiers
misc_feature            1..49
                        note = Synthetic sequence, primer2 (Cas5)
source                  1..49
                        mol_type = other DNA
                        organism = synthetic construct
SEQUENCE: 41
tcatcgatgc atctcgagtt atgcctctcc attgttccgc acccagctc               49

SEQ ID NO: 42           moltype = DNA   length = 61
FEATURE                 Location/Qualifiers
misc_feature            1..61
                        note = Synthetic sequence, primer1 (Cas6)
source                  1..61
                        mol_type = other DNA
                        organism = synthetic construct
SEQUENCE: 42
gcaaagaatt cagatctcca ccatgcccaa gaagaagcgg aaagtgtacc tgagcaaagt    60
g                                                                   61

SEQ ID NO: 43           moltype = DNA   length = 47
FEATURE                 Location/Qualifiers
misc_feature            1..47
                        note = Synthetic sequence, primer2 (Cas6)
source                  1..47
                        mol_type = other DNA
                        organism = synthetic construct
SEQUENCE: 43
tcatcgatgc atctcgagtt acagaggtgc cagtgacagc agcccac                 47

SEQ ID NO: 44           moltype = DNA   length = 61
FEATURE                 Location/Qualifiers
misc_feature            1..61
                        note = Synthetic sequence, primer1 (Cas7)
source                  1..61
                        mol_type = other DNA
                        organism = synthetic construct
SEQUENCE: 44
gcaaagaatt cagatctcca ccatgcccaa gaagaagcgg aaggtgcgct cctacctgat    60
c                                                                   61

SEQ ID NO: 45           moltype = DNA   length = 49
FEATURE                 Location/Qualifiers
misc_feature            1..49
                        note = Synthetic sequence, primer2 (Cas7)
source                  1..49
                        mol_type = other DNA
                        organism = synthetic construct
SEQUENCE: 45
tcatcgatgc atctcgagtt actggctcac gtccattcct cccttgatc               49

SEQ ID NO: 46           moltype = DNA   length = 6265
FEATURE                 Location/Qualifiers
```

| source | 1..6265 |
| | mol_type = unassigned DNA |
| | organism = Homo sapiens |

SEQUENCE: 46

```
tcaccaaccg ccaagagagc ttgatatgac tgtatatagt atagtcataa agaacctgaa    60
cttgaccata tactctatgtc atgtggaaaa tttctcatag cttcagatag attatatctg   120
gagtgaagaa tcctgccacc tatgtatctg gcatagtgtg agtcctcata aatgcttact   180
ggtttgaagg gcaacaaaat agtgaacaga gtgaaaatcc ccactaagat cctgggtcca   240
gaaaaagatg ggaaacctgt ttagctcacc cgtgagccca tagttaaaac tctttagaca   300
acaggttgtt tccgtttaca gagaacaata atattgggtg gtgagcatct gtgtggggt    360
tggggtggga taggggatac ggggagagtg gagaaaaagg ggacacaggg ttaatgtgaa   420
gtccaggatc cccctctaca tttaaagttg gtttaagttg gctttaatta atagcaactc   480
ttaagataat cagaattttc ttaaccttt agccttactg ttgaaaagcc ctgtgatctt    540
gtacaaatca tttgcttctt ggatagtaat ttcttttact aaaatgtggg cttttgacta   600
gatgaatgta aatgttcttc tagctctgat atcctttatt cttatatttt tctaacagat   660
tctgtgtagt gggatgagca gagaacaaaa acaaataat ccagtgagaa aagcccgtaa    720
ataaccttc agaccagaga tctattctct agcttatttt aagctcaact taaaagaag    780
aactgttctc tgattctttt cgccttcaat acacttaatg atttaactcc accctccttc   840
aaaagaaaca gcatttccta cttttatact gtctatatga ttgatttgca cagctcatct   900
ggccagaaga gctgagacat ccgttcccct acaagaaact ctccccggta agtaacctct   960
cagctgcttg gcctgttagt tagcttctga gatgagtaaa agactttaca ggaaacccat  1020
agaagacatt tggcaaacac caagtgctca tacaattact ttaaaatata atctttaaga  1080
taaggaaagg gtcacagttt ggaatgagtt tcagacggtt ataacatcaa agatacaaaa  1140
catgattgtg agtgaaagac tttaaaggga gcaatagtat tttaataact aacaatcctt  1200
acctctcaaa agaagatt gcagagagat gagtcttagc tgaaatcttg aaatcttatc  1260
ttctgtaag gagaactaaa ccctctccag tgagatgcct tctgaatatg tgcccacaag  1320
aagttgtgtc taagtctggt tctctttttt cttttcctc cagacaagag ggaagcctaa  1380
aaatggtcaa aattaatatt aaattacaaa cgccaaataa aatttcctc taatatatca   1440
gtttcatggc acagttagta tataattctt tatggttcaa aattaaaaat gagcttttct  1500
aggggcttct ctcagctgcc tagtctaagg tgcagggagt ttgagactca caggggtttaa 1560
taagagaaaa ttctcagcta gagcagctga acttaaatag actaggcaag acagctggtt  1620
ataagactaa actacccaga atgcatgaca ttcatctgtg gtggcagacg aaacattttt  1680
tattatatta tttcttgggt atgtatgaca actcttaatt gtggcaactc agaaactaca  1740
aacacaaact tcacagaaaa tgtgaggatt ttacaattgg ctgttgtcat ctatgacctt  1800
ccctgggact tgggcacccg gccatttcac tctgactaca tcatgtcacc aaacatctga  1860
tggtcttgcc ttttaattct ctttcgagg actgagaggg agggtagcat ggtagttaag  1920
agtgcaggct tccgcattc aaaatcggtt gcttactagc tgtgtggctt tgagcaagtt  1980
actcaccctc tctgtgcttc aaggtccttg tctgcaaaat gtgaaaaata ttcctgcct   2040
cataaggttg ccctaaggat taaatgaatg aatgggtatg atgcttagaa cagtgattgg  2100
catccagtat gtgccctcga ggcctcttaa ttattactgg cttgctcata gtgcatgttc  2160
tttgtgggct aactctagcg tcaataaaaa tgttaagact gagttgcagc cgggcatggt  2220
ggctcatgcc tgtaatccca gcattctagg aggctgaggc aggaggatcg cttgagccca  2280
ggagttcgag accagcctgg gcaacatagt gtgatcttgt atctataaaa ataaacaaaa  2340
ttagcttggt gtggtggcgc ctgtagtccc cagccacttg gagggtgag gtgagaggat  2400
tgcttgagcc cgggatggtc caggctgcag tgagccatga tcgtgccact gcactccagc  2460
ctgggcgaca gagtgagacc ctgtctcaca acaacaacaa caacaacaaa aaggctgagc  2520
tgcaccatgc ttgacccagt ttcttaaaat tgttgtcaaa gcttcattca ctccatggtg  2580
ctatagagca caagattta tttggtgaga tggtgctttc atgaattccc caacagagc   2640
caagctctcc atcagtggaa cagggaagct agcagcaaac cttccttca ctacaaaact  2700
tcattgcttg gccaaaaga gagttaattc aatgtagaca tctatgtagg caattaaaaa  2760
cctattgatg tataaaacag tttgcattca tggagggcaa ctaaatacat tctaggactt  2820
tataaaagat cactttttat ttatgcacag ggtggaacaa gatggattat caagtgtcaa  2880
gtccaatcta tgcatcaat tattatacat cggagccctg ccaaaaaatc aatgtgaagc   2940
aaatcgcagc ccgcctcctg cctccgctct actcactggt gttcatcttt ggttttgtgg  3000
gcaacatgct ggtcatcctc atcctgataa actgcaaaag gctgaagagc atgactgaca  3060
tctacctgct caacctggcc atctctgacc tgtttttcct tcttactgtc ccttctggg    3120
ctcactatgc tgccgcccag tgggactttg gaaatacaat gtgtcaactc ttgacagggc  3180
tctattttat aggcttcttc tctggaatct tcttcatcat cctcctgaca atcgataggt  3240
acctggctgt cgtccatgct cgtgttttgct taaaagccag gacggtcacc tttggggtgg  3300
tgacaagtgt gatcacttgg gtggtggctg tgtttgcgtc tctcccagga atcatcttta  3360
ccagatctca aaaagaaggt cttcattaca cctgcagctc tcattttcca tacagtcagt  3420
atcaattctg gaagaatttc cagacattaa agatagtcat cttggggctg gtcctgccgc  3480
tgcttgtcat ggtcatctgc tactcgggaa tcctaaaaac tctgcttcgg tgtcgaaatg  3540
agaagaagag gcacagggct gtgaggctta tcttcaccat catgattgtt tattttctct  3600
tctgggctcc ctacaacatt gtccttctcc tgaacacctt ccaggaattc tttgggctga  3660
ataattgcag tagctctaac aggttggacc aagctatgca ggtgacagag actcttggga  3720
tgacgcactg ctgcatcaac cccatcatct atgcctttgt cggggagaag ttcagaaact  3780
acctcttagt cttcttccaa aagcacattg ccaaacgctt ctgcaaatgc tgttctctatt  3840
tccagcaaga ggctcccgag cgagcaagct cagtttacac ccgatccact ggggagcagg  3900
aaatatctgt gggcttgtga cacgactca agtgggctgg tgacccagtc agagttgtgc   3960
acatggctta gttttcatac acagcctggg ctggggtgg ggtgggagag gtcttttta    4020
aaaggaagtt actgttatag agggtctaag attcatccat ttatttggca tctgtttaaa  4080
gtagattaga tcttttaagc ccatcaatta tagaaagcca aatcaaaata tgttgatgaa  4140
aaatagcaac cttttatct cccctteaca tgcatcaagt tattgacaaa ctctccctc    4200
actccgaaag ttccttatgt atatttaaaa gaaagcctca gagaattgct gattcttgag  4260
tttagtgatc tgaacagaaa taccaaaatt atttcagaaa tgtacaactt tttacctagt  4320
acaaggcaac ataggttg taaatgtgtt taaacaggt ctttgtcttg ctatggggag    4380
aaaagacatg aatatgatta gtaaagaaat gacactttc atgtgtgatt tccctccaa    4440
ggtatggtta ataagttca ctgacttaga accaggcgag agacttgtgg cctgggagag  4500
```

```
ctgggaagc ttcttaaatg agaaggaatt tgagttggat catctattgc tggcaaagac    4560
agaagcctca ctgcaagcac tgcatgggca agcttggctg tagaaggaga cagagctggt    4620
tgggaagaca tggggaggaa ggacaaggct agatcatgaa gaaccttgac ggcattgctc    4680
cgtctaagtc atgagctgag cagggagatc ctggttggtg ttgcagaagg tttactctgt    4740
ggccaaagga gggtcaggaa ggatgagcat ttagggcaag gagaccacca acagccctca    4800
ggtcagggtg aggatggcct ctgctaagct caaggcgtga ggatgggaag gagggaggta    4860
ttcgtaagga tgggaaggag ggaggtattc gtgcagcata tgaggatgca gagtcagcag    4920
aactggggtg gatttggggtt ggaagtgagg gtcagagagg agtcagagag aatccctagt    4980
cttccaagcag attggagaaa cccttgaaaa gacatcaagc acagaaggag gaggaggagg    5040
tttaggtcaa gaagaagatg gattggtgta aaaggatggg tctggtttgc agagcttgaa    5100
cacagtctca cccagactcc aggctgtctt tcactgaatg cttctgactt catagatttc    5160
cttccccatcc cagctgaaat actgaggggt ctccaggagg agactagatt tatgaataca    5220
cgaggtatga ggtctaggaa cataccttcag ctcacacatg agatctaggt gaggattgat    5280
tacctagtag tcatttcatg ggttgttggg aggattctat gaggcaacca caggcagcat    5340
ttagcacata ctacacattc aataagcatc aaactcttag ttactcattc agggatagca    5400
ctgagcaaag cattgagcaa aggggtccca tagaggtgag ggaagcctga aaaactaaga    5460
tgctgcctgc ccagtgcaca caagtgtagg tatcatttc tgcatttaac cgtcaatagg    5520
caaagggggg aagggacata ttcatttgga aataagctgc cttgagcctt aaaacccaca    5580
aaagtacaat ttaccagcct ccgtatttca gactgaatgg gggtggggggg ggcgccttag    5640
gtacttattc cagatgcctt ctccagacaa accagaagca acagaaaaaa tcgtctctcc    5700
ctcccttttga aatgaatata ccccttagtg tttgggtata ttcatttcaa agggagagag    5760
agaggttttt ttctgttctg tctcatatga ttgtgcacat acttgagact gttttgaatt    5820
tgggggatgg ctaaaaccat catagtacag gtaaggtagg ggaatagtaa gtggtgagaa    5880
ctactcaggg aatgaaggtg tcagaataat aagaggtgct actgactttc tcagcctctg    5940
aatatgaacg gtgagcattg tggctgtcag caggaagcaa cgaagggaaa tgtctttcct    6000
tttgctctta agttgtggag agtgcaacag tagcatagga ccctaccctc tgggcaagt    6060
caaagacatt ctgacatctt agtatttgca tattcttatg tatgtgaaag ttacaaattg    6120
cttgaaagaa aatatgcatc taataaaaaa caccttctaa aataattcat tatattcttg    6180
ctctttttcagt caagtgtaca tttagagaat agcacataaa actgccagag cattttataa    6240
gcagctgttt tcttccttag tgtgt                                           6265

SEQ ID NO: 47          moltype = DNA  length = 29
FEATURE                Location/Qualifiers
misc_feature           1..29
                       note = Synthetic sequence, primer1 (CCR5)
source                 1..29
                       mol_type = other DNA
                       organism = synthetic construct
SEQUENCE: 47
ccacttggag gggtgaggtg agaggattg                                       29

SEQ ID NO: 48          moltype = DNA  length = 25
FEATURE                Location/Qualifiers
misc_feature           1..25
                       note = Synthetic sequence, primer2 (CCR5)
source                 1..25
                       mol_type = other DNA
                       organism = synthetic construct
SEQUENCE: 48
taaagatgat tcctgggaga gacgc                                           25

SEQ ID NO: 49          moltype = DNA  length = 25545
FEATURE                Location/Qualifiers
source                 1..25545
                       mol_type = unassigned DNA
                       organism = Homo sapiens
SEQUENCE: 49
gcagtctttc tgccacagcc tcccaaagtg ctgagattat aggtgtgagc cattgtacct      60
ggcttggagt aatgttttg agcaaagcaa atgtacagga catgcacaga gaggcacagg     120
gagcacagag tccctggatg aatgctctgg ctggtgtcaca tattgtcaca gggcaggcta    180
cccaaaggtg agcagaacac atgaggctag acaggtacaa cttgctcatg aagagcctcg    240
aatgccaagc ttaggagttt gaactttatt ggaacactga cactaatagt taatgtttac    300
tgagtgctta ctatgtgcta agagctatgc atgaatcacc tcattctaat tctcttaact    360
ctccacagca ggtcttatta tttccagatt gctgatgaaa aactgagtca cagaggagta    420
aaaaaaaaaa aacaaaaaca ccctgggtcc agagttgtgt gaaaaaattt taacaggtta    480
gagttgtgtt gtagaaatct ggtagccagc cacgtgtaag acgaattgta gaaggagag    540
atcacaaatg gctatcataa gagaatcact gggaaaaggt aataagaacc caaattagag    600
gcaaggagaa cagaaagaaa tgaaagaatg caaagactga ctggatgtgc acagcagtga    660
ccgagagaaa ggaggtatca caggtgcctc ttagctgcaa agcctgggtg tcctgcagaa    720
agggcagct attatcagaa gagagaagcc agagagaggc acagatttgg tggggatgat    780
gttgagctcc gtttgggggt atggtgagtg tctagggggc ctgtaggaac ccctccagaa    840
aaattctcac aagcatttga aaatcagtga cttgatctgg agaaaatat agggctggca    900
ttacaaacct gccgggtct gcattacagt attggttgaa agtgtggaaa ttgataatga    960
gttgtttg gtagatacat agatagatag agatagagat agatagagat atagatagat   1020
agatagatag atagaataaa tagcatgata catggaatga gggaagggct aaggataaag   1080
atgccttcat ggatgcccac agttaggaga agaaaagtaga gcccatgaag gaacaactcc   1140
cagagttttgc agatccaggc aagtatcttg ttcagaaaat aaagggaagg gagtttccaa   1200
aagaaaggg ggttgaaggt actcagatgc tgaggagcct ataacaatt gtgactaaaa    1260
aagactcaaa tttggaaata aggtgtccta atgaacattt cagaggatgg agagagattc   1320
```

```
ttaaagtcag cctttggaag aataactata tagaacactt ccagaggcca aactagtgac  1380
aatggatcaa aagaattaaa atattgcata tctggaaatt acacagctag aaatatgtag  1440
aaaagaaaca caaacatgcg gtaagataca gctatggagc tgtttgtcga aattttgtta  1500
aaacagtgaa aatctgtaaa ctgtattaat gtccaacaat aaaaaatatt taatgagagg  1560
caaagatgct ttgattggtt ataaagataa agaagttaca atactatgta cagtatgatc  1620
cttttttttaa agggaggcac atatagaaag aactggaagg atatactgta agaatttcac  1680
gatgtttgtt tctgggtagt aggatttgac aattataaga tctctgtttt cccttcactc  1740
cccccttttg gattatctgt attttttata actctgtcca atagacatat aatgtgagac  1800
acataatttt aaatgttcta gtggccacat ttaaaaagta gaaagaaata gataaaataa  1860
tcttcttaag atatttcatt ttactcaata tatccattac tatgtgtaat cgatataaaa  1920
atattaatat tttaaatgtt ttagcactaa gcctgtttaa cactaaatgc agtggatatt  1980
cacatttaca gaacatctct gtttgggcca tccacttctc aagcaccaca ttaccgcatt  2040
tggctcctag cacggctcta tgaataataa gcagttaata tttatcaaaa gcctactatg  2100
ttccaggcac tgctccaagt tcatcaggtg gagattataa ctcattaggt ctcaataact  2160
ccatgaggtt gaacttattg tgctctccac aagcacgtgt tgcttgccct tgtcctcata  2220
ccataatgaa atgtttggag cttttgcaaa agccatttct ctaatatgat gggcatccaa  2280
gtctggttgc aaaggcttgg atagagggca agtgagagaa ttggagagag actaaaaatc  2340
attcaagaaa ttttgtggtg aaaaagacaa gtcaaaagac tgagagaaac atgaggacag  2400
aaaactcttt gtaaggcaag gagacataaa gatgaagtca ggctgaatag gaaagaagga  2460
ggtgaaaggt gaaagagaga tggctggggg tgtggctggt ccaaattctc acaagatctc  2520
tgttggagaa acattgcctg gcttgtgctg gtggcgagat gtacatagca gcttcccagc  2580
tagagggagc agggagtcat ggccttgtga gggagacaga tggagacaca cacaacccc  2640
atcgcaggtg aatgctatga aagaatgggg tggagggctt cccagggaga tgaactgagt  2700
tttaagaacg aagttagcca gcaaagaagc aaaaggaaga ggatagagac ttgaggatta  2760
catcactgga tgactgagcc actgattgga tgtggaggat gagagagtga tgctttgagg  2820
tgattcccaa gttctccgca tggacaaagg cagagacaat aacttgtact gagtgctctt  2880
tggagtctga cattgatcca gtgcaccaca tatgttatct catttactcc tcacagaggt  2940
cccgtataac gcttgcaatt tcacagatac gcaagctgag gcaaaataat tggcccaggg  3000
ctcaccacta ataaatagga gagtctggat ttggggccag gttattccag aaatagagag  3060
agggagggaa aacgttaatg tggggccaga gccagaacga gtaggctagg ctgtatcgcc  3120
ctgggaggca tcgggctatt ctccaaaaag tgaggctccg ggttgcagga gatgggacct  3180
ccaggaaact ggtgggaggc tggacagggg caaagtgaaa ggtaagcagc ctgaagatgg  3240
gtgggatgta gtggactcca gcgtgaagag cctccagtct ctggcagagc tcagcagctt  3300
gggtggagg aaacgaaggg cagggagcag aaggtggtgg ggggaacggg tttttggttaa  3360
gatgggcagc tgtccagtgg tgaagagggg aagtatttgt gtatacgtca agttgtgggg  3420
gatggtggta gagggagcag tatgagagtc tgggaggaac agggcagggg agatggcaca  3480
ggagaagatt ggggtggggg tgggggcact gatactgaat ccagtacaca gaggcaggct  3540
tagagacccc ctgagggtga caaattcttc tcttaacttg ctgcagagga aacgacaaga  3600
gaataggtcc taagaggagt gaaaatagag gaaactggcc aagggataaa gataagcaga  3660
gctatggaag aaaaggaaga aaattaggga attactggag aggaagctga cagaaagggg  3720
cgctgggaga ggaaaaggtg agggaggacg aaaacgaaac tcctatcacc cagcgcattc  3780
cagcaccccc tccccctccc ccgggaagtc tgcgactgca tcctcacagg gatggaatgg  3840
gagtggaagc taggccaggc tgggacccccg gggctgtccc agcccaacca agacggtgac  3900
cagactcaag ttactgatcc tccgctgttt cttcatctgt aaagtggagt taatgacaga  3960
cagctggatg tcaacgtttt ttgttgtttg ttttagagat gggatctccc tgtatcgccc  4020
aggctggagt gcagcggtat gatcacggct cactgcagcc tcgacctcct gggctcgaga  4080
gatcttcctg tctcagcctc ccgagtagaa atgtcagcat ttgaatgcct cacaagggaa  4140
ggtggtgtaa taaaaggtct attgatttag atatgaacaa gtatacccag agccacacga  4200
atgaaaggag gtgccagtg tagatgcaag tctaggacgg tcgtagatt ccaagcttct  4260
ctacctgccc agttaaacaa gttcgtggcc cctggccagc ctctcggtgg gggtctgcga  4320
cagaacgggt gggattcatt accaggctag gagcgcaagg ccctcgggcc gggttcagct  4380
tgctgggctc ctgtcttgtc tcagccccca gcacttgctc tgtcaccgca gagcacaggc  4440
ccaggcaacg tttacccaac tgaacccgca tcccgtgggg aaccttgttc caacaaaatc  4500
ccgtcgttgt ctccttccat atggaacgaa aatctccttc tgtacctctg cccagctccg  4560
caccccgcc cccttagaga tacggcctgg tcgggtcctg gtccccccct cggccggccg  4620
tccacttttc ccagactgag ggtggggaaa aggaggaggg ggaagaaatc agaggaggaa  4680
aagtcgggag gtaggggagc cgggagacag gagaggggga aaataaagag cctgagacac  4740
aaacgagagg aaaagaccat cacagaaagc tggaaatctc cggagaggcc agcgagaacc  4800
cgcgctcccc acggattcca tcattccttc cgaaggcgcc tctgcggtgt ctcagccgtg  4860
ccaggcccg ggttccag gacgcggagg agtgctgggt gcggccgcct cgcctcccca  4920
ccctggccg cccctcccca cctcgcccaa ggggccggga acggcgtcgg cgcgcggggg  4980
cttttcggag cagtcgagtg gaaaatagac tttaacccgc tttgtggcgg ccggggcgcc  5040
ctgagcgctc tccaaaccac ggctcccggc gctcaggcgg ccgctgcca agacccggcc  5100
tggagtcccc gcagagttgc gcggccacg gaccccgttg ccttggggcg tcaggaggcc  5160
caacccagat ctgcgcgccc aggcagcgct caggccgcta gaatggaccc cggcagcggc  5220
gaggaagcgg aactctctgc ggctcctctc ccgcagtgcg ccggcaaggt ccaggtccca  5280
gcctccccac cgccgcccgc gcctcctag gcctcggagc ggcgccttc tgcggcctcg  5340
aaggtggggt gggaaagttt ggggagtccc ggctctcaca gcctgtcgtg agaactgccc  5400
ccggggaatt cgtccgccgt acggaaaaac tggccggagc agactcgtcc gcggttccgc  5460
ggtcgcgggt ggaaggtgaa ggtcgaggga ggtcaggctg cttctgcgtg tcctgacggc  5520
tggcgtgttc tcttgagatg ggctcgggct acttggccag cttcaattta agccacagtg  5580
tctccgaggc cctgacctgg tccggcccgc cgacacttga gccccagag cctcagaaa  5640
ggcgaggggg tggatctccc agtgccgagg ccgccgtcc tggtccaagc cggtcgcggc  5700
accgtgtctg ggcactggag ctgcttccag cccggcgaac agctggaggg tggcagtggg  5760
accgctccgg cggcttctcc cgcgcagtgc cccgcctgcc cccttgtgaa gggagtgagc  5820
gtcccctttc cagagctgtc cccgtgaca tccagaaaac gcgaaacctc aggaacaagg  5880
tcgcagcttc agaccgcggc ccaggaggcc gatggtgggt gagtgggaga gtcccggaga  5940
gcaggggggc agagagctgg ttttcgggaa accaatgtg ttggaccca aacatccacc  6000
ctccgctcgg atccaagttc tctgagaact gaaacgacat cccgggacga atgggagagt  6060
```

```
taggctgagc tacacaccgg ggaggggagg gttggagttt agccccaagc ccttcggacg   6120
ccttcttcgg ctcccgcgtg ggttgagacg gcggcacggc caccagactc agctaaaggg   6180
cggagtcgcg aggagaagcc agtggcgagg ggaggaggag gcctggatct ccccgcgaag   6240
gctccagtcc ggcttttgcc tccgactgcg ggctccctcc ccaccgccg tccctcgccc    6300
cgcccgcgcc cgccccccac cttgggcag gtgagcgggca gccaatgggc gagcgcgggg   6360
caggtgcccg ctaactcgcg cctcgcagcg ctgggcggc gggctgggc agggcagtgc     6420
ggggacaccg ggggctgggg tcggtcccag cgggactccg aaaggaggga gacgagctca   6480
accctcgggc cttactggca gctcgcagcc tagcacggag cccgcgcctg tgcgggcgcc   6540
tggagctgcc cgctccgccg cagcagccgc cgcgcctggc cgtacgctgt ggccggaccc   6600
cgcggtcgct cgctcacaca ccctcgccg ctccgcgcct ggctcgcccg cggggccgca    6660
gcgcgagcgc gcgggcgggg gaggtgaggg gtgcgggcgg gtgtgcatgt gcctggctgg   6720
gtgcacaccc cgcaaggcgg cggcgccagg acgggagcg ctcccagag cccggctgcc     6780
tcgcacagct cccgcggctg cgaccatgtt ccagcccgcg ccaagcgcg gctttaccat    6840
agagtccttg gtgggcaagg actggcggcac cggcggggca actggcggg ggggcgcggg   6900
ctccccatctc ctggcggcgg ccgctccga ggaaccgctc cggcccacgg cgctcaacta   6960
ccctcacccc agcgcggccg aggcggcctt cgtgagtggc ttccctgccg cggccgccgc   7020
gggcgcgggc cgctcgctct acggtgggcc cgagctcgtg ttccccgagg ccatgaacca   7080
ccccgcgctg accgtgcatc cggcgcacca gctgggcgcc tcccgctgc agccccgca    7140
ctccttcttc ggcgcccagc accgggaccc tctccatttc tacccctggg tcctgcggaa   7200
ccgcttcttc ggccaccgct tccagggtga gtgtccacgc tgtgcccgcc gaggcggccg   7260
gccggcgccc gtgctgcggc gatgcggggg aggctcgggg gcgcgcgggg ctgtttagaa   7320
gttactgccg ggaaggctgc aggtccgcgg aggtagattc ccaggcaggg aagagctgtg   7380
cggcatccac ccgcgccttc gccgcgtagg tctccctccc aggaaagcag gtggagacct   7440
ccaggctttt ctagaaaata taccagttcg gacgcaagcc caggcgcgtc ctcggagcct   7500
gtgctggccc tcgccacagc ctgcccaatt ctctctccca gctgagccag tctcagacca   7560
gagtacaact cctcccgctc tcctccgcc cggcttaacc tgccaccacg cttctctcgc    7620
aagtccacca ccacctccga gacctcagcc ttcgctggcg cgtccgggcg ggggaaagtc   7680
cattcgcgtg ccccagctct gggggaagca aggggcagcag ggaggggcgaa tcggagagtt  7740
aatgttcagt gtggagggcc tggctgtctt gggatgtttc tcggcaacct tggcccgact   7800
tctccaagtc acacgtgcct ctcctaccca aggtggggaa ggtttgcagt aagcaaactg   7860
gcttccgccg ttgctcgccg ccttcggag ggagcccacc cggctgctgg aataccgagg    7920
acagttttcc cgggcagggg gcgggggcag agggcttta aggtcgtagc cagtccgaac    7980
cccggagttt gcatccagca atcggcttgc taataaagat cctccactgg ccctacacac   8040
acacacacac acacacacac acgtttcaat tatttgtctt tcccggagaa               8100
aagagagttg catttgttgg agttcgtttt cttccttgaa atttgttgga gtttgttttt   8160
ttcttttctt tttttttaaa ttttattta aagagtggcc ttgatttgta caggcatcac    8220
tttagtttcc agttttattt tgttagtgta gaccagacca cagccttgtg agaagggtct   8280
atggctcaga gctaggtaac ccggctttta gagaaacaaa tgaaagggac atggctggag   8340
cttcggagcc aggagctaat gtgacggtct gtagtctagg tctacagtca attagatgtt   8400
tggcacagtt gtttagataa taaaatgaaa attatctctt gacactttga cttttcacaga  8460
aaaccgcttt cccaggtccc gatttgtcag gcaatttttt cagtcccacc tggccaatag   8520
atgctgacct ggcagatacc acaaaaccag agaatgtaat tactagaata agaattgttg   8580
tgggtagcct tgcctcctct ttgaagattt caaagacttg cccaaatcca aatccgaaaa   8640
aacaaaaatg ctacaatgtc atctgccttg gcaagagtt tctgccactt aaaaataaat    8700
gtttactgat aacatgagga tatctttaaa attgagcaat ctaccctggt cctccgtggg   8760
ctcgatccga agcctgggtc tcgaaacctg gcgcccaggg gccgagttgt agttgggcg    8820
gtgtgtgagc ccgcggccg ccgcggccga ggggctgggg ggttggaggc ttgtggaggg    8880
ataggggctc ggaggagagg gcggggtcgt tcctaagtcc tgtggcctcc agccgttcag   8940
cttgtccgga gtcggcatcc tgggccgcac cctcggcttc gaatcagcc cctgacgcccc   9000
tccgcaccgc ggttcctgcc tccgggcgcc gagggccggg ggcgcctgga gagaaatcca   9060
gctccgcgtc tgagcgtctc cagtcaggcg aggcggataa atccttcgca aaaccctctt   9120
ggaaattgcc gccgcttcct gagccatcag tcccagcggg tacgttatcg agtagcacaa   9180
acagttggat ttttccctca agaaccgagt ctgacgcgg agatggagcc aagtgtggct    9240
gcattttcgg acccggaaat ccgttgggca ctgaaggact tttcgaaccc tgtagcgctg   9300
ttgcttcgcg gtccatcgtc gccgctgcag acggatgcgc tccccggcgg tctctacgcc   9360
tccagtcccg gccaggcctc tgggctggga gccgagccgt ctcggcccct ccggcgccgc   9420
gttttctaga gaaccgggtc tcagcgatgc tcatttcagc cccgtcttaa tgcaacaaac   9480
gaaaccccac acgaacgaaa aggaacatgt ctgcgctctc tgcgcagcgc ttgggcggcc   9540
cggtcccggc gcgcgggaaa gcggcgtctc cgctaaccga ggcgctggaa ggggaaaagc   9600
gaatgcggaa tcgtccagga ctccgaaggt cggggccgct cgcgagcacc gaagggagg    9660
agccgacgaa gaccaggagt gggccgcatt tcggtactgt ttccccgaga tcaggaactt   9720
tccgggtcta ggagcaacgc ctggaggggg ctgtagagac ccagccccc gggaccgca     9780
actacaatgg gccggagctt ctaaggtcgc ctttgttctg gcaggaggac ggggaatgag   9840
gttatctccg ccgcctgtcc tgcctctccc ctcctagcc ctagggcct ccgccccgcc    9900
gtccggccct gagccctgg ccgcggcgg cctctccagc gaagactgcg gctcgaagac     9960
tgcagctcgg acccgggtg cttcggatcc ctagctccca cctccagctc cctcattcct    10020
gggaatctct tgtgctagtt cccagccatt gccttgaagg ggcctaaaa gagtggctgt   10080
agaaaaatcg gaggggtagg gaagcaggga ggagaggggt attcatttcc ctagctccag   10140
ggacggctat accagtccct ttccactttg ctaactgtcc tagtccgaaa ctgacagcca   10200
gttctcacag cccagaatta ctgcgtccaa acaggccgca ccctagaccc aagtttgttc   10260
tgcccttgtg gtccaggcaa gggaaactga accccctggta ggggtggttc aggcctcctt  10320
cccacaggtc gggggggcggg gcggtacagg tacctgtgca cctaaggcat cacccttgtc  10380
tttgcagaaa catgtagcaa ttgatctgtt tctcaggatg ttggtgttg tactaaacat    10440
cctcttttcta acagggaaac ttccttattc ttttggaatc aaataacctg tcatcactta  10500
gcatcttgac tcatcctgca gtctcctgct tctctgtgat agggttagaa ggaccccttgt 10560
atttttgcac atgcatgtga atatacccctt taggacacat gctgtctacc acaactggac  10620
atgacaatga cctggggcca ttttctcagt aaggtagacc caaagcaacc tagcatcccc  10680
ctaaaataac cagacttgag gcaaaggggc atgtatgttg gtacagaagc ttgttgcctt   10740
catcctctca tctgggttta taaagacaaa cacagagcac tccaccacac aggtgactga   10800
```

```
catataccac ataattacaa aataatcact aagtcagaga cactgggca gactgcagac  10860
ctgcttcctc agcccacac tgcccttcac acctctgcct cctattcata cacacttacg  10920
gggctttcca cactgcagcc tcacttctga ccaacctggg ccagcccagc atctgaggcc  10980
aaaccctgcc aatgctggga tgagctaggc tttctctctc cctctctggt tcatttgtcc  11040
agaggaaacc actgttggga cttcacccag gttcataaca atgttgtttt ttgaagcaag  11100
ttattaacat taacaagaag catttgcttt ccacccacct ttccctggcc tacctcactg  11160
gccccacccc agagacttta atcttcctta ttccccacct ggagcaggct ccatattttt  11220
ctgcccttta ctcatctctg ccagaccacc tccctgacc atctgtctat tccactatcc  11280
caagtcaaac ttctcttcag tcggacctga gggccctaga tctgcgccac ttgaataatc  11340
aaatggggtg tccctcaccc atctccctgt gatgtggtcc caccattttt gtggctgcac  11400
agatccaacc agttgaaatt gataaggtga ctggagatta ttgactgacc ccttccaggc  11460
actagccccg caatcctagc aactctgttc cacagaaaac tccagcaaaa acttggcttc  11520
tttaggtaac caaagcccag agacttggag gaagtaaggt cagggagttt ccaccaacag  11580
agggacaaga acagttacct ggagagtttt agctacagca tctcaattat ctgcttttga  11640
ttcacttaca tagatgtttc cagagatggg agatgttaac tgaattatcc aggtgattgt  11700
cttagagcaa agcaacaggt caaatcaagt ccaaccagta gccatctctg aagaaattaa  11760
ttggatcagt caatcccaac agctaattct gtcaaaataa tccatctagg gttccgtgtt  11820
tttggtgcat caggaggctg ttatgtgccc ttacatgaga atccatgggt gattttgtca  11880
gggcctgtta tgagtctgtt agcatgtgca accaagccag agattgtgtg agggcctagt  11940
ggggtgttca ttgagacagg cgctgtgggt agaggcttgt tttggcattg atagtttctg  12000
acccccatctc ccctacccca gcttcatcca gtccagtgtt atcccttcct cctgcatgtg  12060
ggagctgagt ccctatgctg gccaacattt gctaaggagac agtcacactc taaaaatcct  12120
atacagtaga taggaaaaaa gacagtaggg aggctggaac atatatttac acacgcccat  12180
gcagaaacca atatatctat atctatatat attagagaga aagatgacat ctagatattt  12240
atacacatgt ttctttagca agggactatt cagggatgaa gcaggatgaa agcttttccc  12300
accagacagt acttggagtc tccagtgtgt gtgttggtag aggggggttgg gggcttaccc  12360
tagaggctgg gtctctggac cgccaaggcc tggggagag agaggtggag aaaggggaag  12420
aaggagcctg actttccact tccaggtgct gcctggacca ctgacctagc cactggccta  12480
tttatacccc ctgcaagaca gagctagagc gtgctggcag gagttttaa tgagttagta  12540
gcctgagcat tcagccgcaa gactagtgca agcaggtgtg aaggattgc tccttgtgta  12600
ccttctagtt cttgaatctg tgtttggcaa aggtgtgcct agcacccgc tgctcccctt  12660
atcacgttcc tgacccccag ccctgcctct accctgggtc ctcttggagg gagatgcttt  12720
gcgaccagtt aactgaaagc aaatcgttgg ggctggcggc cagggcagcg cccctgggaa  12780
agggcggaga aagagcgcca tggacttttc ttccccaccc cttggcctct tccgctgccc  12840
caggcattgt gaatgtgggt ccacgcctcg tccggcctgc cccatctctt ggcttaacag  12900
agggatctgg agagctgtta ttcccgcgct tccccgcgg agtgctctc gagtgcgggg  12960
aggtgttgcg gagggagtg gacttaggga aggggcggca aaagggcaaa gggagaaatg  13020
gcgtgtgtgt gcgtgtcaag gaatggagag ggcagggcgc ttgggagcag ggcgcgaggc  13080
caggctctgt tgggcccggg ctcacgcgcg cccttctctc tgtctgtacc tgcgtgtgtt  13140
gccgtcggcg gcggggccgc agccagcgac gtgcccagg acgggctgct tctgcacggc  13200
cccttcgcac gcaagcccaa gcggatccgc acggccttct cgcccctcgca gctgctgcgg  13260
ctggagcgcg ccttcgagaa gaaccactac gtggtgggcg ccgagcggaa gcagctggcc  13320
gcagtctcta gcctctccga gacgcaggta atcacccccg gtcgcggcct gccctgccc  13380
cggagcccgg gtgaggtga gggtgcgcgg gtgcaggaga ggccctgagc ccgcccagc  13440
ccagcccctgc tgggttccaa aaggcccca ttccccgcgg cgctgcgtc aagcccgtct  13500
ttagagcctc ttcctcgaga ctgcgtgcag cctgctgagc ccgcaggact tttgtcaagc  13560
gctaaagacc tagcaggagg cagagtaaat gcaaactgta tcccgagccc ggctcccaaa  13620
gctcctcacg gggggaccag gttccctgga ggaagcgggt cgcctcggga gcgggcagcg  13680
caggcagcac cgaggccact ggagctggct ccagccctgg cattcctgca gcccttttcc  13740
cgccactgtg tcggggcgct catagtcctg cggggagccg gtccgcactg gcttttgctgc  13800
tgttcctggg caaaactggc gggggccttgg ctgcccacca gccaggaggcg tctggggaga  13860
aagcccaggt gtcctcagac taccaacaga ggggcttaac cagggagggg ccagcccctg  13920
cttggggccc gagggttgct ctgatccggc ccaaggccggc tgatagggct gtggaagcca  13980
cggtgtgcgc gcgcagagca tctgagtggc ctgggcctgg tgggaaatag accccgggta  14040
ctcaggtgct tctctgaatc actggaaagg ctgtcgaatg gggagaaggaa taaactccaa  14100
cggcgcctgg gcttgaactg agtgaaatta acaattaccg tgtagtgttt ttgtaactga  14160
tcgttaattt aagggaaaaa attaagaaat tagatgaaag ttatagggag gtggatttgg  14220
gttcattgta agtagacttt gccataaata aatgctgcct gggatcactg cataagctct  14280
tggtccacc aggtccgacg tgttggagtg gggctcagcg acctcagcc tagctgctgc  14340
cctggaggtg gatttcagtc tctgcgtgcc ggccggctcc cagagttgcg agaggccggc  14400
tccgcggtct cccagctacc tcccggctga cttttcacct tccgctcccc tttcctccta  14460
gtctcgaccc tactacacca ccgtcccctc ccaagtcccg ggcagtgaga agatgcccgg  14520
catgggggc agcggagcc tccctttagc agccagagta ggaaggggc ttagtgaggg  14580
agcccagacc caaacttcat ccgcagcttt cttcggcgga ccttaccctc tcctccttca  14640
gtggcatttt ggcatctatt gtcgtcatat ctgtctgctg ccccacttaa tctacaaatc  14700
gctcacgggt cggaggcagg acccgtgcgt tttcagatgt actagctggg ctgttctaac  14760
tgcagggaaa aagcttacaa aacaagagtt aattttaaaa acgtttcaaa gaaagatgtg  14820
tttttaaaaa taagttaata aaataacact ccctttttcc tcctggcagt gtttttaaat  14880
tattgtttga aacaaggtgt cagtttaaga atggtgttta taattaactt catttaaaca  14940
gtaatattta ttaaatttta attgcagaac tgtaagaaaa caaaaatggt ttttaatcct  15000
accacccaca gattaacact tgttgaaata atgtcattgt ttttaaactt tcaattttt  15060
agctcagtga gagcattttt aattaactct cttttcaaact gaacctagct gcctgtcaat  15120
atttgctcct aacaatgcca gttagtaaac ggactgattg tttctttcat ttttattatg  15180
agacatttca acatatatt taaaacaaaa ccagatagaa taacataaac gatcctgct  15240
tcattaacta tcaaaactca gggctaatct tcttcccgtc tgtaaatgag ctgctttttg  15300
catatggtac aacaaaaaga atgaggggag gtttgagcct ggggaacctg ccgtggcagc  15360
ctgtccttcc aggtgaagac cctgagatgg agagatggtt tggacagagc ttcccaggtg  15420
ggcaaacacg attttaaata cctgcctccc tgctaactta ctgtgtaacc ctgggcaagt  15480
cacttaacct ctctgagctc tggtttcctc attgagaaaa tagttgttta atgattaaag  15540
```

```
gtacctcata tgagctcaaa taatattaat ccccatccct agtcccttcc ctttaaggta   15600
gtatgtcaga ttagtagcat aagaagatcc aaacctgtgt gtcctcttag tccagcgttc   15660
ttcctccctt atgcagtttc cgtcatcaac attgcctttc tgttgccctc ataacttatc   15720
atacggagcc aggctatata attagctact tctctatccg cctcttggta cttaccaggc   15780
aagcttacct gtcatttcca gctatcagct atttgtcaag catcagtcac ccccaacagc   15840
cccctgcca tgcatttcta ctgttaatat ctgtatctgt ctccagagct ctctaatctg   15900
tcccaccccg tagctgtttt acatctagcc atatacttct gtctgctctc attaaactgc   15960
ctccccaaaa ctggctaatt tatatttccg attttctatt agttatatgt tcttcctaac   16020
aataagaact atttacccat ttgttcatta tctttgtcat ctattttacc ttctgtgttt   16080
ccaccattca tctcaaactt catctccata gagctatttc gcaactgaca aacagtatat   16140
tcatatgtct ggtaatggtt atctattatt ggctctggct ttgtcttctc tctgggtctg   16200
ggcctcagtt tctgtatctg tgagattgaa tgacacaaat tccagggttt tttctagtgc   16260
tgagtttctg tgactcctct acattctact tctctgtgtt tctgtatact acctcctcca   16320
cattctcaga gctcaccaca caaccctgc ctatcatgat atgcatcaaa ctttgttgtt   16380
attacttaat tatctgccat gtccaaacat caatctgtag accagcagta tgcgtctctc   16440
agggagatct taaaatacag attcctgggt ttcacccagg agattctctt aggaagtcca   16500
ggatagggtg caggaaaaag tttaaaaaca gttatttggg tgatcatgat taataacagg   16560
cctgagcatc ttagctctgg gaggcagagg ccaagcctgt ctgtttctta caggacccag   16620
ctcagtgccc gggatggagt acatgctcaa taaacatgta ttgaattaat gagcacattt   16680
ctctttgccc atacaaatac acactaactt tatcagtcat tccccttgct ctctgctgtc   16740
attgctccct ccctgtccct ctccttctat cttttccttg tactttcaca gctgattgtt   16800
gatttagatt atgcatatac cagtttgtgg ataaaacttc tcggagggtt actcagatca   16860
gtgtgtgaat gagctcttaa tccagatctc agaagtctgt gcactcccca agctttagcc   16920
gggtgctagg aggtgggcaa cctgggtgac tctgtgtgtt tagtgggagt ggggtattcg   16980
tgctgggatg gccagtgcct caatctagga gatgagggaa gagccctggg caagggctag   17040
ttctcccttc aggttctaat gacttgttcc tcactgcttg ggtgccgccc tggagtatga   17100
ccaggaaggt accagtctaa gcttcagtcc tggtggctga ttgggcagac ctgggcctga   17160
gtcattgcag aggctcaagt ttaatgagta tgtgtaatgg gtgtgtgcaa catgtgtctg   17220
cccatgtggg gcaccaacgg gctttatgtg attgatgccc aaaggtcaga tgatagcata   17280
ggtacacatt agatgccatt aggcagtcat atgacatggg gtgcagcttg catgcttttg   17340
tgtgtgttcg tgtgtgtgtc ggggcaggg gtaagttagt tttaggggga gtgagagaaa   17400
gcacctggtt gctccaggct gatcaactgg tcagtgtttc cagctactcc ttctgctctg   17460
aacagatcag caggtgtttc ttgaccttgc ctggcttaga gtttagctga gcggtgaagg   17520
caaagggtac agaaacgtgg cctgtggctt tgaagatttc ttactgagtg atgaaggcta   17580
agtgcaaagc ttgcacattt gtgaaacatg cacaggaaga atgactaggg tcccctttga   17640
ggtcacagct gtgggctgag gggtgtcagg atagaaacgc ttgagaagat ggctccagga   17700
ggcctcagac ctgaagact tgggggatg cctaggatcc taggttggag ggaaagaagg   17760
gcaggggttg aggcaggcag atgaagatag agccaccatc ttggagccca agggcaggga   17820
gatcttggga ggcaggagtt acggtcacct gcctatggct ttttcccctc agaggcatgg   17880
aaaggaggat ttggagggtc cttttcctgct ctgaatgtt ctggccttag agggatggat   17940
aagagggga tatccaagtg acctgaattt tagggaaaaa tcaagagaca tttgttccta   18000
gctcacggtg tgtccacatc tcttctctaa gtcttggctt ttcttcaaga acttctgcat   18060
ctcatgttcc aggagtcctg tgtgggagga tgaggggag ataaaggaga ttagagtgt   18120
tctgtgagga gctgggacca acatgtcctg aggtcgaatct tatgatgtct ccctgagaga   18180
gacagaggaa gggtccaggc tgggctgaaa gaggaggaga cagggaggct tagggagatc   18240
atggttatgg ttggtgggga gctggaggtg acctcagctt actgaggtga aggttgaact   18300
tagcatggca ttgattgggc ttgaccttga gagtgggaac agcccacatg atcaaatgat   18360
aggaaatggg tccccaggga agagagaaag ctgaggggtg acttgactga tatctccagg   18420
ctcctgtcca ttctgggata tttgaaatct ttgaagacag gacacgtatt cacctgaaag   18480
tgtgcagggg cctggagcca cagacttttc catttgcagg agtggtgaaa aagaaggggat   18540
ccagactcg ttcattcaga atagcagatt atttccaaagt aaagtctgat tagttctgaa   18600
atatcggctg gagccatagt ttgcttgttt gttagttcat ttttcccttt gttcttgcat   18660
gcatgtcttc atttattaat gcatacattg atcagtcctc tagcaaactg atacattcat   18720
tcatccatag cagtttcacc ttcttcattc tgcctgactc aagccaaccc ttcttctgcc   18780
cagcagtagg tgtccctcct ccaacttccc ctaaaagtgg ccaatccaat ttaccatgg   18840
gaatattaaa aactggccct cttgcaaaag tgtccacaaa actaagaaaa agatccagtt   18900
tctccatcat tgagcactt tcaaagcctt tgctgattag aattctaccc ctcttctgtt   18960
cattttctcc tgttttccag gtctggccca ggtacctctt gcctagagca taggcttgtc   19020
cagccagatg actatacatga gaacatgtcc tctgggcagg gcactgggac taacataaca   19080
gtttggctct ccagtctcat agtctggtga ggaggcagac gtaaataaat aaattagtga   19140
acagtggggg tcactgttac tgagactggg aagaggtact aaggaactac aggcaggtga   19200
tggggcagga ccattaagga acatcaggac agggtcttga aggctaagga gagtattcca   19260
gggttggtaa gtcaggagaa tggagacttt tggaaggatg tggcctctga gaaactgaga   19320
tgttcacttc acagtgaaat gaggacttgg gagaccagaa ggacctctt gctacagcag   19380
agaggtcaga gtgggcaagg ggtcctccag ctaacattcc aactgtacct cggggcttag   19440
agaggaggtga gtagtgtgtt tgtgttgggg atggggaggc atgtgcagga cagatccagc   19500
ctccaagcca taccatatga cccagctcct ttccagggcc tgtttttctct agggaagggg   19560
ctctgaagga tccagagttg cctggctggg ttggagaggt catgaaatgt cactctcatc   19620
tcctaataca ctcagagccc agttccttt ctttttccaa gtaaaaaata actaccatta   19680
tcaataatct attaaggaaa attcagaaaa gtagaaagaa gaaagaaaca tcacccacac   19740
tttaggtata tttccttcta gtcttttttt cccgtgtgta gattttgttt ttctatggtt   19800
gtgatcacac tgtgccagcc ttgtgcatcc tggcgtttcc attaatgcta tgaagtcata   19860
agcactaccc tgttattgca gtctttgtaa acagcatctg gacactcagc ccaaggctgt   19920
tctccggaag atggccaggc tgcacaggga gagggtttat gtccctgcct ctagagagat   19980
gcctacttga ccccagtatt tttcatggag aaaattcca gaatcacctt tcacttgggt   20040
gccctaggaa gctgcctctg gcctatcctg tgcctgaagt cgccatccaa agctttcctt   20100
ctttgagcca gtgttgctag tcaagggcag catgctgggc ccgtcccact acaggccaat   20160
gtgaccgtca gtctccttcc tgaaggacac ttggaaatgc atgtggaaag aggaaggtac   20220
agaaaagggc ccccggtccc tggtactgcc cgcatcacct gacagtcacc ttcggccagc   20280
```

```
ccacttgggc ttctcaggaa tgacaccccg gccctgcatc tggccctgag tcacgcacag 20340
gaggcagggt gagctcaccc gcccactgac tggcacagtc atagcaggct ccagggtggg 20400
gggcagggc  caggctgctg ccaaatggtt gtgctgagaa ccacccaggg tccaggtggc 20460
cctgcgccca aagataggtg ggcttggagt ccagcagcct gtgcccagag cctctgccat 20520
cctccacggc cggcctaggt gagatgtgca ggctatgggc ttggaaatga gggagaatc  20580
cccttgccct cactccatcc atcgaggccg ggcaccaacc cttcctgggc cagctttcca 20640
gccctggct  ggctgctctg caggcactga atgccagctg ccccatccc  catgccagtg 20700
ctctaaaatc agtgctctca aacaagggca gatggcgcag tggaagttct ggcaagaggg 20760
gactgtgagg ggaagtcctg gggtaggtgg gacagagagg actgcctggg aagggtgtag 20820
gggcagcacc tcctgggcat gaaaccatct gcagggcaca ggggccaggc ctgcctctgc 20880
atgcactgct tggccttgtg gctaaggcct gtgctttacc cagttcctct ggagcaggag 20940
cagtctttct gaggcctgcc ctcagccctg cccagggttc aaggatctct cctcagcatc 21000
attgctgctg ccaaaaccaa gaggctaccc accattcctc acccgcaact ctgccacgca 21060
gcaccgtctg cacagctgca gttggccaca tccacttgct tttaaatgtg ctgtcatttc 21120
ctggaaacca tccaggcctt gtagcctgcc ctctgcacct cctccccaag ggggcctct  21180
ggagcaagaa tccaagaggt gccctggcag ctgcaagtgt ccccagaaca tttcctctat 21240
gcatgaagga ctgaagccca gaggggaag  ggacttagct gagaatcagt acccaggatc 21300
ctcctgccaa cgctgaagat ggtttgggtc tggcctgact ctgcaaagcc aagtaaagaa 21360
ccacggagtc agggagagtt gacagatgaa ggctttctcc acagcccaca agcactaagt 21420
ccagtccagg agccaggatg agcctcccag attatgcatg agaggacatt aagggctgtg 21480
tcctggacac tgaacagatg ctggaggagg agggaaaaga ggcttcctgg aggagatggc 21540
ttagaaccat agacctgccc tctgcctcat gcctcctcca tcatggagga tggttgtcca 21600
gtttctgttt gaaccccacc ccataccttg ccagggctct cactgccaga cacagaatag 21660
ggggctccct gggttcaaag tagagctcac ttctgtcccc tggcttctc  ctgactgttc 21720
cttgtgtgac ctgttcccac atctggatgg gctgcaggag ccagtgctgt ggggacagaa 21780
ggtctggagc tgcccgtgaa gggcagaatg ctgccctgca acccgcttcc tccctgctct 21840
tgtctgtcca aggagaatga ggtctcactg gtggatttcg gactaccctg aggagctggc 21900
acctgaggga caaggccccc cacctgccca gctccagcct ctgatgaggg gtgggagaga 21960
gctacatgag gttgctaaga aagcctccc  tgaaggagac cacacagtgt gtgaggttgg 22020
agtctctagc agcgggttct gtgccccag  ggatagtctg gctgtccagg cactgctctt 22080
gatataaaca ccacctccta gttatgaaac catgcccatt ctgcctctct gtatggaaaa 22140
gagcatgggg ctgccccgtg gggtggtgtc cactttaggc cctgtgggag atcatgggaa 22200
cccacgcagt gggtcatagg ctctctcatt tactactcac atccactctg tgaagaagcg 22260
attatgatct ctcctctaga aactcgtaga gtcccatgtc tgccggcttc cagagcctgc 22320
actcctccac cttggcttgg cttttgctgg gctagaggag ctaggatgca cagcagctgt 22380
gtgaccctttgttgagagg aacaggaaaa ccacccttct ctctggccca ctgtgtcctc 22440
ttcctgccct gccatcccct tctgtgaatg ttagacccat gggagcagct ggtcagaggg 22500
gaccccggcc tggggcccct aaccctatgt agcctcagtc ttcccatcag gctctcagct 22560
cagcctgagt gttgagccc  cagtggctgc tctgggggcc tcctgagttt ctcatctgtg 22620
ccctccctc  cctggcccag gtgaaggtgt ggttccagaa ccggaggaca aagtacaaac 22680
ggcagaagct ggaggaggaa gggcctgagt ccgagcagaa gaagaagggc tcccatcaca 22740
tcaaccggtg gcgcattgcc acgaagcagg ccaatgggga ggacatcgat gtcacctcca 22800
atgactaggg tgggcaacca caaacccacg agggcagagt gctgcttgct ggtggccagg 22860
ccctgcgctg ggcccaagct ggactctggc cactccctgg ccaggctttg gggaggcctg 22920
gagtcatggc cccacagggc ttgaagcccg gggccgccat tgacagaggg caagcaatg  22980
ggctggctga ggcctgggac cacttggcct tctcctcgga gagcctgcct gcctgggcgg 23040
gcccgcccgc caccgcagcc tcccagctgc tctccgtgtc tccaatctcc cttttgtttt 23100
gatgcatttc tgttttaatt tattttccag gcaccactgt agtttagtga tcccagtgt  23160
cccccttccc tatgggaata ataaaagtct ctctcttaat gacacgggca tccagctcca 23220
gccccagagc ctggggtggt agattccggc tctgagggcc agtgggggct ggtagagcaa 23280
acgcgttcag ggcctgggag cctgcggttgg ggtactggtg gaggggtca aggggtaattc 23340
attaactcct ctcttttgtt gggggaccct ggtctctacc tccagctcca cagcaggaga 23400
aacaggctag acatagggaa gggccatcct gtatcttgag ggaggacagg cccaggtctt 23460
tcttaacgta ttgagaggtg ggaatcaggc ccaggtagtt caatgggaga gggagagtgc 23520
ttccctctgc ctagagactc tggtggcttc tccagttgag gagaaaccag aggaaagggg 23580
aggattgggg tctgggggag ggaacaccat tcacaaaggc tgacggttcc agtccgaagt 23640
cgtgggccca ccaggatgct cacctgtcct ggagaaccg  ctgggcaggt tgagactgca 23700
gagacagggc ttaaggctga gcctgcaacc agtcccagt  gactcagggc ctcctcagcc 23760
caagaaagag caacgtgcca gggcccgctg agctcttgtg ttcacctgcc tttctgtttg 23820
tcccacttgt caggatgaag gtttcctgac aagcaaatct gcattcctaa gtcttttccct 23880
tacgacatcc agacccctct cttctcttctt cacctccat gtgctcatga aacctctgct 23940
ctttggcctc catgccacca ttctgccggt gctaatgaca gtcaccaacc acagtcactg 24000
gccaccccct tgtggccaaa ctcaaccact tcctgttggg ttcacctgct ccctgatctg 24060
ttggctatgc cctcctggat tctcccaccc cgctctgcct tcatttcggt agctctgact 24120
cctccttcag cctgagttca ttcagtgtga tccatgcctt gtcacctctg gccacccca  24180
ggtcagtcct tgctctccct gactcctcat tatgtccttt gccttgtggg gatcacatcc 24240
acttccagga cttctcttg  gctccctggc ctgtgtcttt agctgacctc tgctgagctg 24300
cagacccgtc aagccagctg cctgctccac ccctgcccc  tcagcacctc aaagcccata 24360
catccacagc cggacgcacc tacccctctg tgcttcctcca ggatcaccca cctcgacaaa 24420
cagcattaga catgtacaca gtttcccaag ctacaggaaa tctgggaatc ttcctcaagc 24480
ttcctctcct cttccccagc cccatccatt cccatctagt gggttgagtc tagactggct 24540
tcccaaccac acctccctaa tgcagcaccc ctacccccc  tgcccagctc cctctgccac 24600
cggcctggcc tgggccctgc tcctctaggg aggtttctgt gaatgtcaag gatgaggtcc 24660
acttcaaagg aggccctcca tgttgcagct aggtttctct tccttgccac caaacagggc 24720
agactcaccc ccttctgagc ccctttgccc catcttcttg ccttgctccc ggtacccttt 24780
gcttcagcat cccccatccct gtccctgagt gagccacagg ttttcctgt gctgtgcctt 24840
cgctcatgct gttcttccca cctggaatgt cgggtgcttg atcaatgtgg aactcactgg 24900
aaagatgtca gagacccagc cttgctgtct gggccacatg cagggatcca agcacacaag 24960
gtccttctgc tgggagcaca gacccaggtc ccactcgcac tctcagcgtc tctctcccac 25020
```

```
ctctgcccac ctcacttgtg tccagtcagt gctagaaacc aaagggcttt gtcccatccc   25080
aacacccct ctccctccat cagtcaggaa tgcattctgc acatcttgaa agtcctaaca    25140
tggataagtc cagattaacc cacatggcga ccctcactgc caagcaggtg ggatcacttc   25200
tgggagcaca catgcccagg tgtggaagga aggtgggagg aagagtcatc cttttggccc   25260
cagtggggga cagagaaagg ggtgagctgt tcctctcaag atcctgcctc acttggtagg   25320
gggagggggt ccaggaagat cacagcagag cacccctgt catccgaata aagggctgga    25380
agggacccaa ggaaacctgc cagtctcccg aggccaggcc tgcggggggc ggggcgggga   25440
gtccctgccg cactcccatc caccccccat gttgtgcctc tccctgcaga cggtaaatat   25500
tggtgttgtg acttcattaa taaaggcttc tgtgagcctg aaaaa                   25545
```

| | | |
|---|---|---|
| SEQ ID NO: 50 | moltype = DNA length = 30 | |
| FEATURE | Location/Qualifiers | |
| misc_feature | 1..30 | |
| | note = Synthetic sequence, primer1 (EMX1) | |
| source | 1..30 | |
| | mol_type = other DNA | |
| | organism = synthetic construct | |

```
SEQUENCE: 50
gggcttctcc tgactgttcc ttgtgtgacc                                    30
```

| | | |
|---|---|---|
| SEQ ID NO: 51 | moltype = DNA length = 30 | |
| FEATURE | Location/Qualifiers | |
| misc_feature | 1..30 | |
| | note = Synthetic sequence, primer2 (EMX1) | |
| source | 1..30 | |
| | mol_type = other DNA | |
| | organism = synthetic construct | |

```
SEQUENCE: 51
caggatggcc cttccctatg tctagcctgt                                    30
```

| | | |
|---|---|---|
| SEQ ID NO: 52 | moltype = AA length = 7 | |
| FEATURE | Location/Qualifiers | |
| REGION | 1..7 | |
| | note = Synthetic sequence, NLS (protein) | |
| source | 1..7 | |
| | mol_type = protein | |
| | organism = synthetic construct | |

```
SEQUENCE: 52
PKKKRKV                                                             7
```

| | | |
|---|---|---|
| SEQ ID NO: 53 | moltype = DNA length = 21 | |
| FEATURE | Location/Qualifiers | |
| misc_feature | 1..21 | |
| | note = Synthetic sequence, NLS (nucleotide) | |
| source | 1..21 | |
| | mol_type = other DNA | |
| | organism = synthetic construct | |

```
SEQUENCE: 53
cccaagaaga agcggaaggt g                                             21
```

| | | |
|---|---|---|
| SEQ ID NO: 54 | moltype = AA length = 19 | |
| FEATURE | Location/Qualifiers | |
| REGION | 1..19 | |
| | note = Synthetic sequence, BPNLS (protein) | |
| source | 1..19 | |
| | mol_type = protein | |
| | organism = synthetic construct | |

```
SEQUENCE: 54
KRTADGSEFE SPKKKRKVE                                                19
```

| | | |
|---|---|---|
| SEQ ID NO: 55 | moltype = DNA length = 57 | |
| FEATURE | Location/Qualifiers | |
| misc_feature | 1..57 | |
| | note = Synthetic sequence, BPNLS (nucleotide) | |
| source | 1..57 | |
| | mol_type = other DNA | |
| | organism = synthetic construct | |

```
SEQUENCE: 55
aagcggactg ctgatggcag tgaatttgag tccccaaaga agaagagaaa ggtggaa      57
```

| | | |
|---|---|---|
| SEQ ID NO: 56 | moltype = DNA length = 44 | |
| FEATURE | Location/Qualifiers | |
| misc_feature | 1..44 | |
| | note = Synthetic sequence, BPNLS insert upper | |
| source | 1..44 | |
| | mol_type = other DNA | |
| | organism = synthetic construct | |

```
SEQUENCE: 56
agatcttaat acgactcact atagggagag ccgccaccat ggcc                    44
```

```
SEQ ID NO: 57           moltype = DNA  length = 13
FEATURE                 Location/Qualifiers
misc_feature            1..13
                        note = Synthetic sequence, BPNLS insert lower
source                  1..13
                        mol_type = other DNA
                        organism = synthetic construct
SEQUENCE: 57
taatatcctc gag                                                        13

SEQ ID NO: 58           moltype = AA  length = 22
FEATURE                 Location/Qualifiers
REGION                  1..22
                        note = Synthetic sequence, 2A (protein)
source                  1..22
                        mol_type = protein
                        organism = synthetic construct
SEQUENCE: 58
GSGATNFSLL KQAGDVEENP GP                                              22

SEQ ID NO: 59           moltype = DNA  length = 66
FEATURE                 Location/Qualifiers
misc_feature            1..66
                        note = Synthetic sequence, 2A (nucleotide Cse1-Cse2)
source                  1..66
                        mol_type = other DNA
                        organism = synthetic construct
SEQUENCE: 59
ggaagcggag caaccaactt cagcctgctg aagcaggccg gcgatgtgga ggagaatcca     60
ggcccc                                                                66

SEQ ID NO: 60           moltype = DNA  length = 66
FEATURE                 Location/Qualifiers
misc_feature            1..66
                        note = Synthetic sequence, 2A(nucleotide Cse2-Cas7)
source                  1..66
                        mol_type = other DNA
                        organism = synthetic construct
SEQUENCE: 60
ggctccggcg ccaccaattt ttctctgctg aagcaggcag gcgatgtgga ggagaaccca     60
ggacct                                                                66

SEQ ID NO: 61           moltype = DNA  length = 66
FEATURE                 Location/Qualifiers
misc_feature            1..66
                        note = Synthetic sequence, 2A(nucleotide Cas7-Cas5)
source                  1..66
                        mol_type = other DNA
                        organism = synthetic construct
SEQUENCE: 61
ggatctggag ccaccaattt cagcctgctg aagcaagcag gcgacgtgga agaaaaccca     60
ggacca                                                                66

SEQ ID NO: 62           moltype = DNA  length = 66
FEATURE                 Location/Qualifiers
misc_feature            1..66
                        note = Synthetic sequence, 2A(nucleotide Cas5-Cas6)
source                  1..66
                        mol_type = other DNA
                        organism = synthetic construct
SEQUENCE: 62
ggatctgggg ctactaattt ttctctgctg aagcaagccg gcgacgtgga agagaatcca     60
ggaccg                                                                66

SEQ ID NO: 63           moltype = DNA  length = 1388
FEATURE                 Location/Qualifiers
source                  1..1388
                        mol_type = unassigned DNA
                        organism = Homo sapiens
SEQUENCE: 63
tgaatgggta tgatgcttag aacagtgatt ggcatccagt atgtgccctc gaggcctctt     60
aattattact ggcttgctca tagtgcatgt tctttgtggg ctaactctag cgtcaataaa    120
aatgttaaga ctgagttgca gccgggcatg gtggctcatg cctgtaatcc cagcattcta    180
ggaggctgag gcaggaggat cgcttgagcc caggagttcg agaccagcct gggcaacata    240
gtgtgatctt gtatctataa aaataaacaa aattagcttg gtgtggtggc gcctgtagtc    300
cccagccact tggaggggtg aggtgagagg attgcttgag cccgggatgg tccaggctgc    360
agtgagccat gatcgtgcca ctgcactcca gcctgggcga cagagtgaga ccctgtctca    420
caacaacaac aacaacaaca aaaaggctga gctgcaccat gcttgaccca gtttcttaaa    480
```

```
attgttgtca aagcttcatt cactccatgg tgctatagag cacaagattt tatttggtga    540
gatggtgctt tcatgaattc ccccaacaga gccaagctct ccatctagtg gacagggaag    600
ctagcagcaa accttccctt cactacaaaa cttcattgct tggccaaaaa gagagttaat    660
tcaatgtaga catctatgta ggcaattaaa aacctattga tgtataaaac agtttgcatt    720
catggagggc aactaaatac attctaggac tttataaaag atcacttttt atttatgcac    780
agggtggaac aagatggatt atcaagtgtc aagtccaatc tatgacatca attattatac    840
atcggagccc tgccaaaaaa tcaatgtgaa gcaaatcgca gcccgcctcc tgcctccgct    900
ctactcactg tgtgttcatct ttggttttgt gggcaacatg ctggtcatcc tcatcctgat    960
aaactgcaaa aggctgaaga gcatgactga catctacctg ctcaacctgg ccatctctga   1020
cctgttttc cttcttactg tccccttctg ggctcactat gctgccgccc agtgggactt    1080
tggaaataca atgtgtcaac tcttgacagg gctctatttt ataggcttct tctctggaat   1140
cttcttcatc atcctcctga caatcgatag gtacctggct gtcgtccatg ctgtgtttgc    1200
tttaaaagcc aggacggtca cctttggggt ggtgacaagt gtgatcactt gggtggtggc   1260
tgtgtttgcg tctctcccag gaatcatctt taccagatct caaaaagaag gtcttcatta   1320
cacctgcagc tctcattttc catacagtca gtatcaattc tggaagaatt ccagacatt    1380
aaagatag                                                            1388

SEQ ID NO: 64           moltype = DNA   length = 987
FEATURE                 Location/Qualifiers
misc_feature            1..987
                        note = Synthetic sequence, CCR5 Gene with CRISPR induced
                         deletion.
misc_feature            76..476
                        note = Deleted nucleotides
source                  1..987
                        mol_type = other DNA
                        organism = synthetic construct
SEQUENCE: 64
ccacttggag gggtgaggtg agaggattgc ttgagcccgg gatggtccag gctgcagtga     60
gccatgatcg tgccactgca ctccagcctg ggcgacagag tgagaccctg tctcacaaca    120
acaacaacaa caacaaaaag gctgagctgc accatgcttg acccagtttc ttaaaattgt    180
tgtcaaagct tcattcactc catggtgcta tagagcacaa gattttattt ggtgagatgg    240
tgctttcatg aattcccca acagagccaa gctctccatc tagtggacag ggaagctagc    300
agcaaacctt cccttcacta caaaacttca ttgcttggcc aaaaagagag ttaattcaat    360
gtagacatct atgtaggcaa ttaaaaacct attgatgtat aaaacagttt gcattcatgg    420
agggcaacta aatacattct aggactttat aaaagatcac ttttatttta tgcacagggt    480
ggaacaagat ggattatcaa gtgtcaagtc caatctatga catcaattat tatacatcgg    540
agccctgcca aaaaatcaat gtgaagcaaa tcgcagcccg cctcctgcct ccgctctact    600
cactggtgtt catctttggt tttgtgggca acatgctggt catcctcatc ctgataaact    660
gcaaaaggct gaagagcatg actgacatct acctgctcaa cctggccatc tctgacctgt    720
ttttccttct tactgtcccc ttctgggctc actatgctgc cgcccagtgg gactttggaa    780
atacaatgtg tcaactcttg acagggtctct attttatagg cttcttctct ggaatcttct    840
tcatcatcct cctgacaatc gataggtacc tggctgtcgt ccatgctgtg tttgctttaa    900
aagccaggac ggtcaccttt ggggtggtga caagtgtgat cacttgggtg gtggctgtgt    960
ttgcgtctct cccaggaatc atcttta                                        987

SEQ ID NO: 65           moltype = DNA   length = 987
FEATURE                 Location/Qualifiers
misc_feature            1..987
                        note = Synthetic sequence, CCR5 Gene with CRISPR induced
                         deletion.
misc_feature            120..460
                        note = Deleted nucleotides
source                  1..987
                        mol_type = other DNA
                        organism = synthetic construct
SEQUENCE: 65
ccacttggag gggtgaggtg agaggattgc ttgagcccgg gatggtccag gctgcagtga     60
gccatgatcg tgccactgca ctccagcctg ggcgacagag tgagaccctg tctcacaaca    120
acaacaacaa caacaaaaag gctgagctgc accatgcttg acccagtttc ttaaaattgt    180
tgtcaaagct tcattcactc catggtgcta tagagcacaa gattttattt ggtgagatgg    240
tgctttcatg aattcccca acagagccaa gctctccatc tagtggacag ggaagctagc    300
agcaaacctt cccttcacta caaaacttca ttgcttggcc aaaaagagag ttaattcaat    360
gtagacatct atgtaggcaa ttaaaaacct attgatgtat aaaacagttt gcattcatgg    420
agggcaacta aatacattct aggactttat aaaagatcac ttttatttta tgcacagggt    480
ggaacaagat ggattatcaa gtgtcaagtc caatctatga catcaattat tatacatcgg    540
agccctgcca aaaaatcaat gtgaagcaaa tcgcagcccg cctcctgcct ccgctctact    600
cactggtgtt catctttggt tttgtgggca acatgctggt catcctcatc ctgataaact    660
gcaaaaggct gaagagcatg actgacatct acctgctcaa cctggccatc tctgacctgt    720
ttttccttct tactgtcccc ttctgggctc actatgctgc cgcccagtgg gactttggaa    780
atacaatgtg tcaactcttg acagggtctct attttatagg cttcttctct ggaatcttct    840
tcatcatcct cctgacaatc gataggtacc tggctgtcgt ccatgctgtg tttgctttaa    900
aagccaggac ggtcaccttt ggggtggtga caagtgtgat cacttgggtg gtggctgtgt    960
ttgcgtctct cccaggaatc atcttta                                        987

SEQ ID NO: 66           moltype = DNA   length = 988
FEATURE                 Location/Qualifiers
misc_feature            1..988
                        note = Synthetic sequence, CCR5 Gene with CRISPR induced
```

|  |  | deletion. |
|---|---|---|
| misc_feature |  | 115..382 |
|  |  | note = Deleted nucleotides |
| source |  | 1..988 |
|  |  | mol_type = other DNA |
|  |  | organism = synthetic construct |

SEQUENCE: 66

```
ccacttggag gggtgaggtg agaggattgc ttgagcccgg gatggtccag gctgcagtga   60
gccatgatcg tgccactgca ctccagcctg ggcgacagag tgagaccctg tctcacaaca  120
acaacaacaa caacaaaaag gctgagctgc accatgcttg acccagtttc ttaaaattgt  180
tgtcaaagct tcattcactc catggtgcta tagagcacaa gattttattt ggtgagatgg  240
tgctttcatg aattccccca acagagccaa gctctccatc tagtggacag ggaagctagc  300
agcaaacctt cccttcacta caaaacttca ttgcttggcc aaaaagagag ttaattcaat  360
gtagacatct atgtaggcaa ttaaaaacct attgatgtat aaaacagttt gcattcatgg  420
agggcaacta aatacattct aggactttat aaaagatcac ttttttattta tgcacagggt  480
ggaacaagat ggattatcaa gtgtcaagtc caatctatga catcaattat tatacatcgg  540
agccctgcta aaaaatcaa tgtgaagcaa atcgcagccc gctcctgcc tccgctctac  600
tcactggtgt tcatctttgg ttttgtgggc aacatgctgc tcatcctcat ctgataaac  660
tgcaaaaggc tgaagagcat gactgacatc tacctgctca acctggccat ctctgacctg  720
tttttccttc ttactgtccc cttctgggct cactatgctg ccgcccagtg ggactttgga  780
aatacaatgt gtcaactctt gacagggctc tattttatag gcttcttctc tggaatcttc  840
ttcatcatcc tcctgacaat cgataggtac ctggctgtcg tccatgctgt gtttgcttta  900
aaagccagga cggtcacctt tgggtggtg acaagtgtga tcacttgggt ggtggctgtg  960
tttgcgtctc tcccaggaat catcttta                                    988
```

| SEQ ID NO: 67 |  | moltype = DNA length = 987 |
|---|---|---|
| FEATURE |  | Location/Qualifiers |
| misc_feature |  | 1..987 |
|  |  | note = Synthetic sequence, CCR5 Gene with CRISPR induced |
|  |  | deletion. |
| misc_feature |  | 61..404 |
|  |  | note = Deleted nucleotides |
| source |  | 1..987 |
|  |  | mol_type = other DNA |
|  |  | organism = synthetic construct |

SEQUENCE: 67

```
ccacttggag gggtgaggtg agaggattgc ttgagcccgg gatggtccag gctgcagtga   60
gccatgatcg tgccactgca ctccagcctg ggcgacagag tgagaccctg tctcacaaca  120
acaacaacaa caacaaaaag gctgagctgc accatgcttg acccagtttc ttaaaattgt  180
tgtcaaagct tcattcactc catggtgcta tagagcacaa gattttattt ggtgagatgg  240
tgctttcatg aattccccca acagagccaa gctctccatc tagtggacag ggaagctagc  300
agcaaacctt cccttcacta caaaacttca ttgcttggcc aaaaagagag ttaattcaat  360
gtagacatct atgtaggcaa ttaaaaacct attgatgtat aaaacagttt gcattcatgg  420
agggcaacta aatacattct aggactttat aaaagatcac ttttttattta tgcacagggt  480
ggaacaagat ggattatcaa gtgtcaagtc caatctatga catcaattat tatacatcgg  540
agccctgcca aaaatcaat gtgaagcaaa tcgcagcccg cctcctgcct ccgctctact  600
cactgtgtt catctttggt tttgtgggca acatgctgct catcctcatc ctgataaact  660
gcaaaaggct gaagagcatg actgacatct acctgctcaa cctggccatc tctgacctgt  720
ttttccttct tactgtcccc ttctgggctc actatgctgc cgcccagtgg gactttggaa  780
atacaatgtg tcaactcttg acagggctct attttatagg cttcttctct ggaatcttct  840
tcatcatcct cctgacaatc gataggtacc tggctgtcgt ccatgctgtg tttgctttaa  900
aagccaggac ggtcaccttt ggggtggtga caagtgtgat cacttgggtg gtggctgtgt  960
ttgcgtctct cccaggaatc atcttta                                    987
```

| SEQ ID NO: 68 |  | moltype = DNA length = 2130 |
|---|---|---|
| FEATURE |  | Location/Qualifiers |
| source |  | 1..2130 |
|  |  | mol_type = unassigned DNA |
|  |  | organism = Homo sapiens |

SEQUENCE: 68

```
agggaaaaga ggcttcctgg aggagatggc ttagaaccat agacctgccc tctgcctcat   60
gcctcctcca tcatggagga tggttgtcca gtttctgttt gaaccccacc ccataccttg  120
ccagggctct cactgccaga cacagaatag ggggctccct gggttcaaag tagagctcac  180
ttctgtcccc tgggcttctc ctgactgttc cttgtgtgac ctgtcccac atctgatgg  240
gctgcaggag ccagtgctgt ggggacagaa ggtctggagc tgcccgtgaa gggcagaatg  300
ctgccctcag acccgcttcc tccctgtcct tgtctgtcca aggagaatga ggtctcactg  360
gtggatttcg gactaccctg aggagctggc acctgaggga caaggccccc cacctgccca  420
gctccagcct ctgatgaggg gtgggagaga gctacatgag gttgctaaga aagcctcccc  480
tgaaggagac cacacagtgt gtgaggttgg agtctctagc agcgggttct gtgccccag  540
ggatagtctg gctgtccagg cactgctctt gatataaaca ccacctccta gttatgaaac  600
catgcccatt ctgcctctct gtatggaaaa gagcatgggg ctggcccgtg gggtggtgtc  660
cactttaggc cctgtgggag atcatgggaa cccacgcagt gggtcatagg ctctctcatt  720
tactactcac atccactctg tgaagaagcg attatgatct ctcctctaga aactcgtaga  780
gtcccatgtc tgccggcttc cagagcctgc actcctccac ctgcttgag ccttctgctg  840
gctagaggag ctaggatgca cagcagctct gtgacccttt gtttgagagg aacaggaaaa  900
ccaccccttct ctctggccca ctgtgtcctc ttcctgccct gccatcccct tctgtgaatg  960
ttagacccat gggagcagct ggtcagaggg gaccccggcc tggggcccct aaccctatgt 1020
agcctcagtc ttcccatcag gctctcagct cagcctgagt gttgaggccc cagtggctgc 1080
tctgggggcc tcctgagttt ctcatctgtg cccctccctc cctggcccag gtgaaggtgt 1140
```

```
ggttccagaa ccggaggaca aagtacaaac ggcagaagct ggaggaggaa gggcctgagt 1200
ccgagcagaa gaagaagggc tcccatcaca tcaaccggtg cgcattgcc acgaagcagg 1260
ccaatgggga ggacatcgat gtcacctcca atgactaggg tgggcaacca caaacccacg 1320
agggcagagt gctgcttgct gctggccagg cccctgcgtg ggcccaagct ggactctggc 1380
cactccctgg ccaggctttg gggaggcctg gagtcatggc cccacagggg ttgaagcccg 1440
gggccgccat tgacagaggg acaagcaatg ggctggctga ggcctgggac acttggcct 1500
tctcctcgga gagcctgcct gcctgggcgg gcccgcccgc caccgcagcc tcccagctgc 1560
tctccgtgtc tccaatctcc cttttgtttt gatgcatttc tgttttaatt tattttccag 1620
gcaccactgt agtttagtga tccccagtgt ccccctccc tatgggaata taaaagtctc 1680
tctcttaat gacacgggca tccagctcca gccccagagc ctgggtggt agattccggc 1740
tctgagggcc agtgggggct ggtagagcaa acgcgttcag ggcctgggag cctggggtgg 1800
ggtactggtg gaggggtca agggtaattc attaactcct ctcttttgtt ggggaccct 1860
ggtctctacc tccagctcca cagcaggaga aacaggctag catagggaa gggccatcct 1920
gtatcttgag ggaggacagg cccaggtctt tcttaacgta ttgagaggtg ggaatcaggc 1980
ccaggtagtt caatgggaga gggagagtgc ttccctctgc ctagagactc tggtggcttc 2040
tccagttgag gagaaaccag aggaaagggg aggattgggg tctggggag ggaacaccat 2100
tcacaaaggc tgacggttcc agtccgaagt                                  2130

SEQ ID NO: 69          moltype = DNA   length = 1730
FEATURE                Location/Qualifiers
misc_feature           1..1730
                       note = Synthetic sequence, EMX1 Gene with CRISPR induced
                        deletion.
misc_feature           163..675
                       note = Deleted nucleotides
misc_feature           1030..1392
                       note = Deleted nucleotides
source                 1..1730
                       mol_type = other DNA
                       organism = synthetic construct
SEQUENCE: 69
gggcttctcc tgactgttcc ttgtgtgacc tgttcccaca tctggatggg ctgcaggagc 60
cagtgctgtg gggacagaag gtctggagct gcccgtgaag ggcagaatgc tgccctcaga 120
cccgcttcct ccctgtcctt gtctgtccaa ggagaatgag gtctcactgg tggatttcgg 180
actaccctga ggagctggca cctgagggac aaggccccc acctgcccag ctccagcctc 240
tgatgagggg tgggagagag ctacatgagg ttgctaagaa agcctcccct gaaggagacc 300
acacagtgtg tgaggttgga gtctctagca gcgggtctg tgcccccagg gatagtctgg 360
ctgtccaggc actgctcttg atataaacac cacctcctag ttatgaaacc atgcccattc 420
tgcctctctg tatggaaaag agcatggggc tggcccgtgg ggtggtgtcc actttaggcc 480
ctgtgggaga tcatgggaac ccacgcagtg ggtcataggc tctctcattt actactcaca 540
tccactctgt gaagaagcga ttatgatctc tcctctagaa actcgtagag tcccatgtct 600
gccggcttcc agagcctgca ctcctccacc ttggcttggc tttgctgggg ctagaggagc 660
taggatgcac agcagctctg tgacccttg tttgagagga acaggaaaac caccccttcc 720
tctggcccac tgtgtcctct tcctgccctg ccatcccctt ctgtgaatgt tagacccatg 780
ggagcagctg gtcagagggg accccggcct ggggccccta accctatgta gcctcagtct 840
tcccatcagg ctctcagctc agcctgagtg ttgaggcccc agtggctgct ctgggggcct 900
cctgagtttc tcatctgtgc ccctccctcc ctggcccagg tgaaggtgtg gttccagaac 960
cggaggacaa agtacaaacg gcagaagctg gaggaggaag ggcctgagtc cgagcagaag 1020
aagaagggct cccatcacat caaccggtgg cgcattgcca cgaagcaggc caatggggag 1080
gacatcgatg tcacctccaa tgactagggt gggcaaccac aaacccacga gggcagagtg 1140
ctgcttgctg ctggccaggc ccctgcgtgg gcccaagctg gactctggcc actccctggc 1200
caggctttgg ggaggcctgg agtcatggcc ccacagggct gaagcccggg gccgccatt 1260
gacagaggga caagcaatgg gctggctgag gcctgggacc acttggcctt ctcctcggag 1320
agcctgcctg cctgggcggg cccgcccgcc accgcagcct cccagctgct ctccgtgtct 1380
ccaatctccc ttttgttttg atgcatttct gttttaattt attttccagg caccactgta 1440
gtttagtgat ccccagtgtc cccttccct atgggaataa taaaagtctc tctcttaatg 1500
acacgggcat ccagctccag ccccagagcc tgggtggta gattccggct ctgagggcca 1560
gtgggggctg gtagagcaaa cgcgttcagg gcctgggagc tggggtggg gtactggtgg 1620
aggggtcaa gggtaattca ttaactcctc tcttttgttg gggaccctg gtctctacct 1680
ccagctccac agcaggagaa acaggctaga catagggaag ggccatcctg            1730

SEQ ID NO: 70          moltype = DNA   length = 1730
FEATURE                Location/Qualifiers
misc_feature           1..1730
                       note = Synthetic sequence, EMX1 Gene with CRISPR induced
                        deletion.
misc_feature           296..989
                       note = Deleted nucleotides
source                 1..1730
                       mol_type = other DNA
                       organism = synthetic construct
SEQUENCE: 70
gggcttctcc tgactgttcc ttgtgtgacc tgttcccaca tctggatggg ctgcaggagc 60
cagtgctgtg gggacagaag gtctggagct gcccgtgaag ggcagaatgc tgccctcaga 120
cccgcttcct ccctgtcctt gtctgtccaa ggagaatgag gtctcactgg tggatttcgg 180
actaccctga ggagctggca cctgagggac aaggccccc acctgcccag ctccagcctc 240
tgatgagggg tgggagagag ctacatgagg ttgctaagaa agcctcccct gaaggagacc 300
acacagtgtg tgaggttgga gtctctagca gcgggtctg tgcccccagg gatagtctgg 360
ctgtccaggc actgctcttg atataaacac cacctcctag ttatgaaacc atgcccattc 420
```

```
tgcctctctg tatggaaaag agcatggggc tggcccgtgg ggtggtgtcc actttaggcc    480
ctgtgggaga tcatgggaac ccacgcagtg ggtcataggc tctctcattt actactcaca    540
tccactctgt gaagaagcga ttatgatctc tcctctagaa actcgtagag tcccatgtct    600
gccggcttcc agagcctgca ctcctccacc ttggcttggc tttgctgggg ctagaggagc    660
taggatgcac agcagctctg tgacccttg  tttgagagga acaggaaaac cacccttctc    720
tctggcccac tgtgtcctct tcctgccctg ccatcccctt ctgtgaatgt tagacccatg    780
ggagcagctg gtcagagggg accccggcct ggggccccta accctatgta gcctcagtct    840
tcccatcagg ctctcagctc agcctgagtg ttgaggcccc agtggctgct ctgggggcct    900
cctgagtttc tcatctgtgc ccctccctcc ctggcccagg tgaaggtgtg gttccagaac    960
cggaggacaa agtacaaacg gcagaagctg gaggaggaag ggcctgagtc cgagcagaag   1020
aagaagggct cccatcacat caaccggtgg cgcattgcca cgaagcaggc caatggggag   1080
gacatcgatg tcacctccaa tgactagggt gggcaaccac aaacccacga gggcagagtg   1140
ctgcttgctg ctggccaggc cctgcgtgg  gcccaagctg gactctggcc actccctggc   1200
caggctttgg ggaggcctgg agtcatggcc ccacagggct tgaagcccgg ggccgccatt   1260
gacagaggga caagcaatgg gctggctgag gcctgggacc acttggcctt ctcctcggag   1320
agcctgcctg cctgggcggg cccgcccgcc accgcagcct cccagctgct ctccgtgtct   1380
ccaatctccc ttttgttttg atgcatttct gttttaattt attttccagg caccactgta   1440
gtttagtgat cccccagtgtc cccctccct  atgggaataa taaaagtctc tctcttaatg   1500
acacgggcat ccagctccag ccccagagcc tggggtggta gattccggct ctgagggcca   1560
gtgggggctg gtagagcaaa cgcgttcagg gcctgggagc ctgggtggg  gtactggtgg   1620
aggggggtcaa gggtaattca ttaactcctc tcttttgttg ggggaccctg gtctctacct   1680
ccagctccac agcaggagaa acaggctaga cataggaagg ggccatcctg              1730

SEQ ID NO: 71           moltype = DNA   length = 176
FEATURE                 Location/Qualifiers
misc_feature            1..176
                        note = Synthetic sequence, pre-crRNA(LRSR)
source                  1..176
                        mol_type = other DNA
                        organism = synthetic construct
SEQUENCE: 71
tggatgtgtt gtttgtgtga tactataaag ttggtagatt gtgactggct taaaaaatca     60
ttaattaata ataggttatg tttagagtgt tccccgcgcc agcggggata aaccgcaggc    120
caatggggag gacatcgatg tcacctcgtg ttccccgcgc cagcggggat aaaccg        176

SEQ ID NO: 72           moltype = DNA   length = 90
FEATURE                 Location/Qualifiers
misc_feature            1..90
                        note = Synthetic sequence, pre-crRNA(RSR)
source                  1..90
                        mol_type = other DNA
                        organism = synthetic construct
SEQUENCE: 72
gtgttccccg cgccagcggg gataaaccgc aggccaatgg ggaggacatc gatgtcacct     60
cgtgttcccc gcgccagcgg ggataaaccg                                      90

SEQ ID NO: 73           moltype = DNA   length = 61
FEATURE                 Location/Qualifiers
misc_feature            1..61
                        note = Synthetic sequence, mature crRNA
source                  1..61
                        mol_type = other DNA
                        organism = synthetic construct
SEQUENCE: 73
ataaaccgca ggccaatggg gaggacatcg atgtcacctc gtgttccccg cgccagcggg     60
g                                                                     61

SEQ ID NO: 74           moltype = DNA   length = 35
FEATURE                 Location/Qualifiers
source                  1..35
                        mol_type = unassigned DNA
                        organism = Homo sapiens
SEQUENCE: 74
aagcaggcca atggggagga catcgatgtc acctc                                35

SEQ ID NO: 75           moltype = DNA   length = 34
FEATURE                 Location/Qualifiers
misc_feature            1..8
                        note = Seed sequence
misc_feature            9..32
                        note = Spacer sequence
source                  1..34
                        mol_type = unassigned DNA
                        organism = Homo sapiens
SEQUENCE: 75
tcacatcaac cggtggcgca ttgccacgaa gcag                                 34

SEQ ID NO: 76           moltype = DNA   length = 10
FEATURE                 Location/Qualifiers
```

```
misc_feature           1..10
                       note = Synthetic sequence, Emx1 deletion mutant
source                 1..10
                       mol_type = other DNA
                       organism = synthetic construct
SEQUENCE: 76
ctgccctacc                                                                    10

SEQ ID NO: 77          moltype = DNA  length = 10
FEATURE                Location/Qualifiers
misc_feature           1..10
                       note = Synthetic sequence, Emx1 deletion mutant
source                 1..10
                       mol_type = other DNA
                       organism = synthetic construct
SEQUENCE: 77
gcccacctgg                                                                    10

SEQ ID NO: 78          moltype = DNA  length = 10
FEATURE                Location/Qualifiers
misc_feature           1..10
                       note = Synthetic sequence, Emx1 deletion mutant
source                 1..10
                       mol_type = other DNA
                       organism = synthetic construct
SEQUENCE: 78
gagctgagga                                                                    10

SEQ ID NO: 79          moltype = DNA  length = 10
FEATURE                Location/Qualifiers
misc_feature           1..10
                       note = Synthetic sequence, Emx1 deletion mutant
source                 1..10
                       mol_type = other DNA
                       organism = synthetic construct
SEQUENCE: 79
accctcagct                                                                    10

SEQ ID NO: 80          moltype = DNA  length = 10
FEATURE                Location/Qualifiers
misc_feature           1..10
                       note = Synthetic sequence, Emx1 deletion mutant
source                 1..10
                       mol_type = other DNA
                       organism = synthetic construct
SEQUENCE: 80
tgaggtctca                                                                    10

SEQ ID NO: 81          moltype = DNA  length = 10
FEATURE                Location/Qualifiers
misc_feature           1..10
                       note = Synthetic sequence, Emx1 deletion mutant
source                 1..10
                       mol_type = other DNA
                       organism = synthetic construct
SEQUENCE: 81
ggactaggcc                                                                    10

SEQ ID NO: 82          moltype = DNA  length = 10
FEATURE                Location/Qualifiers
misc_feature           1..10
                       note = Synthetic sequence, Emx1 deletion mutant
source                 1..10
                       mol_type = other DNA
                       organism = synthetic construct
SEQUENCE: 82
ggactaagaa                                                                    10

SEQ ID NO: 83          moltype = DNA  length = 17
FEATURE                Location/Qualifiers
misc_feature           1..17
                       note = Synthetic sequence, Emx1 deletion mutant
source                 1..17
                       mol_type = other DNA
                       organism = synthetic construct
SEQUENCE: 83
tgatgcaggc caatggg                                                            17
```

METHOD FOR PRODUCING DNA-EDITED EUKARYOTIC CELL, AND KIT USED IN THE SAME

CROSS REFERENCE TO RELATED APPLICATIONS

This application is a Continuation of U.S. application Ser. No. 16/611,308 filed on Nov. 6, 2019 (allowed), which is a National Stage of International Application No. PCT/JP2018/022066 filed on Jun. 8, 2018, claiming priority based on Japanese Patent Application No. 2017-113747 filed on Jun. 8, 2017.

INCORPORATION BY REFERENCE OF SEQUENCE LISTING

The content of the electronically submitted sequence listing, file name: Q291086SEQ_LIST_ST26_AS FILED.xml; size: 193,047 bytes; and date of creation: Sep. 14, 2023, is incorporated herein by reference in its entirety.

TECHNICAL FIELD

The present invention relates to a method for producing DNA-edited eukaryotic cells, animals, and plants, and to a kit used in the method.

BACKGROUND ART

Bacteria and archaea have adaptive immune mechanisms which specifically recognize and eliminate organisms such as foreign phages that intend to intrude from the outside. These systems, called the CRISPR-Cas systems, first introduce genomic information on the foreign organisms into the self genome (adaptation).

Then, when the same foreign organisms intend to intrude again, the systems cleave and eliminate the foreign genomes by using the complementarity of the information introduced in the self genome and the genome sequence (interference).

Recently, genome editing (DNA editing) techniques using the above CRISPR-Cas systems as "DNA editing tools" have been developed (NPL 1).

The CRISPR-Cas systems are roughly divided into "Class 1" and "Class 2," in which effectors working in the process of cleaving DNA are composed of multiple Cas and a single Cas, respectively. Among other things, as the Class 1 CRISPR-Cas systems, "type I" involving Cas3 and Cascade complexes (meaning Cascade-crRNA complexes, and the same applies below) is widely known. As the Class 2 CRISPR-Cas systems, "type II" involving Cas9 is widely known (hereinafter, regarding the CRISPR-Cas systems, "Class 1 type I" and "Class 2 type II" may be simply referred to as "type I" and "type II," respectively). In addition, what have been widely used in the conventional DNA editing techniques are the Class 2 CRISPR-Cas systems involving Cas9 (which hereinafter may be referred to as the "CRISPR-Cas9 systems"). For example, NPL 1 reports a Class 2 CRISPR-Cas system which cleaves DNA using Cas9.

On the other hand, for the Class 1 CRISPR-Cas systems, which cleave DNA using Cas3 and Cascade complexes (which hereinafter may also be referred to as the "CRISPR-Cas3 systems"), no successful example of genomic editing has been reported in eukaryotic cells despite a lot of effort. For example, NPL 2 and NPL 3 reported that simple use of a CRISPR-Cas3 system made it possible to completely degrade target DNA in a cell-free system and selectively remove specific E. coli strains. However, these do not mean the success of genome editing, nor have they been demonstrated at all in eukaryotic cells. In addition, PTL 1 proposes to perform genome editing using the FokI nuclease in place of Cas3 in eukaryotic cells (Example 7, FIG. 7, and FIG. 11) because the CRISPR-Cas3 systems degrade target DNA in E. coli by helicase activity and exonuclease activity of Cas3 (Example 5 and FIG. 6). Moreover, PTL 2 proposes deletion of cas3 and repurposing for programmable gene repression by use of inactivated Cas3 (Cas3' and Cas3") (for example, Example 15 and claim 4(e)) because the CRISPR-Cas3 systems degrade target DNA in E. coli (FIGS. 4A-4D).

CITATION LIST

Patent Literature

[PTL 1] Published Japanese Translation of PCT International Application No. 2015-503535
[PTL 2] Published Japanese Translation of PCT International Application No. 2017-512481

Non Patent Literature

[NPL 1] Jinek M et al. (2012) A Programmable Dual-RNA Guided DNA Endonuclease in Adaptive Bacterial Immunity, Science, Vol. 337 (Issue 6096), pp. 816-821
[NPL 2] Mulepati S & Bailey S (2013) In Vitro Reconstitution of an *Escherichia coli* RNA-guided Immune System Reveals Unidirectional, ATP-dependent Degradation of DNA Target, Journal of Biological Chemistry, Vol. 288 (No. 31), pp. 22184-22192
[NPL 3] Ahmed A. Gomaa et al. (2014) Programmable Reomoval of Bacterial Strains by Use of Genome Targeting CRISPR-Cas Systems, mbio.asm.org, Volume 5, Issue 1, e00928-13

SUMMARY OF INVENTION

Technical Problem

The present invention has been made in view of the above circumstances, and an object thereof is to establish a CRISPR-Cas3 system in eukaryotic cells.

Solution to Problem

The present inventors have made earnest studies to achieve the above object, and finally succeeded in establishing a CRISPR-Cas3 system in eukaryotic cells. The most widely used CRISPR-Cas9 system has succeeded in genome editing in various eukaryotic cells, but this system usually uses a mature crRNA as a crRNA. However, it was surprising that, in the CRISPR-Cas3 systems, genome editing was difficult in eukaryotic cells in the case of using a mature crRNA and that efficient genomic editing was possible only by using a pre-crRNA, which usually was not used as a constituent element of a system. That is, in order to make the CRISPR-Cas3 systems function in eukaryotic cells, cleaving of a crRNA by proteins constituting the Cascade was found to be important. The CRISPR-Cas3 systems using this pre-crRNA were widely applicable not only to the type I-E system but also to the type I-F and type I-G systems. Moreover, addition of a nuclear localization signal, particularly a bipartite nuclear localization signal to Cas3 made it possible to further improve the genome editing efficiency for the CRISPR-Cas3 systems in eukaryotic cells. Furthermore, the present inventors have found that the CRISPR-Cas3 systems, unlike the CRISPR-Cas9 systems can cause a large deletion in a region containing a PAM sequence or in an upstream region thereof. These findings have led to the completion of the present invention.

Specifically, the present invention relates to a CRISPR-Cas3 system in eukaryotic cells, and more specifically to the following invention.

[1] A method for producing a DNA-edited eukaryotic cell, comprising: introducing a CRISPR-Cas3 system into a eukaryotic cell, wherein the CRISPR-Cas3 system includes the following (A) to (C).
  (A) a Cas3 protein, a polynucleotide encoding the protein, or an expression vector containing the polynucleotide,
  (B) a Cascade protein, a polynucleotide encoding the protein, or an expression vector containing the polynucleotide, and
  (C) a crRNA, a polynucleotide encoding the crRNA, or an expression vector containing the polynucleotide.

[2] A method for producing a DNA-edited animal (excluding a human) or plant, comprising: introducing a CRISPR-Cas3 system into an animal (excluding a human) or plant, wherein the CRISPR-Cas3 system includes the following (A) to (C).
  (A) a Cas3 protein, a polynucleotide encoding the protein, or an expression vector containing the polynucleotide,
  (B) a Cascade protein, a polynucleotide encoding the protein, or an expression vector containing the polynucleotide, and
  (C) a crRNA, a polynucleotide encoding the crRNA, or an expression vector containing the polynucleotide.

[3] The method according to [1] or [2], further comprising cleaving the crRNA with a protein constituting the Cascade protein after introducing the CRISPR-Cas3 system into the eukaryotic cell.

[4] The method according to [1] or [2], wherein the crRNA is a pre-crRNA.

[5] The method according to any one of [1] to [4], wherein a nuclear localization signal is added to the Cas3 protein and/or the Cascade protein.

[6] The method according to [5], wherein the nuclear localization signal is a bipartite nuclear localization signal.

[7] A kit for use in the method according to any one of [1] to [6], the kit comprising the following (A) and (B).
  (A) a Cas3 protein, a polynucleotide encoding the protein, or an expression vector containing the polynucleotide and
  (B) a Cascade protein, a polynucleotide encoding the protein, or an expression vector containing the polynucleotide.

[8] The kit according to [7], further comprising a crRNA, a polynucleotide encoding the crRNA, or an expression vector containing the polynucleotide.

[9] The kit according to [8], wherein the crRNA is a pre-crRNA.

[10] The kit according to any one of [7] to [9], wherein a nuclear localization signal is added to the Cas3 protein and/or the Cascade protein.

[11] The kit according to [10], wherein the nuclear localization signal is a bipartite nuclear localization signal.

Note that in the present specification, the term "polynucleotide" intends a polymer of nucleotides and is used synonymously with the term "gene," "nucleic acid," or "nucleic acid molecule." The polynucleotide may also be present in the form of DNA (for example, cDNA or genomic DNA) or in the form of RNA (for example, mRNA). Also, the term "protein" is used synonymously with "peptide" or "polypeptide."

Advantageous Effects of Invention

Use of the CRISPR-Cas3 system of the present invention made it possible to edit DNA in eukaryotic cells.

BRIEF DESCRIPTION OF DRAWINGS

FIG. 3A is a diagram showing the CCR5 gene (clone 1, SEQ ID NO: 64) in which a part of the nucleic acid sequence has been deleted by the CRISPR-Cas3 system.

FIG. 3B is a diagram showing the CCR5 gene (clone 2, SEQ ID NO: 65) in which a part of the nucleic acid sequence has been deleted by the CRISPR-Cas3 system.

FIG. 3C is a diagram showing the CCR5 gene (clone 3, SEQ ID NO: 66) in which a part of the nucleic acid sequence has been deleted by the CRISPR-Cas3 system.

FIG. 3D is a diagram showing the CCR5 gene (clone 4, SEQ ID NO: 67) in which a part of the nucleic acid sequence has been deleted by the CRISPR-Cas3 system.

FIGS. 5A-5B schematic diagrams showing the position of the target sequence in the EMX1 gene (SEQ ID NO: 68).

FIG. 6A is a diagram showing the EMX1 gene (clone 1, SEQ ID NO: 69) deleted in part of the nucleic acid sequence by the CRISPR-Cas3 system.

FIG. 6B is a diagram showing the EMX1 gene (clone 2, SEQ ID NO: 70) deleted in part of the nucleic acid sequence by the CRISPR-Cas3 system.

FIG. 10A is a diagram showing the structures of the pre-crRNAs (LRSR and RSR, SEQ ID NOs: 71 and 72 respectively) and the mature crRNA (SEQ ID NO: 73) used in Examples. In the figure, the underlines show 5' handle (Cas5 handle), and the double underlines shows the 3' handle (Cas6 handle).

FIG. 16 is a diagram showing the magnitude of deletion by the CRISPR-Cas3 system detected by the sequencing of a TA cloning sample of a PCR product.

DESCRIPTION OF EMBODIMENTS

[1] Method for Producing DNA-Edited Eukaryotic Cells, Animals, and Plants

A method of the present invention comprises introducing a CRISPR-Cas3 system into a eukaryotic cell, wherein the CRISPR-Cas3 system includes the following (A) to (C).

(A) a Cas3 protein, a polynucleotide encoding the protein, or an expression vector containing the polynucleotide,
(B) a Cascade protein, a polynucleotide encoding the protein, or an expression vector containing the polynucleotide, and
(C) a crRNA, a polynucleotide encoding the crRNA, or an expression vector containing the polynucleotide The Class 1 CRISPR-Cas systems are classified into type I and type III, and depending on the types of proteins constituting the Cascade (hereinafter simply referred to as the "Cascade" or the "Cascade proteins"), type I is further classified into six types of type I-A, type I-B, type I-C, type I-D, type I-E, and type I-F as well as type I-G, a subtype of type I-B (for example, see [van der Oost J et al. (2014) Unravelling the structural and mechanistic basis of CRISPR-Cas systems, Nature Reviews Microbiologym, Vol. 12 (No. 7), pp. 479-492] and [Jackson R N et al. (2014) Fitting CRISPR-associated Cas3 into the Helicase Family Tree, Current Opinion in Structural Biology, Vol. 24, pp. 106-114]).

The type I CRISPR-Cas systems have the function of cleaving DNA by cooperation of Cas3 (protein having nuclease activity and helicase activity), Cascade, and CER-NAs. They are referred to as the "CRISPR-Cas3 system" in the present invention because Cas3 is used as a nuclease.

Use of the CRISPR-Cas3 system of the present invention makes it possible to obtain, for example, the following advantages.

Figure 12:
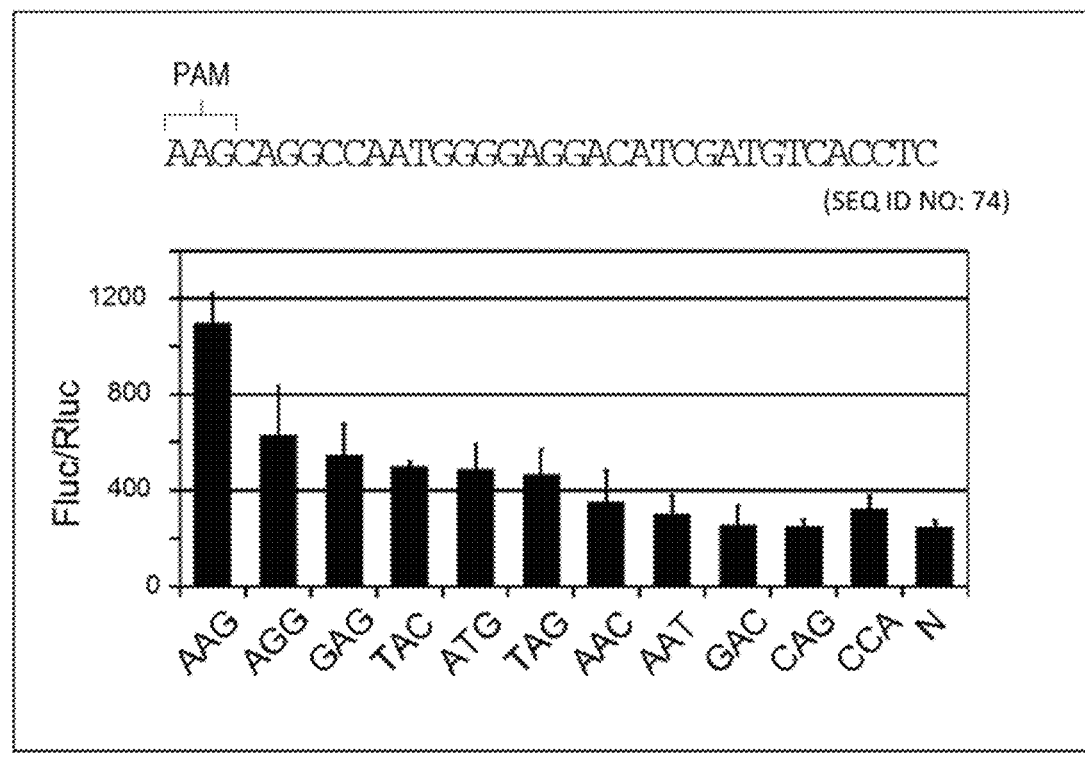
FIG. 12 is a diagram showing the effects of the PAM sequence on the DNA cleavage activity of the CRISPR-Cas3 system.

First, the crRNA used in the CRISPR-Cas3 system generally recognizes a target sequence of 32 to 37 bases (Ming Li et al., Nucleic Acids Res. 2017 May 5; 45 (8): 4642-4654). On the other hand, the crRNA used in the CRISPR-Cas9 system generally recognizes a target sequence of 18 to 24 bases. Therefore, it is considered that the CRISPR-Cas3 system can recognize target sequences more accurately than the CRISPR-Cas9 system. In addition, the PAM sequence of the Class 2 type II system, the CRISPR-Cas9 system, is "NGG (N is an arbitrary base)" adjacent to 3' side of the target sequence. Also, the PAM sequence of the Class 2 type V system, the CRISPR-Cpf1 system, is "AA" adjacent to the 5' side of the target sequence. On the other hand, the PAM sequence of the CRISPR-Cas3 system of the present invention is "AAG" adjacent to 5' side of the target sequence or a nucleic acid sequence similar to that (for example, "AGG," "GAG," "TAC," "ATG," "TAG," and the like) (FIG. 12). Thus, it is considered that, by using the CRISPR-Cas3 system of the present invention, regions which cannot be recognized by conventional methods can be subjected to DNA editing.

Furthermore, unlike the above Class 2 CRISPR-Cas systems, the CRISPR-Cas3 system causes DNA cleavages at multiple locations. Therefore, use of the CRISPR-Cas3 system of the present invention makes it possible to generate a wide range of deletion mutations ranging from one hundred to several thousand, and possibly even more bases (FIGS. 3, 6, and 16 to 18). It is considered that this function can be used for knocking out a long genomic region or knocking in long DNA. When performing knock-in, donor DNA is usually used, and the donor DNA is also a molecule constituting the CRISPR-Cas3 system of the present invention.

Note that, when simply described as "Cas3" in the present specification, it means a "Cas3 protein." The same applies to Cascade proteins.

Figure 15:
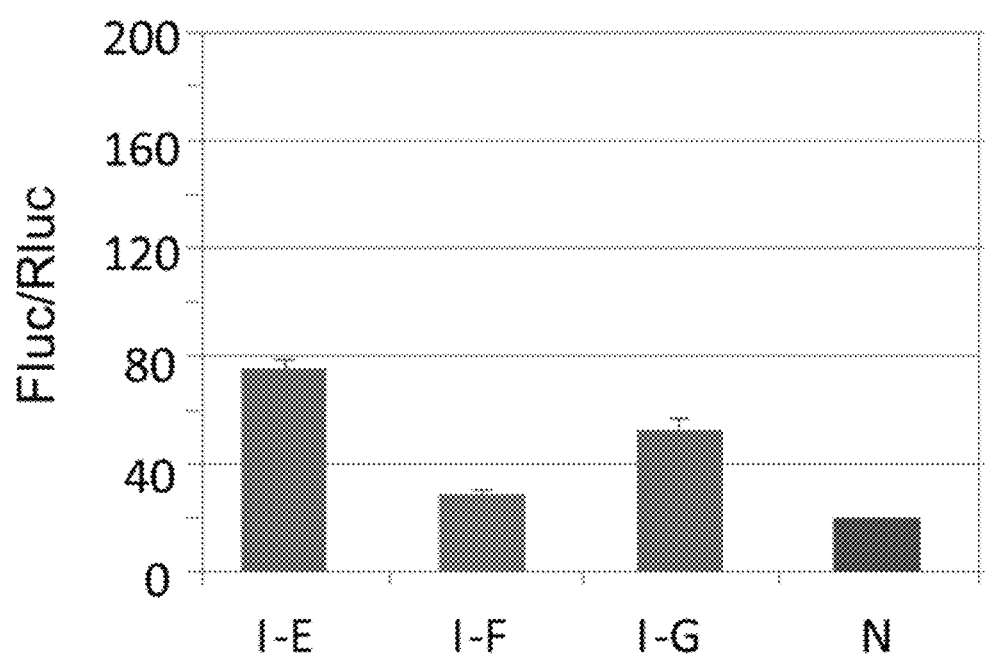
FIG. 15 shows a comparison of the DNA cleavage activity of the type I-E, type I-F, and type I-G CRISPR-Cas3 systems.

The CRISPR-Cas3 system of the present invention includes all six subtypes of type I. That is, although proteins constituting the CRISPR-Cas3 system may differ slightly in constitution and the like depending on the subtype (for example, the proteins constituting the Cascade are different), the present invention includes all of these proteins. Indeed, in the present example, it was found that genomic editing is possible not only for type I-E but also for type 1-G and type I-F systems (FIG. 15).

The type I-E CRISPR-Cas3 system, which is common among type I CRISPR-Cas3 systems, cleaves DNA when a crRNA cooperates with Cas3 and Cascade (Cse1 (Cas8), Cse2 (Cas11), Cas5, Cas6, and Cas7).

The type I-A system has Cascade constituent elements of Cas8a1, Csa5 (Cas11), Cas5, Cas6, and Cas7, the type I-B has Cascade constituent elements of Cas8b1, Cas5, Cas6, and Cas7, the type I-C has Cascade constituent elements of Cas8c, Cas5, and Cas7, the type I-D has Cascade constituent elements of Cas10d, Csc1 (Cas5), Cas6, and Csc2 (Cas7), the type I-F has Cascade constituent elements of Csy1 (Cas8f), Csy2 (Cas5), Cas6, and Csy3 (Cas7), and the type I-G system has Cascade constituent elements Cst1 (Cas8a1), Cas5, Cas6, and Cst2 (Cas7). In the present invention, Cas3 and Cascade are collectively referred to as the "Cas protein group."

Hereinafter, the type I-E CRISPR-Cas3 system is described as a representative example. For other types of CRISPR-Cas3 systems, the Cascade constituting the systems may be interpreted as appropriate.

—Cas Protein Group—

In the CRISPR-Cas3 system of the present invention, the Cas protein group can be introduced into eukaryotic cells in the form of a protein, in the form of a polynucleotide encoding the protein, or in the form of an expression vector containing the polynucleotide. When the Cas protein group is introduced into eukaryotic cells in the form of a protein, it is possible to appropriately prepare the amount and the like of each protein, which is excellent from the viewpoint of handling. Moreover, taking into consideration, for example, the efficiency of cleavage in cells, it is also possible to first form a complex of the Cas protein group and then to introduce it to eukaryotic cells.

In the present invention, it is preferable to add a nuclear localization signal to the Cas protein group. The nuclear localization signal can be added to the N-terminus side and/or the C-terminus side of the Cas protein group (5'-end side and/or 3'-end side of the polynucleotide encoding each Cas protein group). In this way, addition of a nuclear localization signal to the Cas protein group promotes localization to the nucleus in a cell, making it possible to efficiently perform DNA editing as a result.

The above nuclear localization signal is a peptide sequence composed of several to several tens of basic amino acids, and its sequence is not particularly limited as long as proteins are transferred into the nucleus. A specific example of such nuclear localization signal is described in, for example, [Wu J et al. (2009) The Intracellular Mobility of Nuclear Import Receptors and NLS Cargoes, Biophysical journal, Vol. 96 (Issue 9), pp. 3840-3849]. Any nuclear localization signal usually used in the technical field can be used in the present invention.

The nuclear localization signal may be, for example, PKKKRKV (SEQ ID NO: 52) (encoded by the nucleic acid sequence CCCAAGAAGAAGCGGAAGGTG (SEQ ID NO: 53)). When the above nuclear localization signal is used, it is preferable to arrange, for example, a polynucleotide composed of the nucleic acid sequence with SEQ ID NO: 53 on 5'-end side of the polynucleotide encoding each Cas protein group. In addition, the nuclear localization signal can be, for example, KRTADGSEFESPKKKRKVE (SEQ ID NO: 54) (encoded by the nucleic acid sequence AAGCGGACTGCTGATGGCAGTGAATTTGAGTCCC-CAAAGAAGAAGAGAAAGGTG GAA (SEQ ID NO: 55)). When the above nuclear localization signal is used, it is preferable to arrange, for example, polynucleotides composed of the nucleic acid sequences with SEQ ID NO: 55 on both sides of the polynucleotide encoding each Cas protein group (specifically, to use a "bipartite nuclear localization signal (bpNLS)").

Such modifications are important for allowing the CRISPR-Cas3 system of the present invention to be expressed and to function efficiently in eukaryotic cells, together with the utilization of pre-crRNAs described later.

One preferred embodiment of the Cas protein group used in the present invention is as follows.

Cas3; a protein encoded by a polynucleotide composed of a nucleic acid sequence represented by SEQ ID NO: 1 or SEQ ID NO: 7

Cse1 (Cas8); a protein encoded by a polynucleotide composed of a nucleic acid sequence represented by SEQ ID NO: 2 or SEQ ID NO: 8

Cse2 (Cas11); a protein encoded by a polynucleotide composed of a nucleic acid sequence represented by SEQ ID NO: 3 or SEQ ID NO: 9

Cas5; a protein encoded by a polynucleotide composed of a nucleic acid sequence represented by SEQ ID NO: 4 or SEQ ID NO: 10

Cas6; a protein encoded by a polynucleotide composed of a nucleic acid sequence represented by SEQ ID NO: 5 or SEQ ID NO: 11

Cas7; a protein encoded by a polynucleotide composed of a nucleic acid sequence represented by SEQ ID NO: 6 or SEQ ID NO: 12

The above Cas protein group is (1) a protein obtained by adding PKKKRKV (SEQ ID NO: 52) as a nuclear localization signal to the N-termini of Cas3, Cse1 (Cas8), Cse2 (Cas11), Cas5, Cas6, and Cas7 of wild type *E. coli*, or (2) a protein obtained by adding KRTADGSEFESPKKKRKVE (SEQ ID NO: 54) as a nuclear localization signal to the N-termini and C-termini of Cas3, Cse1 (Cas8), Cse2 (Cas11), Cas5, Cas6, and Cas7 of wild type *E. coli*. With proteins having such amino acid sequences, the above Cas protein group can be transferred into the nucleus of a eukaryotic cell. The above Cas protein group transferred to the nucleus in this way cleaves the target DNA. In addition, it is possible to edit target DNA even in a DNA region having a strong structure considered to be difficult in the CRISPAR-Cas9 system (heterochromatin and the like).

Another embodiment of the proteins in the Cas protein group used in the present invention is a protein encoded by a nucleic acid sequence having 90% or more sequence identity with the nucleic acid sequence of the above Cas protein group. Another embodiment of the proteins in the Cas protein group used in the present invention is a protein encoded by a polynucleotide which hybridizes with a polynucleotide composed of a nucleic acid sequence complementary to the nucleic acid sequence of the Cas protein group described above under stringent conditions. Each of the above proteins has DNA cleavage activity when forming a complex with another protein constituting the Cas protein group. The meanings of terms such as "sequence identity" and "stringent conditions" are described later.

—Polynucleotide Encoding Cas Protein Group—

Polynucleotides encoding wild type proteins constituting the type I-E CRISPR-Cas system include polynucleotides modified to be efficiently expressed in eukaryotic cells. That is, it is possible to use a polynucleotide which encodes the Cas protein group and which has been modified. One preferred embodiment of the modification of polynucleotides is modification to a nucleic acid sequence suitable for expression in eukaryotic cells, for example, optimization of a codon to be expressed in eukaryotic cells.

One preferred embodiment of polynucleotides encoding the Cas protein group used in the present invention is as follows Cas3; a polynucleotide composed of a nucleic acid sequence represented by SEQ ID NO: 1 or SEQ ID NO: 7

Cse1 (Cas8); a polynucleotide composed of a nucleic acid sequence represented by SEQ ID NO: 2 or SEQ ID NO: 8

Cse2 (Cas11); a polynucleotide composed of a nucleic acid sequence represented by SEQ ID NO: 3 or SEQ ID NO: 9

Cas5; a polynucleotide composed of a nucleic acid sequence represented by SEQ ID NO: 4 or SEQ ID NO: 10

Cas6; a polynucleotide composed of a nucleic acid sequence represented by SEQ ID NO: 5 or SEQ ID NO: 11

Cas7; a polynucleotide composed of a nucleic acid sequence represented by SEQ ID NO: 6 or SEQ ID NO: 12

Each of these is a polynucleotide made to function and be expressed in mammalian cells by artificially modifying the nucleic acid sequences encoding the wild type Cas protein group of *E. coli* (Cas3; SEQ ID NO: 13, Cse1 (Cas8); SEQ ID NO: 14, Cse2 (Cas11); SEQ ID NO: 15, Cas5; SEQ ID NO: 16, Cas6; SEQ ID NO: 17, Cas7; SEQ ID NO: 18).

The above artificial modification of polynucleotides is to modify to a nucleic acid sequence suitable for expression in eukaryotic cells and to add a nuclear localization signal. Modification of a nucleic acid sequence and addition a nuclear localization signal are as described above. As a result, it can be expected that, for the Cas protein group, the expression level will be sufficiently increased and the functions will be improved.

Another embodiment of polynucleotides encoding the Cas protein group used in the present invention is a polynucleotide formed by modifying a nucleic acid sequence encoding the wild type Cas protein group, composed of a nucleic acid sequence having 90% or more sequence identity with the nucleic acid sequence of the above Cas protein group. Proteins expressed from these polynucleotides have DNA cleavage activity when forming a complex with proteins expressed from other polynucleotides constituting the Cas protein group.

The sequence identity of nucleic acid sequences may be at least 90% or more and more preferably 95% or more (for example, 95%, 96%, 97%, 98%, and 99% or more) in the entire nucleic acid sequence (or the region encoding the site required for the functions of Cse3). It is possible to determine the identity of nucleic acid sequences using a program such as BLASTN (see [Altschul SF (1990) Basic local alignment search tool, Journal of Molecular Biology, Vol. 215 (Issue 3), pp. 403-410]). Examples of the parameters for analyzing nucleic acid sequences by BLASTN include score=100 and word length =12. Specific methods for analysis by BLASTN are known to those skilled in the art. Addition or deletion (gap and the like) may be allowed in order to align the nucleic acid sequences to be compared with the optimal state.

Moreover, "having DNA cleavage activity" is intended to mean the ability to cleave at least one site of a polynucleotide strand.

It is preferable for the CRISPR-Cas3 system of the present invention to cleave DNA by specifically recognizing the target sequence. For example, the dual-Luciferase assay described in Example A-1 makes it possible to know whether or not the CRISPR-Cas3 system specifically recognizes the target sequence.

Another embodiment of polynucleotides encoding the Cas protein group used in the present invention is a polynucleotide which hybridizes with a polynucleotide composed of a nucleic acid sequence complementary to the nucleic acid sequence of the Cas protein group described above under stringent conditions. Proteins expressed from these polynucleotides have DNA cleavage activity when forming a complex with proteins expressed from other polynucleotides constituting the Cas protein group.

Here, the "stringent conditions" refer to the conditions under which two polynucleotide strands form a double-stranded polynucleotide specific for a nucleic acid sequence but does not form a nonspecific double-stranded polynucleotide. The phrase "hybridizes under stringent conditions" can be said in other words as conditions capable of hybridizing in a temperature range from a melting temperature (Tm value) of nucleic acids with high sequence identity (for example, perfectly matched hybrids) to a temperature lower by 15° C., preferably by 10° C., and more preferably by 5° C.

Examples of the stringent conditions are shown as follows. First, two types of polynucleotides are hybridized for 16 to 24 hours at 60 to 68° C. (preferably 65° C. and more preferably 68° C.) in a buffer solution (pH 7.2) composed of 0.25 M $Na_2HPO_4$, 7% SDS, 1 mM EDTA, and 1×Denhardt's solution. Thereafter, washing is carried out twice for 15 minutes in a buffer solution (pH 7.2) composed of 20 mM $Na_2HPO_4$, 1% SDS, and 1 mM EDTA at 60 to 68° C. (preferably 65° C. and more preferably 68° C.).

Other examples include the following method. First, prehybridization is carried out overnight at 42° C. in a hybridization solution containing 25% formamide (50% formamide under more severe conditions), 4×SSC (sodium chloride/sodium citrate), 50 mM Hepes (pH 7.0), 10×Denhardt's solution, and 20 µg/ml of denatured salmon sperm DNA. Thereafter, labeled probes are added, and incubation is carried out overnight at 42° C. to hybridize the two kinds of polynucleotides.

Next, washing is carried out under any of the following conditions. Normal condition; 1×SSC and 0.1% SDS are used as washing liquids for washing at about 37° C. Severe condition; 0.5×SSC and 0.1% SDS are used as washing liquids for washing at about 42° C. More severe condition; 0.2×SSC and 0.1% SDS are used as washing liquids for washing at about 65° C.

As the washing conditions for hybridization become more severe, the specificity of hybridization becomes higher. Note that the above combination of conditions SSC, SDS, and temperature is merely illustrative. Stringency similar to the above can be achieved by appropriately combining the above-mentioned elements for determining the stringency of hybridization or other elements (for example, probe concentration, probe length, and hybridization reaction time). This is described in, for example, [Joseph Sambrook & David W. Russell, Molecular cloning: a laboratory manual 3rd Ed., New York: Cold Spring Harbor Laboratory Press, 2001].

—Expression Vector Containing Polynucleotide Encoding Cas Protein Group—

In the present invention, it is possible to use an expression vector for expressing the Cas protein group. Regarding the expression vector, various types of commonly used vectors can be used as a base vector, and it can be appropriately selected depending on the cells for introduction or the introduction method. Specific examples usable include plasmids, phages, cosmids, and the like. The specific type of the vector is not particularly limited, and it suffices to appropriately select a vector which can be expressed in the host cell.

Examples of the expression vectors described above include phage vectors, plasmid vectors, viral vectors, retroviral vectors, chromosome vectors, episomal vectors, virus-derived vectors (bacterial plasmids, bacteriophages, yeast episomes, and the like), yeast chromosomal elements and viruses (baculoviruses, papova viruses, vaccinia viruses, adenoviruses, tripox viruses, pseudorabies viruses, herpes viruses, lentiviruses, retroviruses, and the like), and vectors derived from combinations thereof (cosmids, phagemids, and the like).

Preferably, the expression vector further contains a site for transcription initiation and transcription termination as well as a ribosome binding site in the transcription region. The coding site of the mature transcript in the vector will contain the transcription initiation codon AUG at the beginning b and an appropriately located termination codon at the end of the polypeptide to be translated.

In the present invention, the expression vector for expressing the Cas protein group may contain a promoter sequence. The above promoter sequence may be appropriately selected depending on the type of eukaryotic cell serving as a host. In addition, the expression vector may contain a sequence for enhancing transcription from DNA, for example an enhancer sequence. Examples of enhancers include the SV40 enhancer (which is arranged at 100-270 bp downstream of the replication origin), the early promoter enhancer of the cytomegalovirus, and the polyoma enhancer and the adenovirus enhancer arranged downstream of the replication origin. Additionally, the expression vector may contain a sequence for stabilizing a transcribed RNA, for example a poly(A) addition sequence (polyadenylation sequence, polyA). Examples of poly(A) addition sequences include poly(A) addition sequences derived from the growth hormone gene, poly(A) addition sequences derived from the bovine growth hormone gene, poly(A) addition sequences derived from the human growth hormone gene, poly(A) addition sequences from the SV40 virus, and poly(A) additional sequences derived from the human or rabbit β-globin gene.

The number of polynucleotides encoding the Cas protein group to be incorporated into the same vector is not particularly limited as long as it is possible to exhibit the functions of the CRISPR-Cas systems in the host cell into which the expression vector has been introduced. For example, it is possible to make such a design that the polynucleotide encoding the Cas protein group is mounted on vectors of one type (of the same type). Furthermore, it is also possible to make such a design that all or some of the polynucleotide encoding the Cas protein groups is mounted on separate vectors. For example, it is possible to make such a design that the polynucleotide encoding Cascade proteins is mounted on vectors of one type (of the same type) and the polynucleotide encoding Cas3 is mounted on other vectors. It is preferable to use a method for mounting the polynucleotide encoding Cas protein groups six different types of vectors from the viewpoint of expression efficiency and the like.

Otherwise, multiple polynucleotides encoding the same proteins may be mounted on the same vectors for the purpose of controlling the expression level and the like. For example, it is possible to make such a design that the polynucleotides encoding Cas3 are arranged at two sites of vectors of one type (of the same type).

Figure 8:
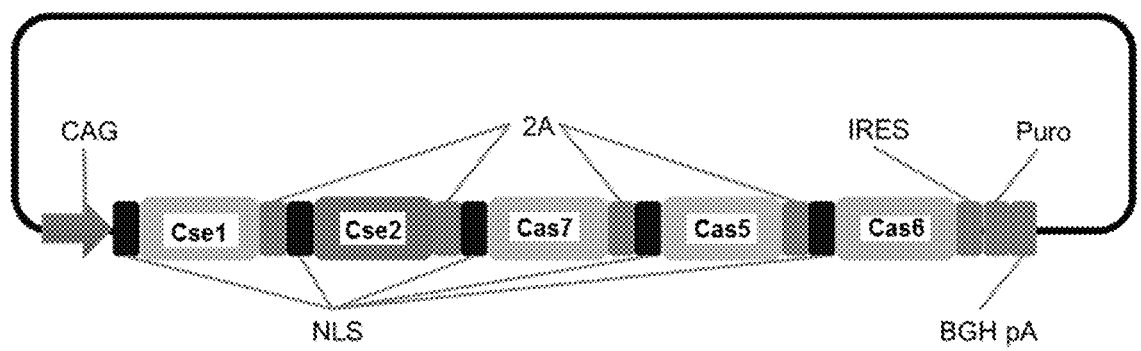
FIG. 8 is a schematic diagram showing the structure of a Cascade (2A) plasmid.

In addition, it is possible to use an expression vector which contains multiple nucleic acid sequences encoding the Cas protein group and which has nucleic acid sequences that are inserted between those multiple nucleic acid sequences and that encode amino acid sequences (2A peptides and the like) to be cleaved by intracellular proteases (for example, see the vector structure of FIG. 8). When polynucleotides having such nucleic acid sequences are transcribed and translated, polypeptide strands linked in the cell are expressed. Subsequently, due to the action of intracellular proteases, the Cas protein groups are separated, become separate proteins, and then form complexes to function. This makes it possible to regulate the amount ratio of Cas protein groups expressed intracellularly. For example, it is predicted that Cas3 and Cse1 (Cas8) will be expressed in equal amounts from an "expression vector containing one nucleic acid sequence encoding Cas3 and one nucleic acid sequence encoding Cse1 (Cas8)." In addition, it is possible to express multiple Cas protein groups with one type of expression vector, which is advantageous in excellence of handling property. On the other hand, the embodiment is usually superior in which the Cas protein groups are expressed by different expression vectors from the viewpoint of high DNA cleavage activity.

It is possible to prepare the expression vectors used in the present invention by known methods. Examples of such methods include the method described in the manual attached to a kit for preparing vectors as well as methods described in various handbooks. An example of a comprehensive handbook is [Joseph Sambrook & David W. Russell, Molecular cloning: a laboratory manual 3rd Ed., New York: Cold Spring Harbor Laboratory Press, 2001].

—Expression Vector Containing crRNA, Polynucleotide Encoding the CERNA, or the Polynucleotide—

The CRISPR-Cas3 system of the present invention includes a crRNA, a polynucleotide encoding the crRNA, or an expression vector containing the polynucleotide for the purpose of targeting to DNA for genome editing.

The crRNA is an RNA which forms part of the CRISPR-Cas system and has a nucleic acid sequence complementary to the target sequence. The CRISPR-Cas3 system of the present invention makes it possible with a crRNA to specifically recognize a target sequence and cleave the sequence. In CRISPR-Cas systems typified by the CRISPR-Cas9 system, mature crRNAs have been usually used as CRNAs. However, although the reason is not clear, it was found that use of a mature crRNA is not suitable when the CRISPR-Cas3 system is made to function in eukaryotic cells. Moreover, it was surprisingly found that it is possible to highly efficiently perform genome editing in eukaryotic cells by using a pre-crRNA instead of a mature crRNA. This fact is apparent from a comparative experiment between a mature crRNA and pre-crRNAs (FIG. 10). Therefore, it is particularly preferable to use pre-crRNAs as the crRNAs of the present invention.

The pre-crRNAs used in the present invention typically have the structures of "leader sequence-repeated sequence-spacer sequence-repeated sequence (LRSR structure)" and "repeated sequence-spacer sequence-repeated sequence (RSR structure)." The leader sequence is an AT-rich sequence and functions as a promoter to express a pre-crRNA. The repeated sequence is a sequence repeating with a spacer sequence in between, and the spacer sequence is a sequence designed in the present invention as a sequence complementary to the target DNA (originally it is a sequence derived from a foreign DNA incorporated in the course of adaptation). The pre-crRNA becomes a mature crRNA when cleaved by proteins constituting the Cascade (for example, Cas6 for types I-A, B, and D to E and Cas5 for type I-C).

Typically, the strand length of a leader sequence is 86 bases, and the strand length of a repeated sequence is 29 bases. The strand length of a spacer sequence is, for example, 10 to 60 bases, preferably 20 to 50 bases, more preferably 25 to 40 bases, and typically 32 to 37 bases. Thus, in the case of the LRSR structure, the pre-crRNA used in the present invention has a strand length of, for example, 154 to 204 bases, preferably 164 to 194 bases, more preferably 169 to 184 bases, and typically 176 to 181 bases. In addition, in the case of the RSR structure, the strand length is, for example, 68 to 118 bases, preferably 78 to 108 bases, more preferably 83 to 98 bases, and typically 90 to 95 bases.

In order to make the CRISPR-Cas3 system of the present invention function in eukaryotic cells, it is considered that the process is important by which the repeated sequences of a pre-crRNA are cleaved by the proteins constituting the Cascade. Thus, it should be understood that the above repeated sequences may be shorter or longer than the above strand length as long as such cleavage takes place. Specifically, it can be said that the pre-crRNA is a crRNA formed by adding sequences sufficient for cleavage by proteins constituting the Cascade to both ends of the mature crRNA described below. In this way, a preferred embodiment of the method of the present invention includes the step of cleaving a crRNA with proteins constituting the Cascade after introducing the CRISPR-Cas3 system into eukaryotic cells.

On the other hand, the mature crRNA generated by cleavage of a pre-crRNA has a structure of "5'-handle sequence-spacer sequence-3'-handle sequence." Typically, 5'-handle sequence is composed of 8 bases from positions 22 to 29 of the repeated sequence and is held in Cas5. In addition, 3'-handle sequence is typically composed of 21 bases from positions 1 to 21 in the repeated sequence, forms a stem loop structure with the bases of positions 6 to 21, and is held at Cas6. Thus, the strand length of a mature crRNA is usually 61 to 66 bases. Note that, since there are also mature crRNAs having no 3'-handle sequence depending on the type of the CRISPR-Cas3 system, the strand length is shortened by 21 bases in this case.

Note that the sequence of an RNA may be appropriately designed according to the target sequence for which DNA editing is desired. In addition, it is possible to synthesize an RNA using any method known in the art.

—Eukaryotic Cell—

Examples of "eukaryotic cells" in the present invention include animal cells, plant cells, algae cells, and fungal cells. In addition, examples of animal cells include mammalian cells as well as cells of, for example, fish, birds, reptiles, amphibians, and insects.

Examples of the "animal cells" include cells constituting animal bodies, cells constituting organs/tissues excised from animals, and cultured cells derived from animal tissues. Specific examples include germ cells such as oocytes and sperm; embryonic cells of embryos at various stages (such as 1-cell embryos, 2-cell embryos, 4-cell embryos, 8-cell embryos, 16-cell embryos, and morula embryos); stem cells such as induced pluripotent stem (iPS) cells and embryonic stem(ES) cells; and somatic cells such as fibroblasts, hematopoietic cells, neurons, muscle cells, bone cells, liver cells, pancreatic cells, brain cells, and kidney cells. It is possible to use oocytes before fertilization and after fertilization as the oocytes used for preparing genome-edited animals, preferably oocytes after fertilization, that is, fertilized eggs. Particularly preferably, the fertilized eggs are from pronuclear stage embryos. Oocytes can be thawed and used after freezing.

In the present invention, "mammalian" is a concept including human and non-human mammals. Examples of non-human mammals include cloven-hoofed mammals such as cattle, boars, pigs, sheep, and goats, odd-toed mammals such as horses, rodents such as mice, rats, guinea pigs, hamsters, and squirrels, lagomorphs such as rabbits, and carnivores such as dogs, cats, and ferrets. The non-human mammals described above may be livestock or companion animals (pets), or may be wild animals.

Examples of the "plant cells" include cells of cereals, oil crops, feed crops, fruits, and vegetables. Examples of the "plant cells" include cells constituting plant bodies, cells constituting organs and tissues separated from plants, and cultured cells derived from plant tissues. Examples of organs and tissues of plants include leaves, stems, shoot apexes (growing points), roots, tubers, and calli. Examples of plants include rice, corn, banana, peanut, sunflower, tomato, oilseed rape, tobacco, wheat, barley, potato, soybean, cotton, and carnation as well as propagation materials thereof (for example, seeds, tuberous roots, and tubers).

—DNA Editing—

In the present invention, "editing the DNA of a eukaryotic cell" may be a step in which the DNA of a eukaryotic cell is edited in vivo or in vitro. In addition, "editing the DNA" means the operations exemplified by the following (including types combinations thereof).

Note that, in the present specification, the DNA used in the above context includes not only DNA present in the nucleus of a cell but also exogenous DNA and DNA present other than the nucleus of a cell such as mitochondrial DNA.

1. cleaving the DNA strand at the target site
2. deleting a base of the DNA strand at the target site
3. inserting a base into the DNA strand at the target site
4. replacing a base of the DNA strand at the target site
5. modifying a base of the DNA strand at the target site
6. modulating the transcription of the DNA (gene) at the target site.

One embodiment of the CRISPR-Cas3 system of the present invention uses a protein having an enzymatic activity for modifying the target DNA by a method other than introducing DNA cleavage. This embodiment can be achieved by, for example, fusing Cas3 or Cascade with a heterologous protein having a desired enzymatic activity into a chimeric protein. Thus, "Cas3" and "Cascade" in the present invention also include such fusion proteins. Examples of the enzymatic activity of the protein to be fused include, but not limited to, deaminase activity (for example, cytidine deaminase activity and adenosine deaminase activity), methyl transferase activity, demethylation enzyme activity, DNA repair activity, DNA damage activity, dismutase activity, alkylation activity, depurination activity, oxidation activity, pyrimidine dimer formation activity, integrase activity, transposase activity, recombinase activity, polymerase activity, ligase activity, photoreactivation enzyme activity, and glycosylase activity. In this case, the nuclease activity or the helicase activity of Cas3 is not necessarily required. For this reason, it is possible to use as Cas3 a mutant in which some or all of these activities are deleted (for example, a mutant of D domain H74A (dnCas3), a mutant of K320N of SF2 domain motif 1 (dhCas3), and a double mutant of S483A/T485A of SF2 domain motif 3 (dh2Cas3)). Precise genome editing is possible by replacing bases without causing large deletion at the target site if, for example, a fusion protein of a deaminase and a mutant in which some or all of the nuclease activities of Cas3 have been eliminated is used as a constituent element of the CRISPR-Cas3 system of the present invention. The method for applying a deaminase to the CRISPR-Cas systems s well known (Nishida K. et al., Targeted nucleotide editing using hybrid prokaryotic and vertebrate adaptive immune systems, Science, DOI: 10.1126/science.aaf8729, (2016)), and it suffices to apply the method to the CRISPR-Cas3 system of the present invention.

Another embodiment of the CRISPR-Cas3 system of the present invention regulates gene transcription at the binding site of the present system without DNA cleavage. This embodiment can be achieved by, for example, fusing Cas 3 or Cascade with the desired transcription regulating protein into a chimeric protein. Thus, "Cas3" and "Cascade" in the present invention also include such fusion proteins. Examples of the transcription regulating protein include, but not limited to, light inducible transcriptional regulators, small molecule/drug responsive transcriptional regulators, transcription factors, and transcriptional repressors. In this case, the nuclease activity or the helicase activity of Cas3 is not necessarily required. For this reason, it is possible to use as Cas3 a mutant in which some or all of these activities are deleted (for example, a mutant of D domain H74A (dnCas3), a mutant of K320N of SF2 domain motif 1 (dhCas3), and a double mutant of S483A/T485A of SF2 domain motif 3 (dh2Cas3)). Methods for applying a transcription regulating protein to the CRISPR-Cas systems are known to those skilled in the art.

Additionally, in the CRISPR-Cas3 system of the present invention, consider the case of, for example, using a mutant in which some or all of the nuclease activities of Cas3 are deleted. Proteins having other nuclease activities may be fused with Cas3 or Cascade. Such embodiment is included in the present invention.

Besides, in the CRISPR-Cas3 system of the present invention, consider the case of using a mutant in which some or all of the nuclease activities of Cas3 are deleted and using the activities of other proteins in editing DNA. The "DNA cleavage activity" in the present specification is appropriately interpreted as various activities which those proteins have.

Moreover, DNA editing may be performed on DNA contained in a specific cell within an individual. Such DNA editing can be performed on, for example, a specific cell as a target among cells constituting the body of an animal or plant.

No limitation is imposed on the method for introducing the molecules constituting the CRISPR-Cas3 system of the present invention into eukaryotic cells in the form of a polynucleotide or an expression vector containing the polynucleotide. Examples of the method include electroporation, the calcium phosphate method, the liposome method, the DEAE dextran method, the microinjection method, cationic lipid mediated transfection, electroporation, transduction, and infection using virus vectors. Such methods are described in many standard laboratory manuals such as "Leonard G. Davis et al., Basic methods in molecular biology, New York: Elsevier, 1986."

No limitation is imposed on the method for introducing the molecules of the CRISPR-Cas3 system of the present invention into eukaryotic cells in the form of a protein. Examples thereof include electroporation, cationic lipid mediated transfection, and microinjection.

The DNA editing according to the present invention can be applied to various fields. Application examples include gene therapy, breed improvement, production of transgenic animals or cells, production of useful substances, and life science research.

Known methods can be used as methods for preparing non-human individuals from cells. Germ cells or pluripotent stem cells are usually used in the case of producing non-human individuals from cells of animals. For example, molecules constituting the CRISPR-Cas3 system of the present invention are introduced into an oocyte. The obtained oocyte is then transplanted into the uterus of a female non-human mammal which has been placed in a pseudopregnant state. After that, a litter is obtained. The transplantation can be carried out in a fertilized egg of 1-cell embryo, 2-cell embryo, 4-cell embryo, 8-cell embryo, 16-cell embryo, or morula embryo. If desired, the oocyte can be cultured under suitable conditions until transplantation. Transplantation and culture of the oocyte can be carried out based on a conventionally known method (Nagy A. et al., Manipulating the Mouse Embryo, Cold Spring Harbour, New York: Cold Spring Harbour Laboratory Press, 2003). It is also possible to obtain, from the obtained non-human individual, clones or descendants in which the desired DNA has been edited.

In addition, it has long been known that somatic cells of plants possess differentiation totipotency, and methods for regenerating plants from plant cells of various plants have been established. Therefore, it is possible to obtain a plant in which the desired DNA is knocked in by introducing the molecules constituting the CRISPR-Cas3 system of the present invention into plant cells and regenerating plants from the obtained plant cells. It is also possible to obtain progeny, clones, or propagation materials in which the desired DNA has been edited. As a method of redifferentiating a plant tissue by tissue culture to obtain an individual, it is possible to use a method established in the present technical field (Protocols for Plant Transformation, edited by TABEI Yutaka, Kagaku-Dojin, pp. 340-347 (2012)).

[2] Kit Used in CRISPR-Cas3 System

A kit used in the CRISPR-Cas3 system of the present invention comprises the following (A) and (B).

(A) a Cas3 protein, a polynucleotide encoding the protein, or an expression vector containing the polynucleotide, and (B) a Cascade protein, a polynucleotide encoding the protein, or an expression vector containing the polynucleotide.

The kit may further comprises a CERNA, a polynucleotide encoding the crRNA, or an expression vector containing the polynucleotide The constituent elements of the kit of the present invention may be in an embodiment in which all or some of them are mixed, or may be in an embodiment in which each of them is independent.

It is possible to use the kit of the present invention in fields such as pharmaceutical preparations, food, animal husbandry, fishery, industry, bioengineering, and life science research.

Hereinafter, the kit of the present invention is described assuming pharmaceutical preparations (drugs). Note that, in the case of using the above-described kit in fields such as animal husbandry, bioengineering, and life science research, the kit can be used by appropriately interpreting the following explanation based on common technical knowledge in those fields.

It is possible to prepare a pharmaceutical preparation for editing DNA of animal cells including humans by usual methods using the CRISPR-Cas3 system of the present invention. More specifically, the pharmaceutical preparation can be prepared by formulating the molecules constituting the CRISPR-Cas3 system of the present invention with, for example, a pharmaceutical preparation additive.

Here, the "pharmaceutical preparation additive" means a substance other than the active ingredients contained in the pharmaceutical preparation. The pharmaceutical preparation additive is a substance contained in a pharmaceutical preparation for the purpose of facilitating formulation, stabilizing the quality, enhancing the utility, and the like. Examples of the pharmaceutical preparation additive described above can include excipients, binders, disintegrants, lubricants, fluidizers (solid antistatic agents), colorants, capsule coats, coating agents, plasticizers, taste-making agents, sweeteners, flavoring agents, solvents, dissolution assisting agents, emulsifiers, suspending agents (pressure sensitive adhesives), thickeners, pH adjusters (acidifiers, alkalizers, and buffers), humectants (solubilizers), antibacterial preservatives, chelating agents, suppository bases, ointment bases, curing agents, softeners, medical water, propellants, stabilizers, and preservatives. These pharmaceutical preparation additives can readily be selected by those skilled in the art according to the intended dosage form and route of administration as well as standard pharmaceutical practice.

In addition, the pharmaceutical preparation for editing DNA of animal cells using the CRISPR-Cas3 system of the present invention may contain additional active ingredients. The additional active ingredients are not particularly limited and can be appropriately designed by those skilled in the art.

Specific examples of the active ingredients and pharmaceutical preparation additives described above can be learned according to the standards established by, for example, the US Food and Drug Administration (FDA), the European Medicines Authority (EMA), the Japanese Ministry of Health, Labor and Welfare.

Examples of methods for delivering a pharmaceutical preparation to the desired cells include methods using virus vectors targeting the cells (adenovirus vectors, adeno-associated virus vectors, lentivirus vectors, Sendai virus vectors, and the like) or antibodies specifically recognizing the cells. The pharmaceutical preparation can take any dosage form depending on the purpose. Also, the above pharmaceutical preparation is properly prescribed by doctors or medical professionals.

The kit of the present invention preferably further includes an instruction manual.

EXAMPLES

Hereinafter, the present invention is described in more detail with reference to Examples, but the present invention is not limited only to the following examples.

A. Establishment of CRISPR-Cas3 System in Eukaryotic Cell

[Material and Method]

[1] Preparation of Reporter Vectors Containing Target Sequences

The target sequences were the sequence derived from the human CCR5 gene (SEQ ID NO: 19) and the spacer sequence of *E. coli* CRISPR (SEQ ID NO: 22).

For the purpose of inserting the target sequences into the vectors, a synthetic polynucleotide (SEQ ID NO: 20) containing the target sequence derived from the human CCR5 gene 2 ID NO: 19) and a synthetic polynucleotide (SEQ ID NO: 21) containing a sequence complementary to the above target sequence (SEQ ID NO: 19) were a synthetic prepared. Similarly, polynucleotide (SEQ ID NO: 23) containing the target sequence derived from the spacer sequence of *E. coli* CRISPR (SEQ ID NO: 22) and a synthetic polynucleotide (SEQ ID NO: 24) containing a sequence complementary to the above target sequence (SEQ ID NO: 22) were prepared. All of the above synthetic polynucleotides were obtained from Hokkaido System Science Co., Ltd.

The above polynucleotides were inserted into the reporter vectors by the method described in [Sakuma T et al. (2013) Efficient TALEN construction and evaluation methods for human cell and animal applications, Genes to Cells, Vol. 18 (Issue 4), pp. 315-326]. The outline is as follows. First, polynucleotides having sequences complementary to each other (the polynucleotide of SEQ ID NO: 20 and the polynucleotide of SEQ ID NO: 21; the polynucleotide of SEQ ID NO: 23 and the polynucleotide of SEQ ID NO: 24) were heated at 95° C. for 5 minutes, and then cooled to room temperature and hybridized. A block incubator (BI-515A, Astec) was used for the above step. Next, the polynucleotide hybridized to form a double-stranded structure was inserted into the base vector to prepare a reporter vector.

Figure 4A:
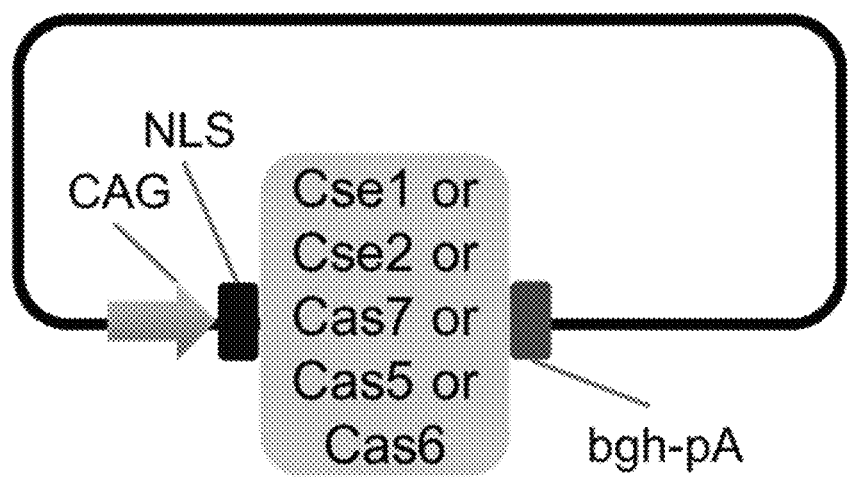
FIG. 4A is a schematic diagram showing the structure of a Cascade plasmid.
Figure 4B:
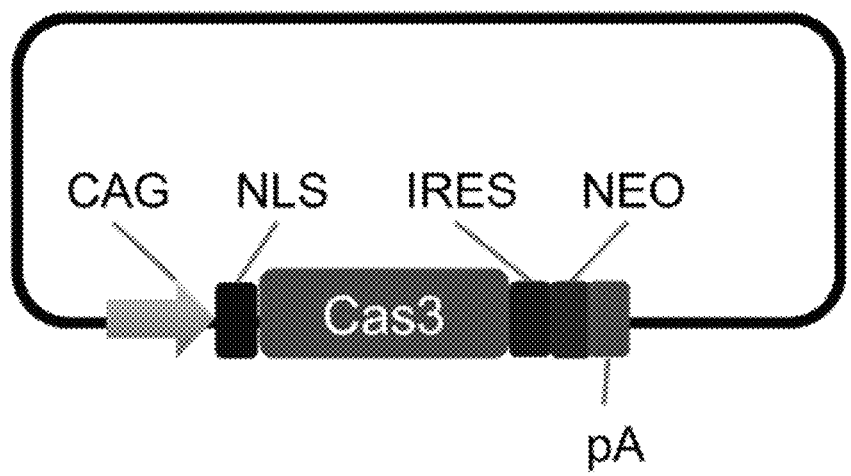
FIG. 4B is a schematic diagram showing the structure of a Cas3 plasmid.
Figure 4C:
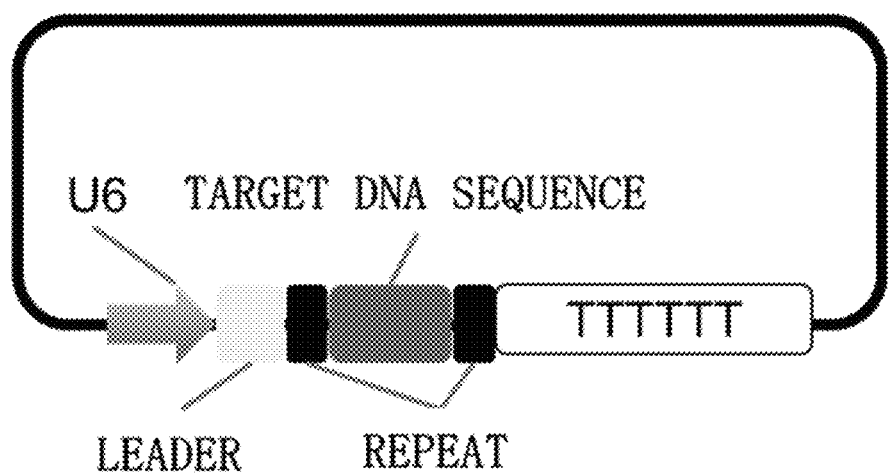
FIG. 4C is a schematic diagram showing the structure of a pre-crRNA plasmid.
Figure 4D:
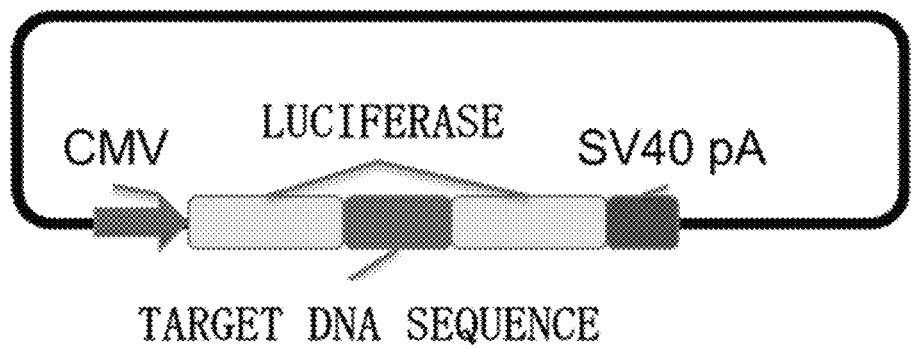
FIG. 4D is a schematic diagram showing the structure of a reporter vector (including the target sequence).

The sequences of the prepared reporter vectors are shown at SEQ ID NO: 31 (reporter vector containing the target sequence derived from the human CCR5 gene) and SEQ ID NO: 32 (reporter vector containing the target sequence derived from the spacer sequence of *E. coli* CRISPR). In addition, the structure of reporter vector is shown in FIG. 4D.

[2] Preparation of Cse1 (Cas8), Cse2 (Cas11), Cas5, Cas6, Cas7, and crRNA Expression Vectors

[Amplification and Preparation of Inserts]

Consider polynucleotides having modified nucleic acid sequences encoding Cse1 (Cas8), Cse2 (Cas11), Cas5, Cas6, and Cas7 (with SEQ ID NO: 2, SEQ ID NO: 3, SEQ ID NO: 4, SEQ ID NO: 5, and SEQ ID NO: 6, respectively). First, production of polynucleotides linked in the order of SEQ ID NO: 2-SEQ ID NO: 3-SEQ ID NO: 6-SEQ ID NO: 4-SEQ ID NO: 5 (polynucleotides having linked nucleic acid sequences for encoding Cse1 (Cas8)-Cse2 (Cas11)-Cas7-Cas5-Cas6 in this order) was outsourced to GenScript Corporation for purchase. The nucleic acid sequences encoding the proteins of Cse1 (Cas8)-Cse2 (Cas11)-Cas7-Cas5-Cas6 were linked with 2A peptides (amino acid sequence: GSGATNFSLLKQAGDVEENPGP (SEQ ID NO: 58)).

Note that the nucleic acid sequences encoding the 2A peptides were slightly different depending on the Cas protein linkage sites and were as follows.

```
The sequence between Cse1 (Cas8) and Cse2 (Cas11):
                                        (SEQ ID NO: 59)
GGAAGCGGAGCAACCAACTTCAGCCTGCTGAAGCAGGCCGGCGATGTGGA

GGAGAATCCAGGCCCC.

The sequence between Cse2 (Cas11)and Cas7:
                                        (SEQ ID NO: 60)
GGCTCCGGCGCCACCAATTTTTCTCTGCTGAAGCAGGCAGGCGATGTGGA

GGAGAACCCAGGACCT.

The sequence between Cas7 and Cas5:
                                        (SEQ ID NO: 61)
GGATCTGGAGCCACCAATTTCAGCCTGCTGAAGCAAGCAGGCGACGTGGA

AGAAAACCCAGGACCA.

The sequence between Cas5 and Cas6:
                                        (SEQ ID NO: 62)
GGATCTGGGGCTACTAATTTTTCTCTGCTGAAGCAAGCCGGCGACGTGGA

AGAGAATCCAGGACCG.
```

Next, each of the polynucleotides was amplified under the PCR conditions (primer and time course) in the following table. For PCR, 2720 Thermal cycler (applied biosystems) was used.

TABLE 1

| Primer | Sequence | Timecourse |
| --- | --- | --- |
| Cse1-U | GCAAAGAATTCAGAT<br>CTCCACCATGCCTAA<br>GAAGAAGAGAAAAGT<br>GAACCTGCTGATTGA<br>C<br>(SEQ ID NO: 36) | 98° C. (10 Sec) →<br>68° C. (1 Min)<br>35 Cycles |
| Cse1-L | TCATCGATGCATCTC<br>GAGTTATCCATTAGA<br>AGGTCCTCCCTGTGG<br>CTTC<br>(SEQ ID NO: 37) | |
| Cse2-U | GCAAAGAATTCAGAT<br>CTCCACCATGCCCAA<br>GAAGAAGCGGAAGGT<br>GGCCGATGAGATCGA<br>C<br>(SEQ ID NO: 38) | 98° C. (10 Sec) →<br>68° C. (1 Min)<br>35 Cycles |
| Cse2-L | TCATCGATGCATCTC<br>GAGTTAGGCGTTCTT<br>ATTTGTGGTCAGCAC<br>GAAG<br>(SEQ ID NO: 39) | |

TABLE 1-continued

| Primer | Sequence | Timecourse |
|---|---|---|
| Cas5-U | GCAAAGAATTCAGAT CTCCACCATGCCCAA GAAGAAGCGGAAGGT GTCCAATTTCATCAA C (SEQ ID NO: 40) | |
| Cas5-L | TCATCGATGCATCTC GAGTTATGCCTCTCC ATTGTTCCGCACCCA GCTC (SEQ ID NO: 41) | |
| Cas6-U | GCAAAGAATTCAGAT CTCCACCATGCCCAA GAAGAAGCGGAAAGT GTACCTGAGCAAAGT G (SEQ ID NO: 42) | |
| Cas6-L | TCATCGATGCATCTC GAGTTACAGAGGTGC CAGTGACAGCAGCCC AC (SEQ ID NO: 43) | |
| Cas7-U | GCAAAGAATTCAGAT CTCCACCATGCCCAA GAAGAAGCGGAAGGT GCGCTCCTACCTGAT C (SEQ ID NO: 44) | 98° C. (10 Sec) → 68° C. (1 Min 40 Sec) 35 Cycles |
| Cas7-L | TCATCGATGCATCTC GAGTTACTGGCTCAC GTCCATTCCTCCCTT GATC (SEQ ID NO: 45) | |

Polynucleotides having the following complementary sequences were obtained as polynucleotides having nucleic acid sequences for expressing crRNA.
1. polynucleotides for expressing crRNA corresponding to the sequence derived from the human CCR5 gene (SEQ ID NOS: 25 and 26, obtained from Hokkaido System Science Co., Ltd.)
2. polynucleotides for expressing crRNA corresponding to the spacer sequence of *E. coli* CRISPR (SEQ ID NOS: 27 and 28, obtained from Hokkaido System Science Co., Ltd.)
3. polynucleotides for expressing crRNA corresponding to the sequence derived from the human EMX1 gene (SEQ ID NOS: 29 and 30, obtained from Pharmac).

[Ligation and Transformation]

As a substrate plasmid, pPB-CAG-EBNXN (supplied from Sanger Center) was used. In NEB buffer, 1.6 µg of the substrate plasmid, 1 µl of restriction enzyme BglII (New England Biolabs), and 0.5 µl of XhoI (New England Biolabs) were mixed and reacted at 37° C. for 2 hours. The cleaved substrate plasmids were purified with Gel extraction kit (Qiagen).

The substrate plasmids thus prepared and the above inserts were ligated with a Gibson Assembly system. Ligation was carried out in accordance with the protocol of the Gibson Assembly system with the ratio of the substrate plasmids to the inserts being 1:1 (at 50° C. for 25 minutes, total volume of the reaction solution: 8 µL).

Subsequently, 6 µL of a solution of the plasmids obtained above (ligation reaction solution) and competent cells (prepared by Takeda Laboratory) were used to perform transformation in accordance with the usual method.

Thereafter, plasmid vectors were purified from the transformed *E. coli* by the alkaline prep method. Briefly, the plasmid vectors were recovered using QIAPREP® SPIN MINIPREP™ Kit (Qiagen), and the recovered plasmid vectors were purified by the ethanol precipitation method and then adjusted to have a concentration of 1 µg/µL in a TE buffer solution.

The structure of each plasmid vector is shown in FIGS. 4(*a*) to 4(*c*). In addition, the nucleic acid sequences of pre-crRNA expression vectors are shown at SEQ ID NO: 33 (expression vector for expressing crRNA corresponding to the sequence derived from the human CCR5 gene), SEQ ID NO: 34 (expression vector for expressing crRNA corresponding to the spacer sequence of *E. coli* CRISPR), and SEQ ID NO: 35 (expression vector for expressing crRNA corresponding to the sequence derived from the human EMX1 gene).

[3] Preparation of Cas3 Expression Vector

A polynucleotide having a modified nucleic acid sequence encoding Cas3 (SEQ ID NO: 1) was obtained from Genscript. Specifically, pUC57 vector incorporating the polynucleotide described above was obtained from Genscript.

The above vector was cleaved with restriction enzyme NotI. Next, 2 U of Klenow Fragment (Takara Bio Inc.) and 1 µL of 2.5 mM dNTP Mixture (Takara Bio Inc.) were used to smooth the edge of the fragment. Thereafter, the above fragment was purified using Gel extraction (Qiagen). The purified fragment was further cleaved with restriction enzyme XhoI and purified using Gel extraction (Qiagen).

The purified fragment was ligated using a substrate plasmid (pTL2-CAG-IRES-NEO vector, prepared by Takeda Laboratory) and a ligation kit (Mighty Mix, Takara Bio Inc.). After that, transformation and purification were carried out by the same operations as in [2]. The recovered plasmid vector was prepared to have a concentration of 1 µg/µL in a TE buffer solution.

[4] Preparation of Plasmid Vector Containing BPNLS

Figure 7:
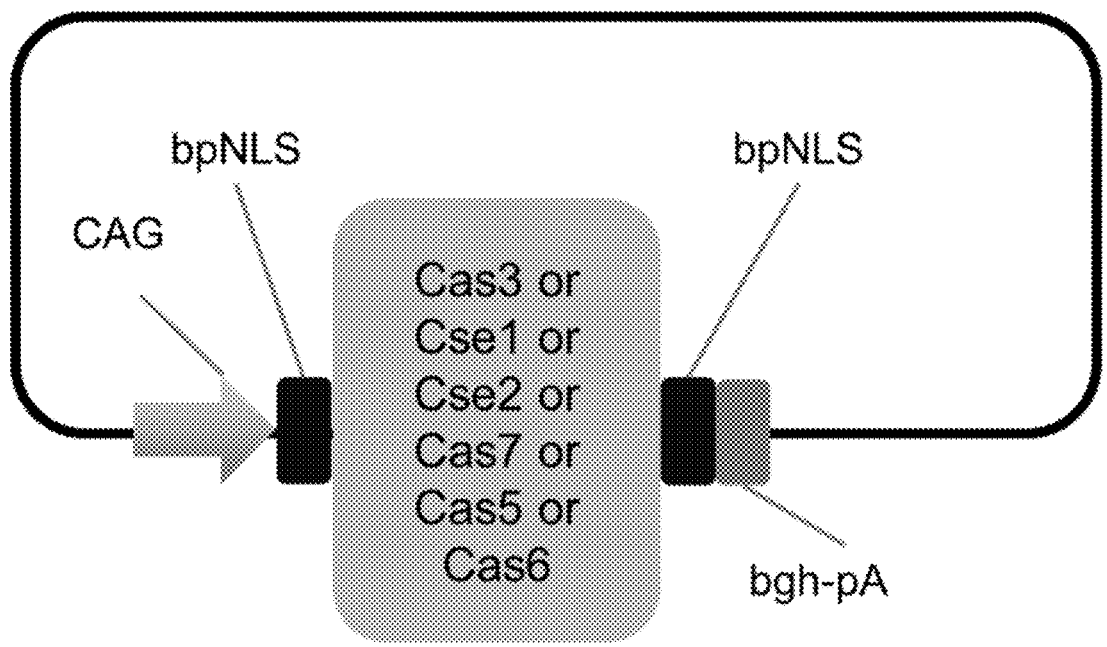
FIG. 7 is a schematic diagram showing the structure of a Cas3/Cascade plasmid added with bpNLSs.

Prepared were Cas3, Cse1 (Cas8), Cse2 (Cas11), Cas5, Cas6, and Cas7 expression vectors in which BPNLSs were connected to 5'-end and 3'-end (see FIG. 7).

The production of an insert for each Cas protein group containing BPNLSs at both ends was ordered to Thermo Fisher Scientific. The specific sequence of the above insert is (AGATCTTAATACGACTCACTATAGGGAGAGC-CGCCACCATGGCC: SEQ ID NO: 56)-(any one of SEQ ID NOS: 7 to 12)-(TAATATCCTCGAG: SEQ ID NO: 57). SEQ ID NO: 56 is a sequence provided with a cleavage site by BglII. SEQ ID NO: 57 is a sequence provided with a cleavage site by XhoI.

The pMK vector incorporating the above sequence was cleaved with restriction enzymes BglII and XhoI and purified using Gel extraction (Qiagen). The purified fragment was ligated using a substrate plasmid (pPB-CAG-EBNXN, supplied from Sanger Center) and a ligation kit (Mighty Mix, Takara Bio Inc.). After that, transformation and purification were carried out by the same operations as in [2]. The recovered plasmid vector was prepared to have a concentration of 1 µg/µL in a TE buffer solution.

[5] Preparation of Plasmid Vector Containing Cascade (2A)

Prepared was an expression vector in which the nucleic acid sequence had Cse1 (Cas8), Cse2 (Cas11), Cas7, Cas5, and Cas6 linked in this order. More specifically, prepared was an expression vector having an arrangement of (NLS-Cse1 (Cas8): SEQ ID NO: 2)-2A-(NLS-Cse2 (Cas11): SEQ ID NO: 3)-2A-(NLS-Cas7: SEQ ID NO: 6)-2A-(NLS-Cas5:

SEQ ID NO: 4)-2A-(NLS-Cas6: SEQ ID NO: 5) (see FIG. 8). Note that the amino acid sequence of NLS is PKKKRKV (SEQ ID NO: 52), and the nucleic acid sequence is CCCAAGAAGAAGCGGAAGGTG (SEQ ID NO: 53). In addition, the amino acid sequence of 2A peptide is GSGATNFSLLKQAGDVEENPGP (SEQ ID NO: 58) (the corresponding nucleic acid sequences are SEQ ID NOs: 59 to 62).

A polypeptide having the above nucleic acid sequence was obtained from GenScript. The pUC57 vector incorporating the above sequence was cleaved with restriction enzyme ECORI-HF and purified using Gel extraction (Qiagen). The purified fragment was ligated using a substrate plasmid (pTL2-CAG-IRES-Puro vector, prepared by Takeda Laboratory) and a ligation kit (Mighty Mix, Takara Bio Inc.). After that, transformation and purification were carried out by the same operations as in [2]. The recovered plasmid vector was prepared to have a concentration of 1 μg/μL in a TE buffer solution.

Example A-1

The cleavage activity of the target sequence of the exogenous DNA was evaluated as follows. A crRNA and Cas3, Cse1 (Cas8), Cse2 (Cas11), Cas5, Cas6, and Cas7 added with nuclear localization signals to have a modified nucleic acid sequence were expressed in HEK (human embryonic kidney) 293T cells.

Prior to transfection, the HEK 293T cells were cultured in a 10 cm dish. Culture of the HEK 293T cells was carried out in EF medium (GIBCO) at 37° C. in a 5% $CO_2$ atmosphere. The density of HEK 293T cells in the EF medium was adjusted to $3 \times 10^{4/100}$ μL.

In addition, 100 ng of the above reporter vector; 200 ng of each of the Cas3 plasmid, the Cse1 (Cas8) plasmid, the Cse2 plasmid, the Cas5 plasmid, the Cas6 plasmid, the Cas7 plasmid, and the crRNA plasmid; 60 ng of pRL-TK vector (capable of expressing *Renilla* luciferase, Promega); and 300 ng of pBluescript® II KS (+) vector (Agilent Technologies) were mixed in 25 μL of Opti-MEM™ (Thermo Fisher Scientific). The conditions using the reporter vector having the target sequence derived from CCR5 as the reporter vector correspond to 1 in FIG. 1, and the conditions using the reporter vector having the spacer sequence of *E. coli* CRISPR correspond to 10 in FIG. 1.

Next, 1.5 μL of LIPOFECTAMINE™ 2000 (Thermo Fisher Scientific) and 25 UL of OPTIMEM™ (Thermo Fisher Scientific) were mixed and incubated at room temperature for 5 minutes. Thereafter, the above plasmid+ OPTIMEM™ mixture and LIPOFECTAMINE™ 2000+OPTIMEM™ mixture were mixed and incubated at room temperature for 20 minutes. The resulting mixture was mixed with 1 mL of the above EF medium containing HEK 293T cells and seeded in a 96-well plate (seeded in a total of 12 wells, 1 well per combination of vectors).

After culturing at 37° C. in a 5% $CO_2$ atmosphere for 24 hours, a dual-Luciferase assay was carried out in accordance with the protocol of the DUAL-GLO™ Luciferase assay system (Promega). For measurement of luciferase and *Renilla* luciferase, CENTRO XS 3 LB 960™ (BERTHOLD TECHNOLOGIES) was used.

The same experiment was conducted under the following conditions as a control experiment.

1. Instead of any one of the Cas3 plasmid, the Cse1 (Cas8) plasmid, the Cse2 (Cas11) plasmid, the Cas5 plasmid, the Cas6 plasmid, and the Cas7 plasmid, the same amount of pBluescript® II KS (+) vector (Agilent Technologies) was mixed for expression (2 to 7 in FIG. 1).
2. Instead of the crRNA plasmid used in the above procedure, plasmids for expressing a crRNA not complementary to the target sequence were mixed. Specifically, for the purpose of expression, plasmids for expressing the CERNA corresponding to the spacer sequence of *E. coli* CRISPR were mixed for the target sequence derived from the CCR5 gene (8 in FIG. 1), and plasmids for expressing the crRNA corresponding to the sequence derived from the CCR5 gene were mixed when targeting the spacer sequence of *E. coli* CRISPR (11 in FIG. 1).
3. As negative controls, only a reporter vector having the target sequence derived from CCR5 (9 in FIG. 1) and only a reporter vector having the spacer sequence of *E. coli* CRISPR (12 in FIG. 1) were expressed.

(Results)

Figure 1:
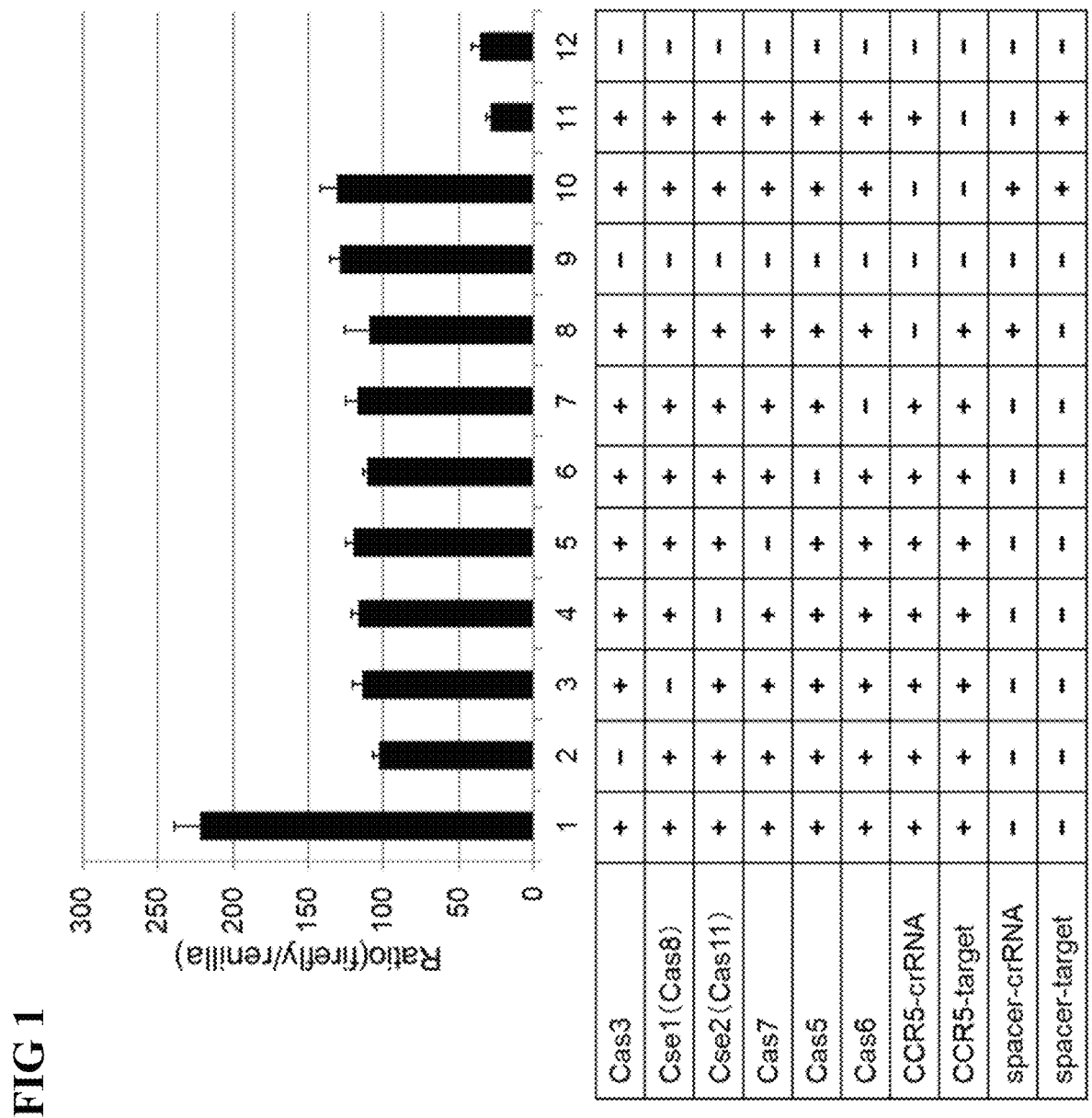
FIG. 1 is the results of SSA assay measuring cleavage activity against exogenous DNA.

The results of the dual-Luciferase assay are shown in the graph of FIG. 1, and the experimental conditions are shown in the lower table of FIG. 1. In FIG. 1, "CCR5-target" and "spacer-target" represent the target sequence derived from CCR5 and the spacer sequence of *E. coli* CRISPR, respectively. In addition, "CCR5-crRNA" and "spacer-crRNA" represent the sequence complementary to CCR5-target and the sequence to spacer-target, complementary respectively.

In FIG. 1, the system into which the crRNA plasmid complementary to the target sequence and all of the Cas3 plasmid, the Cse1 (Cas8) plasmid, the Cse2 (Cas11) plasmid, the Cas5 plasmid, the Cas6 plasmid, and the Cas7 plasmid were introduced exhibited cleavage activity higher than that of other systems (compare between 1 and 2 to 8, and between 10 and 11). Therefore, it was found that it is possible to express Cas3, Cse1 (Cas8), Cse2 (Cas11), Cas5, Cas6, and Cas7 in human cells by using the expression vectors according to an embodiment of the present invention.

In addition, it was suggested that introducing of the above expression vectors into human cells forms Cas3, Cascade, and crRNA complexes in human cells and cleaves the target sequence.

Furthermore, in FIG. 1, comparison between 8 and 9 and between 11 and 12 reveals that cleavage activity was equivalent to that of the negative controls in a system expressing a crRNA not complementary to the target sequence. In other words, it was suggested that the CRISPR-Cas3 system of the present invention can specifically cleave sequences complementary to crRNA in mammalian cells.

Example A-2

An experiment was conducted to evaluate whether or not it is possible to cleave endogenous DNA of human cells by type I CRISPR-Cas systems using the same method as in Example A-1.

Specifically, the nucleic acid sequence in human cells was modified to express pre-crRNA and Cas3, Cse1 (Cas8), Cse2 (Cas11), Cas5, Cas6, and Cas7 added with nuclear localization signals, and evaluation was conducted on whether or not the sequence of the endogenous CCR5 gene of the cells would be cleaved.

The same HEK 239T cells as in Example A-1 were seeded in a 24-well plate at a density of $1 \times 10^5$ cells/well and cultured for 24 hours.

Mixed with 50 μL of OPTI-MEM™ (Thermo Fisher Scientific) were 1 μg of the Cas3 plasmid, 1.3 μg of the Cse1

(Cas8) plasmid, 1.3 μg of the Cse2 (Cas11) plasmid, 1.1 μg of the Cas5 plasmid, 0.8 μg of the Cas6 plasmid, 0.3 μg of the Cas7 plasmid, and 1 μg of the crRNA plasmid. Subsequently, a mixture of 5 μL of LIPOFECTAMINE™ (registered trademark) 2000 (Thermo Fisher Scientific), 50 μL of OPTI-MEM™ Thermo Fisher Scientific), and 1 mL of EF medium was added to the above DNA mixture. Thereafter, 1 mL of the resulting mixture was added to the above 24-well plate.

After culturing at 37° C. in a 5% $CO_2$ atmosphere for 24 hours, the medium was replaced with 1 mL of EF medium. Past 48 hours following transfection (24 hours after medium replacement), the cells were harvested and adjusted to a concentration of $1 \times 10^4$ cells/5 μL in PBS.

The above cells were heated at 95° C. for 10 minutes. Next, 10 mg of proteinase K was followed by incubation at 55° C. for 70 minutes. Furthermore, the product heat-treated at 95° C. for 10 minutes was used as a template for PCR.

By performing 35 cycles of 2-step PCR, 10 μL of the above template was amplified. Here, primers having the sequences of SEQ ID NOs: 47 and 48 were used as primers for PCR. In addition, KOD FX (Toyobo Co., Ltd.) was used as a DNA polymerase, and the 2-step PCR procedure was in accordance with the protocol attached to KOD FX. The product amplified by PCR was purified using QIAQUICK™ PCR Purification Kit (QIAGEN). The specific procedure was in accordance with the protocol attached to the above kit.

The dA was added to 3'-end of the purified DNA obtained using rTaq DNA polymerase (Toyobo Co., Ltd.). The purified DNA was subjected to electrophoresis in a 2% agarose gel, and a band of about 500 to 700 bp was cut out. Then, DNA was extracted from the cut gel and purified using a Gel extraction kit (QIAGEN). Next, TA cloning was carried out using PGEM-TR EASY VECTOR SYSTEMS™ (Promega), and the above DNA was cloned. Finally, DNA cloned by alkaline prep method was extracted and analyzed by Sanger sequence. For the analysis, BIGDYE (registered trademark) Terminator v 3.1 Cycle Sequencing Kit (Thermo Fisher Scientific) and APPLIED BIOSYSTEMS™ 3730 DNA Analyzer (Thermo Fisher Scientific) were used.

Figure 2:
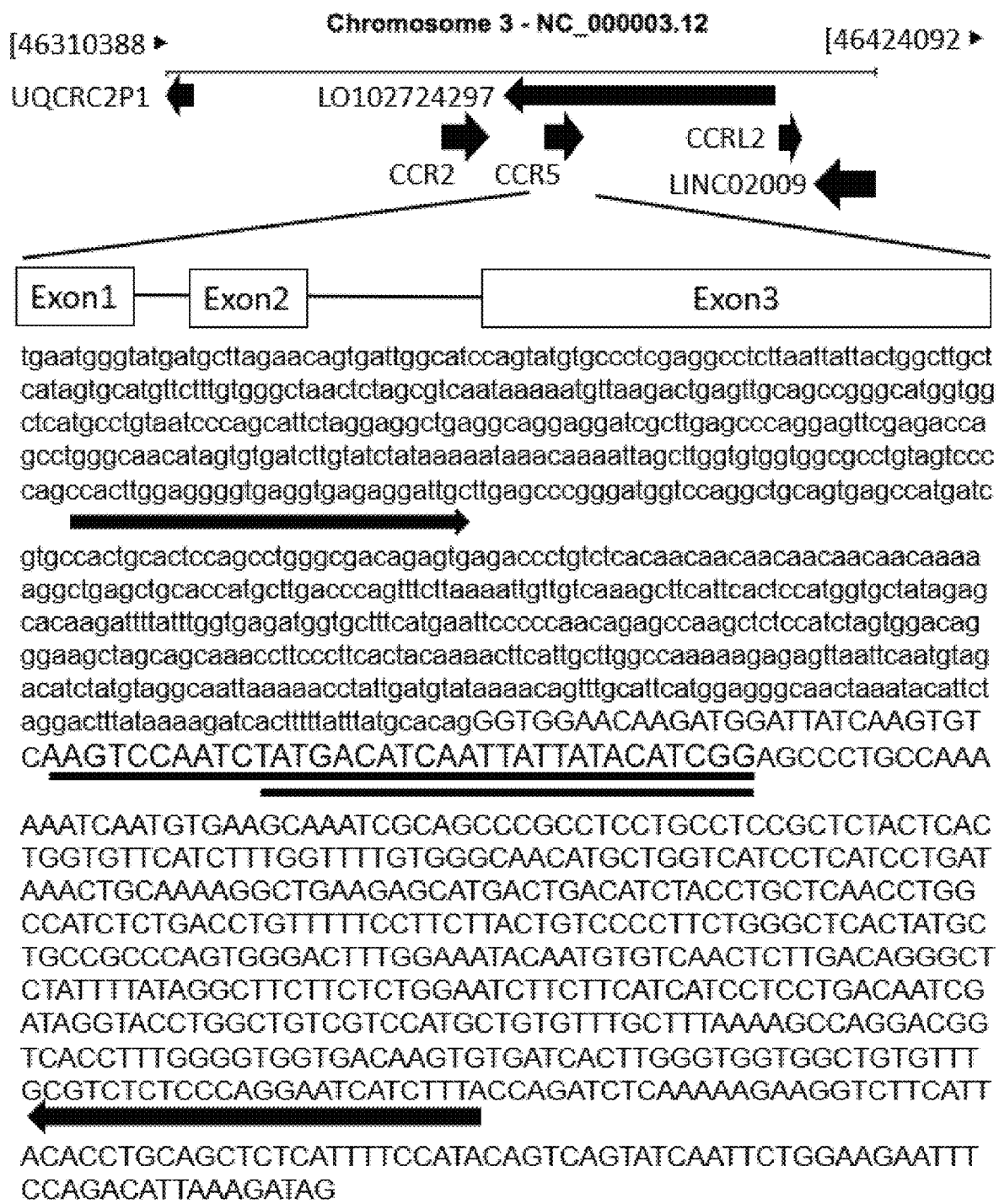
FIG. 2 is a schematic diagram showing the position of the target sequence in the CCR5 gene (SEQ ID NO: 63).

The outline of the endogenous CCR5 gene sequence, the target of the CRISPR-Cas system in this example, is described based on FIG. 2. Note that in FIG. 2, the exons are in capital letters, and the introns are in lowercase letters.

In this example, the target was the sequence within the CCR5 gene located in third chromosome short arm (P) region 21 (FIG. 2; the entire length of the nucleic acid sequence of CCR5 is shown at SEQ ID NO: 46). Specifically, the sequence within Exon 3 of the CCR5 gene was used as the target sequence. As a control, the target sequence of Cas9 was also arranged at approximately the same position. More precisely, the entire underlined sequence is the target sequence of type I CRISPR-Cas system (AAG and the following 32 bases), and the double underlined sequence is the target sequence of Cas9 (CGG and the preceding 20 bases). The sequence of crRNA was designed to allow guidance to the target sequence of the type I CRISPR-Cas system (AAG and the following 32 bases).

(Results)

The results of the above experiment were such that clone 1 having 401 bp deleted, clone 2 having 341 bp deleted, clone 3 having 268 bp deleted, and clone 4 having 344 bp deleted were obtained as compared with the original nucleic acid sequences (FIGS. 3A to 3D). This showed that it is possible to delete the endogenous DNA of human cells by the CRISPR-Cas3 system of the present invention. Specifically, it was suggested that the above CRISPR-Cas system enables editing of DNA of human cells.

This example observed clones having base pairs deleted. This fact supports that DNA cleavage takes place at multiple sites, according to the CRISPR-Cas3 system of the present invention.

DNA of several hundred base pairs (268 to 401 bp) was deleted by the CRISPR-Cas3 system of the present invention. This was more extensive than the deletion obtained by the CRISPR-Cas system using Cas9 (usually cleaved at only one site on the DNA).

Example A-3

An experiment was conducted to evaluate whether or not it is possible to cleave the endogenous DNA of human cells by the CRISPR-Cas3 system using the same method as in Example A-1.

Specifically, the nucleic acid sequence in human cells was modified to express pre-crRNA and Cas3, Cse1 (Cas8), Cse2 (Cas11), Cas5, Cas6, and Cas7 added with nuclear localization signals, and evaluation was conducted on whether or not the sequence of the endogenous EMX1 gene of the cells would be cleaved.

The same HEK 293T cells as in Example A-1 were seeded in a 24-well plate at a density of $1 \times 10^5$ cells/well and cultured for 24 hours.

Mixed with 50 μL of OPTI-MEM™ (Thermo Fisher Scientific) were 500 ng of the Cas3 plasmid, 500 ng of the Cse1 (Cas8) plasmid, 1 μg of the Cse2 (Cas11) plasmid, 1 μg of the Cas5 plasmid, 1 μg of the Cas6 plasmid, 3 μg of the Cas7 plasmid, and 500 μg of the crRNA plasmid. Further added and mixed in the above mixture were 4 μL of LIPOFECTAMINE™ (registered trademark) 2000 (Thermo Fisher Scientific) and 50 μL of OPTI-MEM™ (Thermo Fisher Scientific). The resulting mixture was incubated at room temperature for 20 min and then added to the HEK 293T cells.

Here, the structure of the expression vector of the Cas protein group used in Example A-3 is shown in FIG. 7. As shown in FIG. 7, the above expression vector is obtained by sandwiching the sequence encoding the Cas protein group with BPNLSs (bipartite NLSs) (see [Suzuki K et al. (2016) In vivo genome editing via CRISPR/Cas9 mediated homology-independent targeted integration, Nature, Vol. 540 (Issue 7631), pp. 144-149]). The amino acid sequence of BPNLS is KRTADGSEFESPKKKRKVE (SEQ ID NO: 54), and the nucleic acid sequence is (SEQ ID NO: 55)
AAGCGGACTGCTGATGGCAGTGAATTTGAGTCCCCAAAGAAGAAG

AGAAAGGTGGAA

After the above HEK 293T cells were cultured at 37° C. in a 5% $CO_2$ atmosphere for 24 hours, the medium was replaced with 1 mL of EF medium (1 mL per 1 well). Past 48 hours following transfection (24 hours after medium replacement), the cells were harvested and adjusted to a concentration of $1 \times 10^4$ cells/5 μL in PBS.

The above cells were heated at 95° C. for 10 minutes. Next, 10 mg of proteinase K was added, followed by incubation at 55° C. for 70 minutes. Furthermore, the product heat-treated at 95° C. for 10 minutes was used as a template for PCR.

By performing 40 cycles of 3-step PCR, 10 μL of the above template was amplified. Here, primers having the sequences of SEQ ID NOs: 50 and 51 were used as primers for PCR. In addition, HOTSTARTAQ™ (QIAGEN) was used as a DNA polymerase, and the 3-step PCR procedure was in accordance with the protocol attached to HOTSTARTAQ™. The product amplified by PCR was subjected to electrophoresis in a 2% agarose gel, and a band of about 900 to 1100 bp was cut out. Then, DNA was extracted from the cut gel and purified using a Gel extraction kit (QIAGEN). The specific procedure was in accordance with the protocol attached to the above kit.

Next, TA cloning was carried out using PGEM-TR EASY VECTOR SYSTEMS™ (Promega), and the above DNA was cloned. Finally, DNA cloned by alkaline prep method was extracted and analyzed by Sanger sequence. For the analysis, BIGDYE (registered trademark) Terminator v 3.1 Cycle Sequencing Kit (Thermo Fisher Scientific) and APPLIED BIOSYSTEMS 3730™ DNA Analyzer (Thermo Fisher Scientific) were used.

Figure 5A:
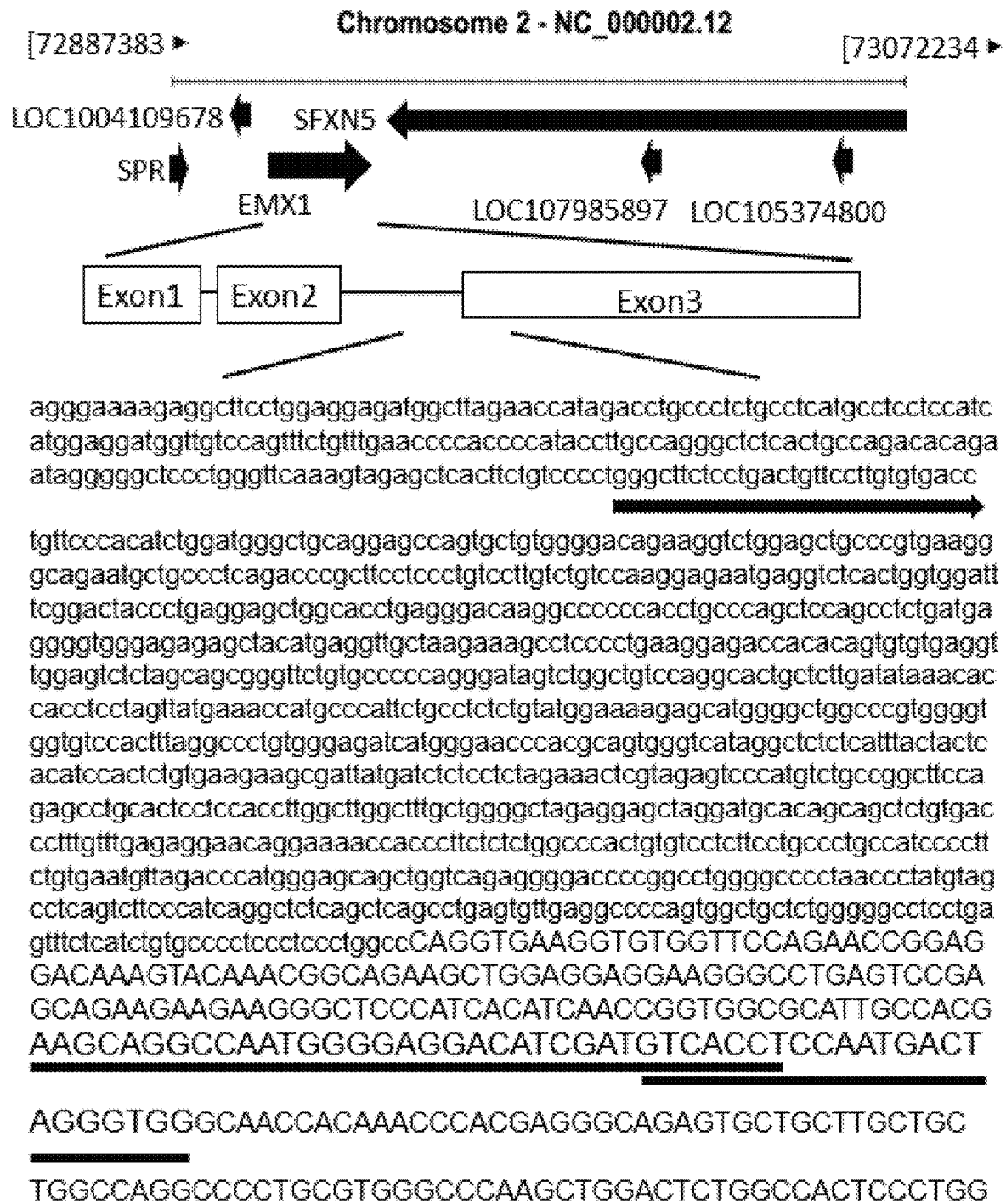

The outline of the endogenous EMX1 gene sequence, the target of the CRISPR-Cas3 system in Example A-3, is described based on FIGS. 5A-5B. Note that in FIGS. 5A-5B, the exons are in capital letters, and the introns are in lowercase letters.

In Example A-3, the target was the sequence within the EMX1 gene located in second chromosome short arm (P) region 13 (FIGS. 5A-5B; the entire length of the nucleic acid sequence of EMX1 is shown at SEQ ID NO: 49). Specifically, the sequence within Exon 3 of the EMX1 gene was used as the target sequence. As a control, the target sequence of Cas9 was also arranged at approximately the same position. More precisely, the underlined sequence located upstream is the target sequence of type I CRISPR-Cas system (AAG and the following 32 bases), and the underlined sequence located downstream is the target sequence of Cas9 (TGG and the preceding 20 bases). The sequence of crRNA used in Example A-3 was designed to allow guidance to the target sequence of the CRISPR-Cas3 system (AAG and the following 32 bases).

(Results)

The results of the above experiment were such that clone 1 having two deleted sites of 513 bp and 363 bp and clone 2 having 694 bp deleted were obtained as compared with the original nucleic acid sequences (FIGS. 6A and 6B). These experimental results also showed that it is possible to delete the endogenous DNA of human cells by the CRISPR-Cas3 system of the present invention. Specifically, it was suggested that the above CRISPR-Cas3 system enables editing of DNA of human cells.

In addition, it was similar to Example A-2 that cleavage took place at two or more sites of the double-stranded DNA, and DNA of several hundred base pairs was deleted. Therefore, the results of Example A-3 more strongly support the suggestions obtained from Example A-2.

Example A-4

The cleavage activity of the target sequence of the exogenous DNA was evaluated as follows. HEK 293T cells were caused to express the CRISPR-Cas3 system in which the nucleic acid sequences were modified and the nucleic acid sequences encoding Cascade proteins were linked.

In Example A-4, 100 ng of the reporter vector; 200 ng of each of the Cas3 plasmid, the Cascade (2A) plasmid, and the crRNA plasmid; 60 ng of pRL-TK vector (capable of expressing *Renilla* luciferase, Promega); and 300 ng of pBluescript® II KS (+) vector (Agilent Technologies) were mixed in 25 µL of Opti-MEM™ (Thermo Fisher Scientific).

Figure 9:
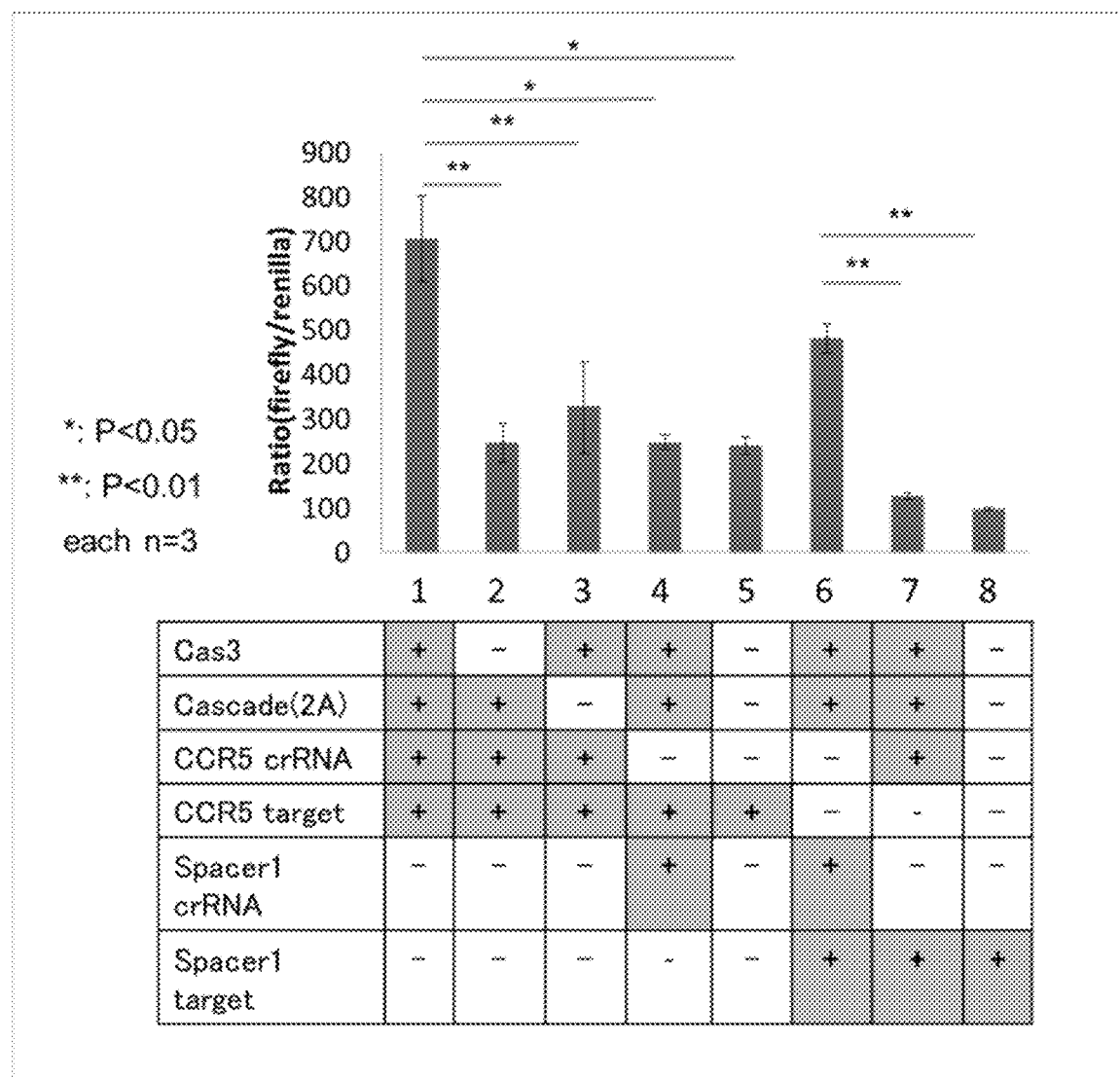
FIG. 9 is the results of SSA assay measuring cleavage activity against exogenous DNA

The conditions using the reporter vector having the target sequence derived from CCR5 as the reporter vector correspond to 1 in (b) of FIG. 9, and the conditions using the reporter vector having the spacer sequence of *E. coli* CRISPR correspond to 6 in (b) of FIG. 9.

Here, as the above reporter vectors, the two kinds of reporter vectors prepared in [1] of [Preparation Example] (that is, vectors having the structure shown in FIG. 4D) were used. In addition, as the above Cascade (2A) plasmid, the expression vectors prepared in [4] of [Preparation Example] (that is, the vector having the structure shown in FIG. 8) were used.

A dual-Luciferase assay was carried out in the same method as Example A-1 except that the above expression vectors were used.

Moreover, the same experiment was conducted under the following conditions as a control experiment.
1. Instead of either one of the Cas3 plasmid and the Cascade (2A) plasmid, the same amount of pBluescript® II KS (+) vector (Agilent Technologies) was mixed for expression (2 and 3 in FIG. 9).
2. Instead of the crRNA plasmid used in the above procedure, plasmids for expressing a crRNA not complementary to the target sequence were mixed. Specifically, for the purpose of expression, plasmids for expressing the crRNA corresponding to the spacer sequence of *E. coli* CRISPR were mixed for the target sequence derived from the CCR5 gene (4 in FIG. 9), and plasmids for expressing the gRNA corresponding to the sequence derived from the CCR5 gene were mixed when targeting the spacer sequence of *E. coli* CRISPR (7 in FIG. 9).
3. As negative controls, only a reporter vector having the target sequence derived from CCR5 (5 in FIG. 9) and only a reporter vector having the spacer sequence of *E. coli* CRISPR (8 in FIG. 9) were expressed.

(Results)

The results of the dual-Luciferase assay are shown in the graph of FIG. 9, and the experimental conditions are shown in the lower table of FIG. 9. In FIG. 9, "CCR5-target" and "spacer-target" represent the target sequence derived from CCR5 and the spacer sequence of *E. coli* CRISPR, respectively. In addition, "CCR5-crRNA" and "spacer-crRNA" represent the sequence complementary to CCR5-target and the complementary sequence to spacer-target, respectively.

As shown in FIG. 9, the system into which the crRNA plasmid complementary to the target sequence and both of the Cas3 plasmid and the Cascade (2A) plasmid were introduced exhibited cleavage activity significantly higher than that of other systems (compare between 1 and 2 to 5, and between 6, 7, and 8). Thus, it was suggested that, even in a system in which nucleic acid sequences encoding Cascade proteins are linked for expression, it is possible to specifically cleave sequences complementary to crRNA in mammalian cells by using the CRISPR-Cas system according to an embodiment of the present invention.

B. Examination of Factors and the Like Affecting Genome Editing by CRISPR-Cas3 System in Eukaryotic Cell

[Material and Method]

[1] Configuration of Cas Gene and crRNA

Constituent genes of Cas3 and Cascade (Cse1, Cse2, Cas5, Cas6, and Cas7) derived from *E. coli* K-12 strain, to which bpNLSs were added to the 5' side and 3' side, were designed and cloned by codon optimization for mammalian cells followed by gene synthesis. These genes were subcloned downstream of the CAG promoter of the pPB-CAG. EBNXN plasmid donated by Sanger Institute. Mutants of Cas3 such as H74A (dead nickase; dn), K320N (dead helicase; dh), and double mutants of S483A and T485A (dead helicase ver. 2; dh2) were prepared by self-ligation of PCR products of PrimeSTAR® MAX. Regarding the crRNA expression plasmid, a sequence of crRNA having two BbsI restriction enzyme sites at the position of the spacer under the U6 promoter was synthesized. All crRNA expression plasmids were prepared by inserting 32-base-pair double-stranded oligos of the target sequence into the BbsI restriction enzyme sites.

The Cas9-sgRNA expression plasmid px330-U6-Chimeric BB-CBh-hSpCas9 was obtained from Addgene.

Designing of gRNA employed CRISPR web tool, CRISPR design tool, and/or CRISPRdirect to predict unique target sites in the human genome. The target sequence was cloned into the sgRNA scaffold of pX330 in accordance with the protocol of the Feng Zhang laboratory.

The SSA reporter plasmid containing two BsaI restriction enzyme sites was donated by Professor YAMAMOTO Takashi at Hiroshima University. The target sequence of the genomic region was inserted into the BsaI sites. As a *Renilla* luciferase vector, pRL-TK (Promega) was obtained. All plasmids were prepared by midiprep or maxiprep method using PureLink® HiPure Plasmid Purification Kit (Thermo Fisher).

[2] Evaluation of DNA Cleavage Activity with HEK 293T Cells

An SSA assay was carried out as in Example A in order to detect DNA cleavage activity in mammalian cells. HEK 293T cells were cultured at 37° C. in 5% $CO_2$ with high-Glucose Dulbecco's modified Eagle's medium supplemented with 10% fetal bovine serum (Thermo fisher). In the wells of a 96-well plate, $0.5 \times 10^4$ cells were seeded. After 24 hours, Cas3, Cse1, Cse2, Cas7, Cas5, Cas6, and crRNA expression plasmids (each 100 ng), SSA reporter vectors (100 ng), and *Renilla* luciferase vectors (60 ng) were transfected into HEK 293T cells by using LIPOFECTAMINE™ 2000 and OPTIMEM™ (Life Technologies) in accordance with a slightly modified protocol. Twenty four hours after the transfection, a dual luciferase assay was carried out by using the DUAL-GLO™ luciferase assay system (Promega) in accordance with the protocol.

[3] Detection of Indels in HEK 293T Cells

In the wells of a 24-well plate, $2.5 \times 10^4$ cells were seeded. After 24 hours, Cas3, Cse1, Cse2, Cas7, Cas5, Cas6, and crRNA expression plasmids (each 250 ng) were transfected into HEK 293T cells by using LIPOFECTAMINE™ 2000 and OPTIMEM™ (Life Technologies) in accordance with a slightly modified protocol. TWO days after the transfection, total DNA was extracted from the harvested cells by using Tissue XS kit (Takara-bio Inc.) in accordance with the protocol. The target locus was amplified by using GFLEX™ (Takara bio Inc.) or QUICK TAQ HS DYEMIX™ (TOYOBO Co., Ltd.), followed by electrophoresis in an agarose gel. For the purpose of detecting small insertion/deletion mutations in PCR products, SURVEYOR™ Mutation Detection Kit (Integrated DNA Technologies) was used in accordance with the protocol. For TA cloning, the pCR4Blunt-TOPO plasmid vector (Life Technologies) was used in accordance with the protocol. For sequence analysis, BIGDYE™ Terminator Cycle Sequencing Kit and ABI PRISM 3130™ Genetic Analyzer (Life Technologies) were used.

For the purpose of detecting various unusual mutations, a DNA library of PCR amplification products was prepared using TRUSEQ™ Nano DNA Library Prep Kit (Illumina), and amplicon sequencing was carried out with MISEQ™ (2×150 bp) in accordance with the standard procedure by Macrogen. The raw reads of the samples were mapped to human genome hg38 by BWA-MEM. The coverage data was visualized with Integrative Genomics Viewer (IGV), and the histogram at the target region was extracted.

Reporter HEK 293T cells having mCherry-P2A-EGFP c321C>G for detecting SNP-KI (snip knock-in) in mammalian cells were donated by Professor NAKADA Shin-ichiro. The reporter cells were cultured with 1 µg/ml of puromycin. Single-stranded DNA or 500 ng of donor plasmid was co-introduced together with CRISPR-Cas3 by the method described above. All cells were harvested 5 days after the transfection, and FACS analysis was carried out using AriaIIIu™ (BD). GFP positive cells were sorted and total DNA was extracted by the method described above. SNP exchange in the genome was detected by PCR amplification using HIDI™ DNA polymerase (myPOLS Biotec).

[4] Detection of Off-Target Site Candidates

Off-target candidates of type I-E CRISPR were detected in human genome hg38 using GGGenome by two different procedures. As PAM candidate sequences, AAG, ATG, AGG, GAG, TAG, and AAC were selected in accordance with existing reports (Leenay, R. T, et al. Mol. Cell 62, 137-147 (2016), Jung, et al. Mol. Cell. 2017 Jung et al., Cell 170, 35-47 (2017)). Positions with fewer mismatches were selected in the first approach for 32 base pairs of the target sequence excluding positions of multiples of 6 because it had been reported that such positions are not recognized as target sites. In the following approach, regions completely matching 5'-end of the PAM side of the target sequence were detected and listed in descending order.

[5] Deep Sequencing of Off-Target Analysis

In whole genome sequencing, genomic DNA was extracted from the transfected HEK 293T cells and cleaved using the COVARIS™ sonicator. A DNA library was prepared using TRUSEQ™ DNA PCR-Free LT Library Prep Kit (Illumina), and genomic sequencing was carried out using HISEQ™ X (2×150 bp) in accordance with the standard procedure by Takara Bio Inc. The raw reads of the samples were mapped to human genome hg38 by BWA-MEM and cleaned by the Trimmomatic program. Discordant read pairs and split reads were excluded by samtools and Lumpy-sv, respectively. For the purpose of detecting only large deletions in the same chromosome, the read pairs mapped to different chromosomes were removed using BadMateFilter of the Genome Analysis Toolkit program. The total number of the discordant read pairs or split reads in the 100 kb region was counted by Bedtools to calculate the error rate with the negative control. SureSelectXTR custom DNA probes were designed with SureDesign under moderately stringent conditions and prepared by Agilent technologies to enrich the off-target candidates before the sequencing. The target regions were selected as follows. The probes near the target regions covered 800 kb upstream and 200 kb downstream of PAM. In the vicinity of off-target regions of CRISPR-Cas3, 9 kb upstream and 1 kb downstream of PAM candidates were covered. In the vicinity of the off-target regions of CRISPR-Cas9, 1 kb of upstream and 1 kb of downstream of PAM were covered. After preparation of the DNA library with SureSelectXT® reagent kit and custom probe kit, genome sequencing was carried out with Hiseq 2500 (2×150 bp) in accordance with the standard procedure by Takara Bio Inc. Discordant lead pairs and split leads on the same chromosome were excluded by the method described above. The total number of the discordant read pairs or split reads in the 10 kb region was counted by Bedtools to calculate the error rate with the negative control.

Figure 10B:
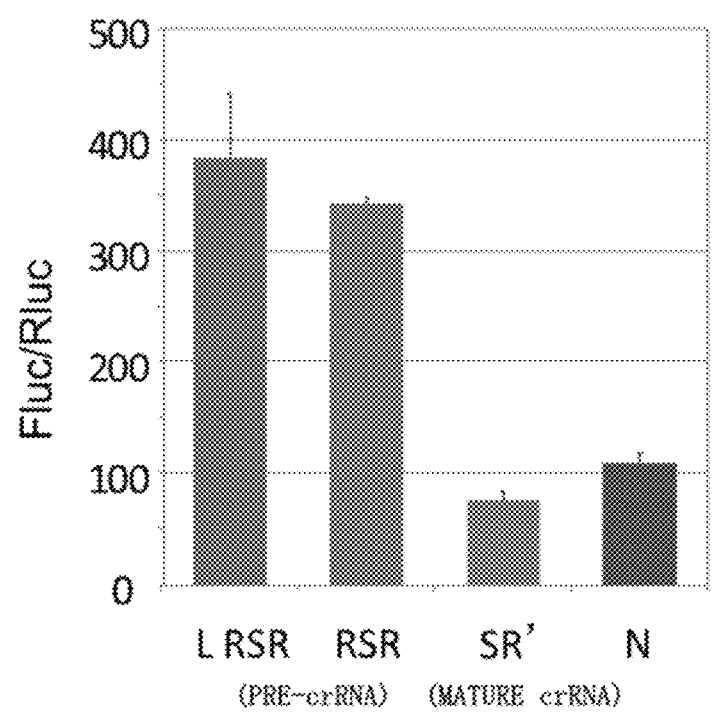
FIG. 10B is a diagram showing the results of SSA assay using the pre-crRNAs (LRSR and RSR) and the mature crRNA.

[Example B-1] Influence of Types of crRNA and Nuclear Localization Signal on DNA Cleavage Activity In Example A, genomic editing in eukaryotic cells succeeded by chance by using a CRISPR-Cas3 system containing (LRSR; leader sequence-repeated sequence-spacer sequence-repeated sequence) as a crRNA. Here, the present inventors assumed that the reason why genome editing in eukaryotic cells using the CRISPR-Cas3 system had not been successful for many years was due to the fact that mature crRNA had been used as crRNA. In light of the above, in addition to the pre-crRNA (LRSR), a pre-crRNA (RSR; repeated sequence-spacer sequence-repeated sequence) and a mature crRNA (5'-handle sequence-spacer sequence-3'-handle sequence) were prepared as crRNAs, and the genome editing efficiency was examined with the reporter system of Example A (FIGS. 10A and 10B). Note that the nucleic acid sequences of the pre-crRNA (LRSR), the pre-crRNA (RSR), and the mature crRNA are shown at SEQ ID NOs: 63, 64, and 65, respectively.

Consequently, no cleavage activity of the target DNA was observed in the CRISPR-Cas3 system using the mature crRNA. On the other hand, it was surprising that, in the case of using the pre-crRNAs (LRSR and RSR), very high cleavage activity of the target DNA was observed. These results in the CRISPR-Cas3 system are in contrast with those of the CRISPR-Cas9 system, which exhibits high DNA cleavage activity by using a mature crRNA. In addition, this fact suggests that use of a mature crRNA is one of the reasons why genomic editing in eukaryotic cells has not succeeded in the CRISPR-Cas3 system.

Figure 11:
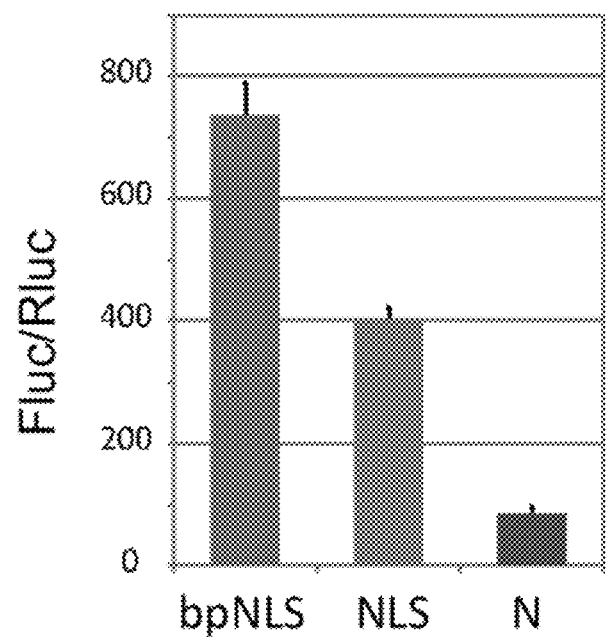
FIG. 11 shows the results of SSA assay using a single NLS or two NLSs (bpNLS) in a plasmid for the expression of the Cas3/Cascade gene.

In addition, examination was also carried out using the SV40 nuclear localization signal and bipartite nuclear translocation signal as nuclear localization signals added to Cas3 (FIG. 11). As a result, higher cleavage activity of target DNA was observed when the bipartite nuclear translocation signal was used.

Therefore, in the following experiments, the pre-CrRNA (LRSR) was used as a crRNA and the bipartite nuclear translocation signal was used as a nuclear localization signal.

[Example B-2] Influence of PAM Sequence on DNA Cleavage Activity

For the purpose of confirming the target specificity of the CRISPR-Cas3 system, the effects of various PAM sequences on DNA cleavage activity were examined (FIG. 12). In an SSA assay, the DNA cleavage activity showed various results for different PAM sequences. The highest activity was observed for 5'-AAG PAM, and AGG, GAG, TAC, ATG, and TAG also showed noticeable activity.

Figure 13:
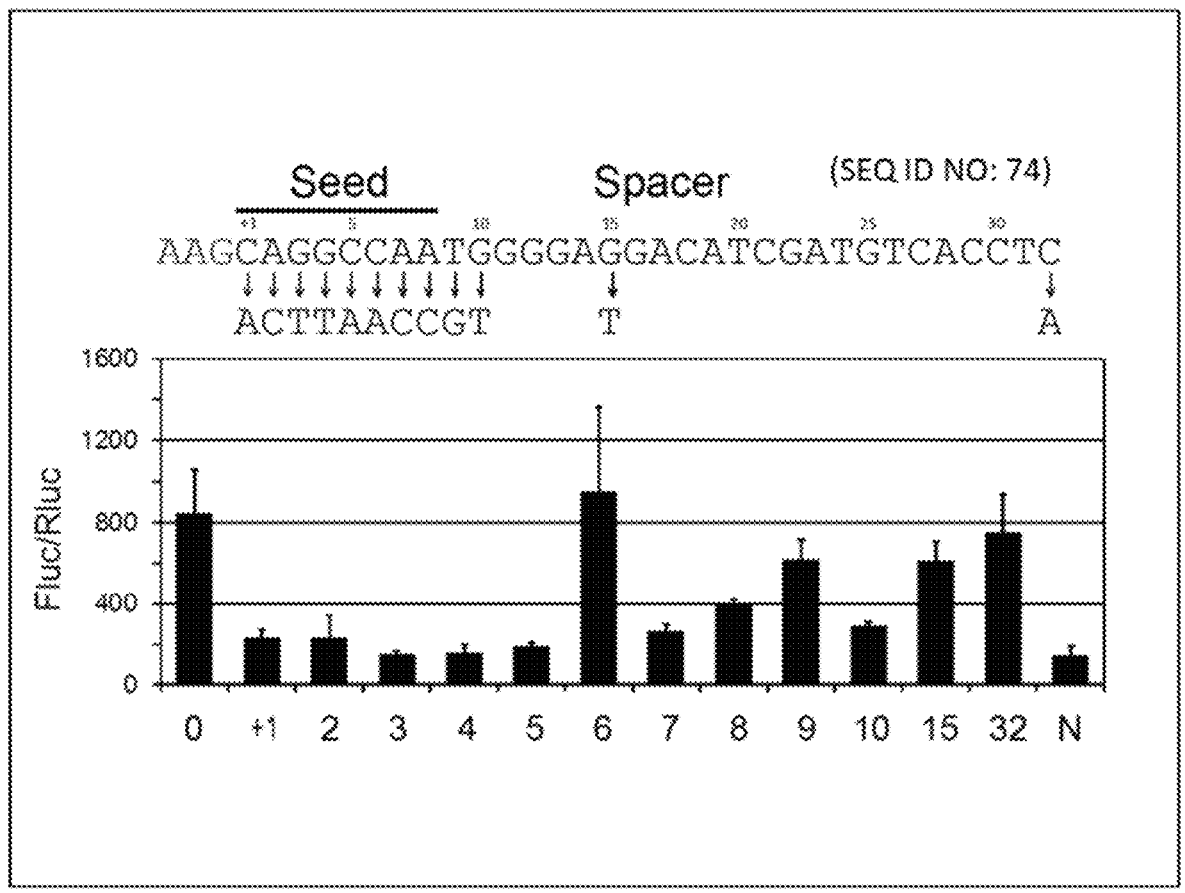
FIG. 13 is a diagram showing the effects of a single mismatch of the spacer on the DNA cleavage activity of the CRISPR-Cas3 system.

[Example B-3] Influence of Mismatch of crRNA and Spacer Sequence on DNA Cleavage Activity Studies in the past of the crystal structure of *E. coli* Cascade have shown that a heteroduplex of 5 base partitions is formed between crRNA and spacer DNA. This is due to the failure of base pairing at every sixth position by the SAM element of Cas7 effector (FIG. 13). The influence of mismatch of crRNA and spacer sequence on DNA cleavage activity was evaluated. Cleavage activity dropped dramatically at any single mismatch in the seed region (positions 1-8), except for bases not recognized as a target (position 6).

Figure 14:
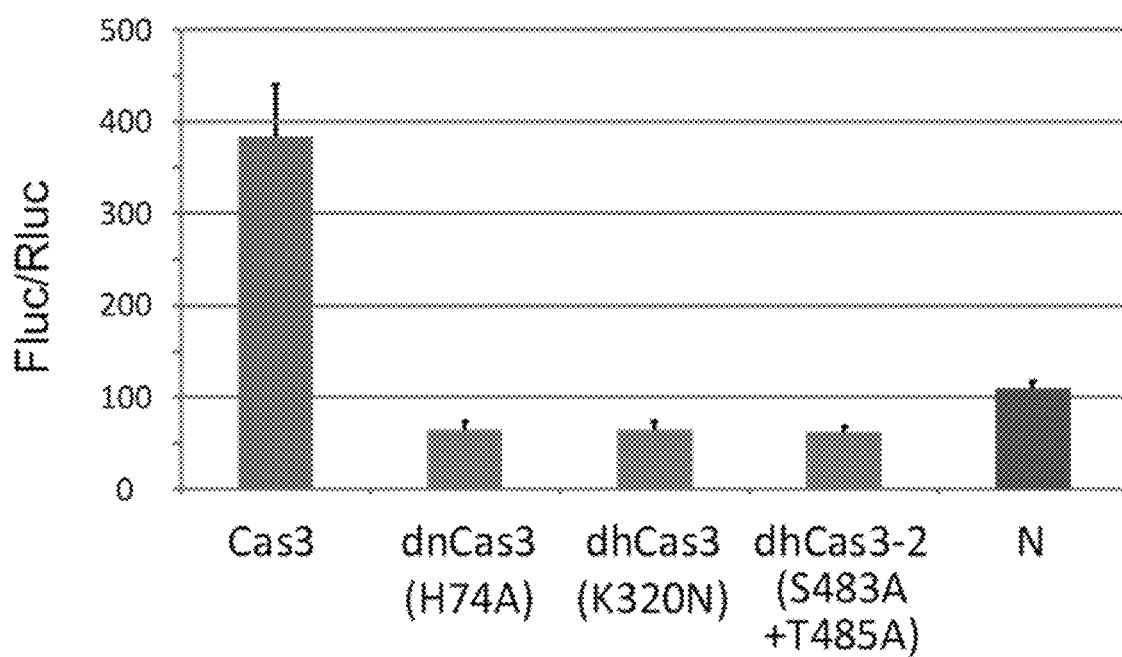
FIG. 14 is a diagram showing the effects of Cas3 mutation in HD nuclease domain (H74A), SF2 helicase domain motif 1 (K320A), and motif 3 (S483/T485A).

[Example B-4] Examination of Necessity of Domains of Cas3 in DNA Cleavage Activity In vitro characterization of the catalytic characteristics of the Cas3 protein revealed that the N-terminus HD nuclease domain cleaves the single-stranded region of the DNA substrate, and subsequently the SF2 helicase domain at the C-terminus unwinds the target DNA in an ATP-dependent manner while proceeding in 3'- to 5'-direction. Three Cas3 mutants, namely a mutant of HD domain H74A (dnCas3), a mutant of K320N of SF2 domain motif 1 (dhCas3), and a double mutant of S483A/T485A of SF2 domain motif 3 (dh2Cas3) were prepared to examine whether or not the Cas3 domain was necessary for DNA cleavage (FIG. 14). As a result, the DNA cleavage activity completely disappeared in all three mutants of Cas3 protein, revealing that Cas3 can cleave the target DNA through the HD nuclease domain and the SF2 helicase domain.

[Example B-5] Examination of DNA Cleavage Activity in Various Types of CRISPR-Cas3 Systems The type 1 CRISPR-Cas3 systems have been highly diversified (A to G of type 1, seven types in total). The above examples examined the DNA cleavage activity in eukaryotic cells in the type I-E CRISPR-Cas3 system. On the other hand, this example examined the DNA cleavage activity in other type 1 CRISPR-Cas3 systems (type I-F and type I-G). Specifically, Cas3 and Cas5-7 of *Shewanella putrefaciens* of type I-F and Cas5-8 of *Pyrococcus furiosus* of type I-G were codon optimized and cloned (FIG. 15). As a result, DNA cleavage activity was also found in these type 1 CRISPR-Cas3 systems in the SSA assay using 293T cells although there was a difference in the strength of DNA cleavage activity.

[Example B-6] Examination of Mutations Introduced into Endogenous Genes by CRISPR-Cas3 System The mutations introduced into endogenous genes by the CRISPR-Cas3 system were examined using the type I-E system. The EMX1 gene and the CCR5 gene were selected as target genes to prepare pre-crRNA (LRSR) plasmids. The 293T cells were lipofected with plasmids encoding pre-crRNA and six Cas (3, 5-8, and 11) effectors. As a result, the CRISPR-Cas3 revealed that deletion of several hundred to several thousand base pairs took place primarily in the upstream direction of 5' PAM of the spacer sequence of the target region (FIG. 16). A microhomology of 5 to 10 base pairs at the repaired junction was confirmed, which may have been caused by annealing of the complementary strands by an annealing dependent repair pathway. Note that in the mature crRNA plasmids, no genome editing was found in the EMX1 and CCR5 regions.

Figure 17:
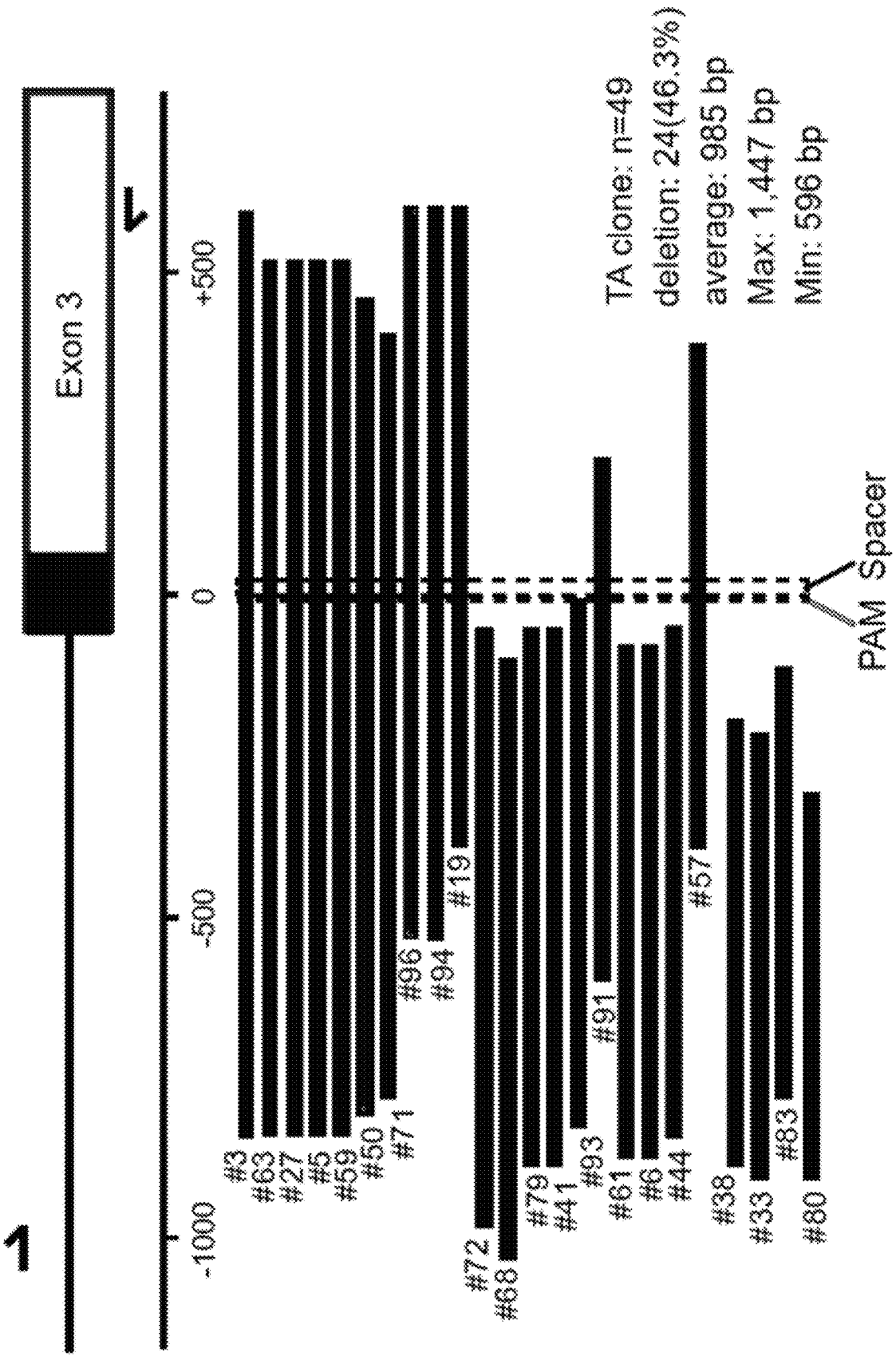
FIG. 17 is a diagram showing the position of deletion by the CRISPR-Cas3 system detected by a mass-processing sequencing of a TA clone (n=49).

Ninety six TA clones were picked up and compared with sequences of wild type EMX1 by sequencing for the purpose of further characterizing the genome editing by Cas3 by Sanger sequencing and TA cloning of PCR products (FIG. 17). Deletion of a minimum of 596 base pairs, a maximum of 1447 base pairs, and an average of 985 base pairs was observed in 24 clones out of 49 clones which could confirm sequence insertion (efficiency of 46.3%). Half of the clones (n=12) had large deletions including PAM and spacer sequences, and the other half were deleted upstream of PAM.

Further characterization of Cas3 was carried out by next generation sequencing by PCR amplification products with a primer set in broader regions such as 3.8 kb of the EMX1 gene and 9.7 kb of CCR5. Multiple PAM sites (AAG, ATG, and TTT) for targeting with type I-E CRISPR were also examined. In the amplicon sequencing, AAG was 38.2% and ATG was 56.4%. As compared with 86.4% of TTT and 86.4% of Cas9 targeting EMX1, the coverage rate in the broad genomic region upstream of the PAM site was greatly reduced. The decrease in coverage was similar when targeting the CCR 5 region. In contrast, Cas9 induced small insertions and small deletions (indels) at the target sites, while Cas3 had no small indel mutations at PAM or target site. These results suggested that the CRISPR-Cas3 system causes deletions in a wide range upstream of the target site in human cells.

Figure 18A:
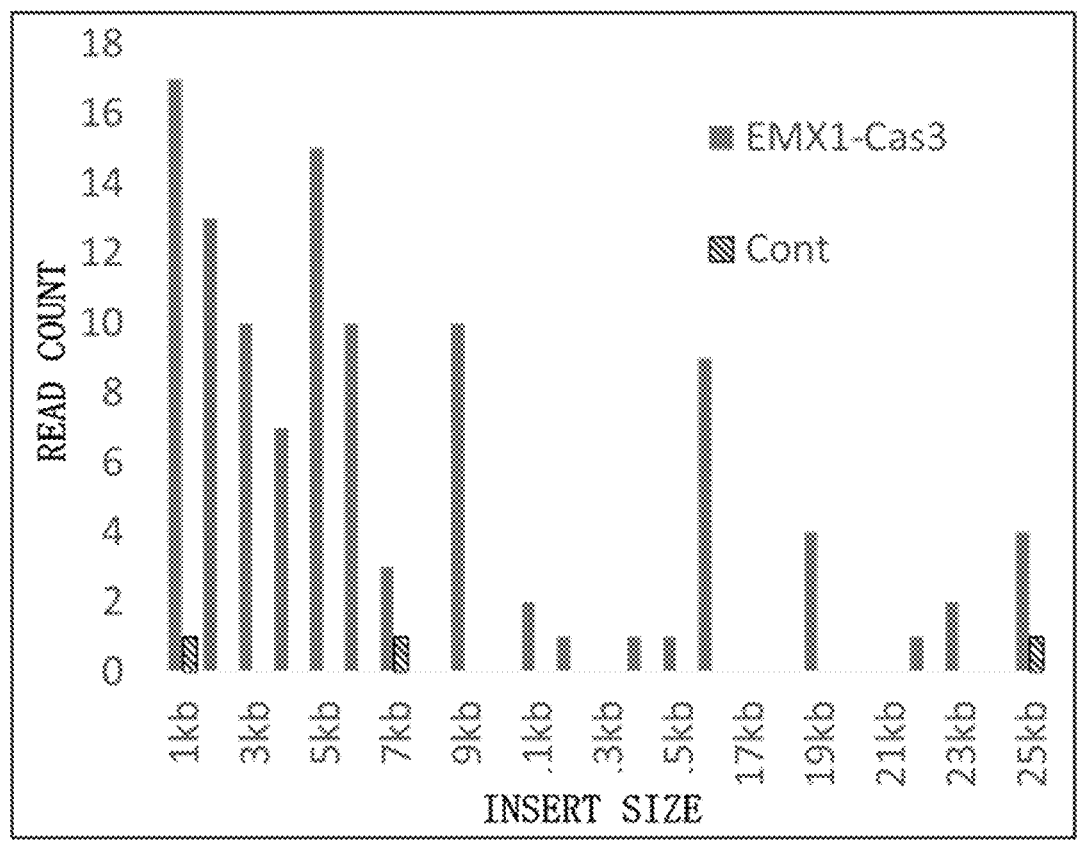
FIG. 18A is a diagram showing the number for each deletion size detected by the CRISPR-Cas3 system using a microarray-based capture sequence of 1000 kb or more around the targeted EMX1 locus.
Figure 18B:
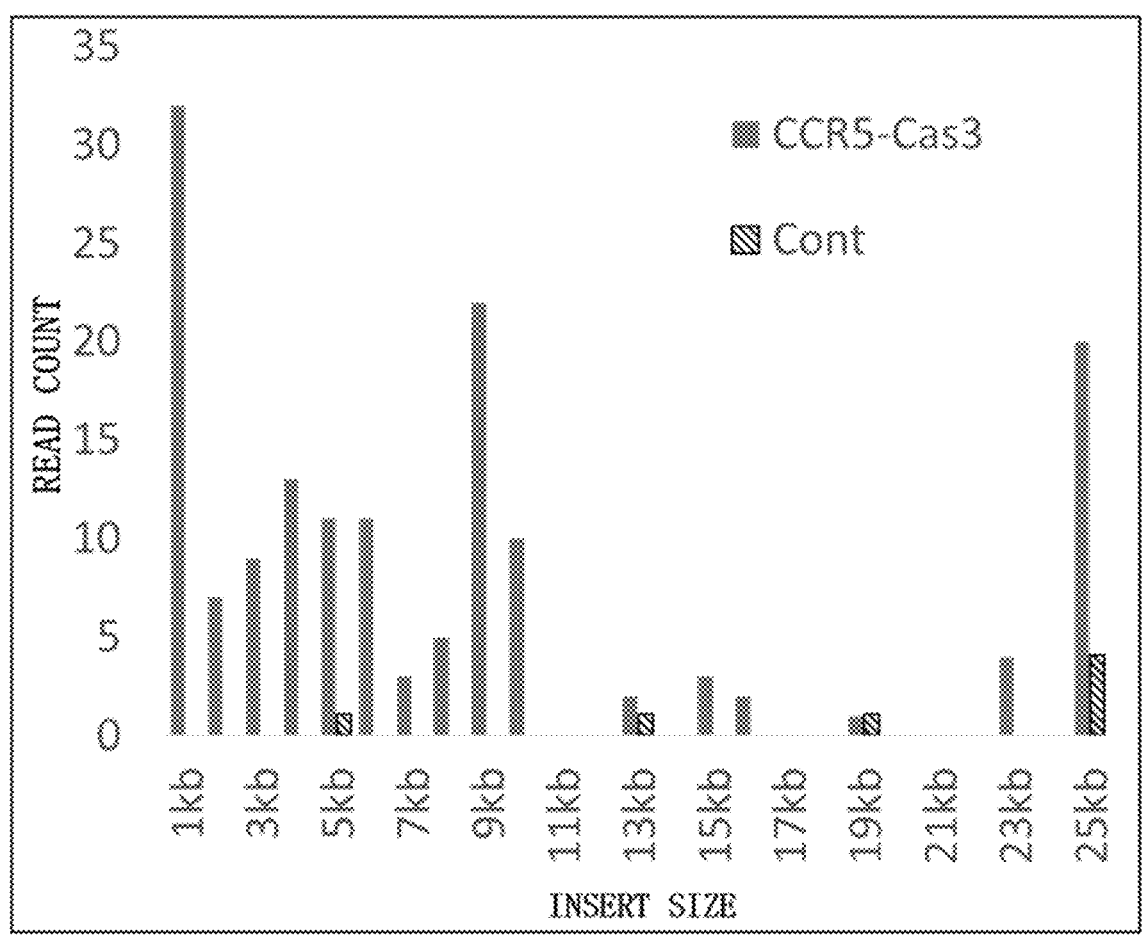
FIG. 18B is a diagram showing the number for each deletion size detected by the CRISPR-Cas3 system using a microarray-based capture sequence of 1000 kb or more around the targeted CCR5 locus.

Considering the limitations of PCR analysis such as amplification of less than 10 kb and strong bias favoring shorter PCR fragments, a microarray-based capture sequence of 1000 kb or more around the targeted EMX1 and CCR5 loci was used (FIGS. 18A and 18B). Deletion of up to 24 kb for the EMX1 locus and up to 43 kb for the CCR5 locus was observed. However, 90% of mutations at EMX1 and 95% of mutations at CCR5 were less than 10 kb. These results suggested that the CRISPR-Cas3 system may have potent nuclease and helicase activities in the eukaryotic genome.

It should be noted that whether or not undesirable off-target mutations can be induced in non-target genomic regions is a major concern particularly for clinical applications, as demonstrated in the CRISPR-Cas9 system. However, in the CRISPR-Cas3 system, no significant off-target effects were observed.

INDUSTRIAL APPLICABILITY

The CRISPR-Cas3 system of the present invention can edit DNA of eukaryotic cells, and therefore can be widely applied to fields requiring genome editing such as medicine, agriculture, forestry, and fisheries, industry, life science, biotechnology, and gene therapy.

The invention claimed is:

1. A method for cleaving endogenous DNA of a eukaryotic cell in the eukaryotic cell, comprising:
   introducing a CRISPR-Cas3 system that can cleave endogenous DNA in a eukaryotic cell, wherein the CRISPR-Cas3 system is a Type I-D CRISPR-Cas3 system, and wherein the CRISPR-Cas3 system includes the following (A) to (C):
   (A) a Cas3 protein with helicase activity, a polynucleotide encoding the protein, or an expression vector containing the polynucleotide,
   (B) Cascade proteins comprising Cas10, Cas5, Cas6, and Cas7, a polynucleotide encoding the Cascade proteins, or an expression vector containing the polynucleotide, and
   (C) a pre-crRNA which targets the endogenous DNA in the eukaryotic cell, a polynucleotide encoding the pre-crRNA, or an expression vector containing the polynucleotide.

2. The method according to claim 1, further comprising
   cleaving the pre-crRNA which targets the endogenous DNA with a protein constituting the Cascade proteins after introducing the CRISPR-Cas3 system into the eukaryotic cell.

3. The method according to claim 1, wherein
   a nuclear localization signal is added to the Cas3 protein and/or one or more of the Cascade proteins.

4. The method according to claim 3, wherein
   the nuclear localization signal is a bipartite nuclear localization signal.

5. A method for cleaving endogenous DNA of a nonhuman animal or plant in the nonhuman animal or plant, comprising:
   introducing a CRISPR-Cas3 system that can cleave endogenous DNA in a nonhuman animal or plant, wherein the CRISPR-Cas3 system is a Type I-D CRISPR-Cas3 system, and wherein the CRISPR-Cas3 system includes the following (A) to (C):
   (A) a Cas3 protein with helicase activity, a polynucleotide encoding the protein, or an expression vector containing the polynucleotide,
   (B) Cascade proteins comprising Cas10, Cas5, Cas6, and Cas7, a polynucleotide encoding the Cascade proteins, or an expression vector containing the polynucleotide, and
   (C) a pre-crRNA which targets the endogenous DNA in the nonhuman animal or plant, a polynucleotide encoding the pre-crRNA, or an expression vector containing the polynucleotide.

* * * * *